United States Patent [19]
Arrhenius et al.

[11] Patent Number: 5,936,065
[45] Date of Patent: Aug. 10, 1999

[54] CS-1 PEPTIDOMIMETICS, COMPOSITIONS AND METHODS OF USING THE SAME

[75] Inventors: Thomas S. Arrhenius; Mariano J. Elices, both of San Diego; Federico C. A. Gaeta, Olivenhain, all of Calif.

[73] Assignee: Cytel Corporation, San Diego, Calif.

[21] Appl. No.: 08/462,424

[22] Filed: Jun. 5, 1995

Related U.S. Application Data

[63] Continuation-in-part of application No. 08/349,024, Dec. 2, 1994, abandoned, which is a continuation-in-part of application No. 08/164,101, Dec. 6, 1993, abandoned.

[51] Int. Cl.$^6$ ................................................. C07K 5/08
[52] U.S. Cl. ........................ 530/331; 530/330; 514/17; 514/18; 514/19
[58] Field of Search .................... 514/17, 18, 19; 530/330, 331

[56] References Cited

U.S. PATENT DOCUMENTS

| | | | |
|---|---|---|---|
| 4,822,606 | 4/1989 | Snyderman et al. | 424/88 |
| 5,294,511 | 3/1994 | Furcht et al. | 435/240.242 |
| 5,387,504 | 2/1995 | Mumford | 435/7.1 |

FOREIGN PATENT DOCUMENTS

| | | |
|---|---|---|
| 361977 | 4/1990 | European Pat. Off. . |
| WO 91/03252 | 3/1991 | European Pat. Off. . |
| WO 93/12809 | 7/1993 | European Pat. Off. . |

OTHER PUBLICATIONS

Ioria, et al., *J. Med. Chem.* 34:2615–2623 (1991).

Komoriya, Akira et al., "The Minimal Essential Sequence for a Major Cell Type–Specific Adhesion Site (CS1) Within the Alternatively Splice Type III Connecting Segment Domain of Fibronectin is Leucine–Aspartic Acid–Valine." *J. Biol. Chem.* 266:15075–15079 (1991).

Elices, Mariano "The Integrin $\alpha_r\beta_1$ (VLA–4) as a Therapeutic Target." *Cell Adhesion and Human Disease.* Wiley, Chichester (Ciba Foundation Symposium 189) pp. 79–90 (1995).

Nowlin, Dawn M., "A Novel Cyclic Pentapeptide Inhibits $\alpha4\beta1$ and $\alpha5\beta1$ Integrin–mediated Cell Adhesion." *J. Biol. Chem.* 268:20352–20359 (1993).

Mousa, Skaer A. et al., "Antiplatelet Efficacy and Specificity of DMP728, a Novel Platelet GP11B/IIIa Receptor Antagonist." *Clin. Pharm.* 83:373–382 (1993).

Pfaff, Martin et al., "Seletive Recognition of Cyclic RGD Peptides of NMR Defined Conformation by $\alpha V\beta 3$, $\alpha 5\beta 1$ Integrins." *J. Biol. Chem.* 269:20233–20238 (1994).

*Primary Examiner*—Cecilia J. Tsang
*Assistant Examiner*—David Lukton
*Attorney, Agent, or Firm*—Campbell & Flores LLP

[57] ABSTRACT

The present invention contemplates a compound defined by the following formula:

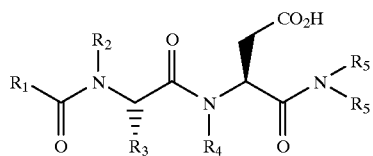

that inhibits the binding between the VLA-4 and the fibronectin CS-1 compound. Pharmaceutical compositions containing a contemplated compound and methods for treating immunoinflammatory conditions using the compound are also disclosed.

2 Claims, 7 Drawing Sheets

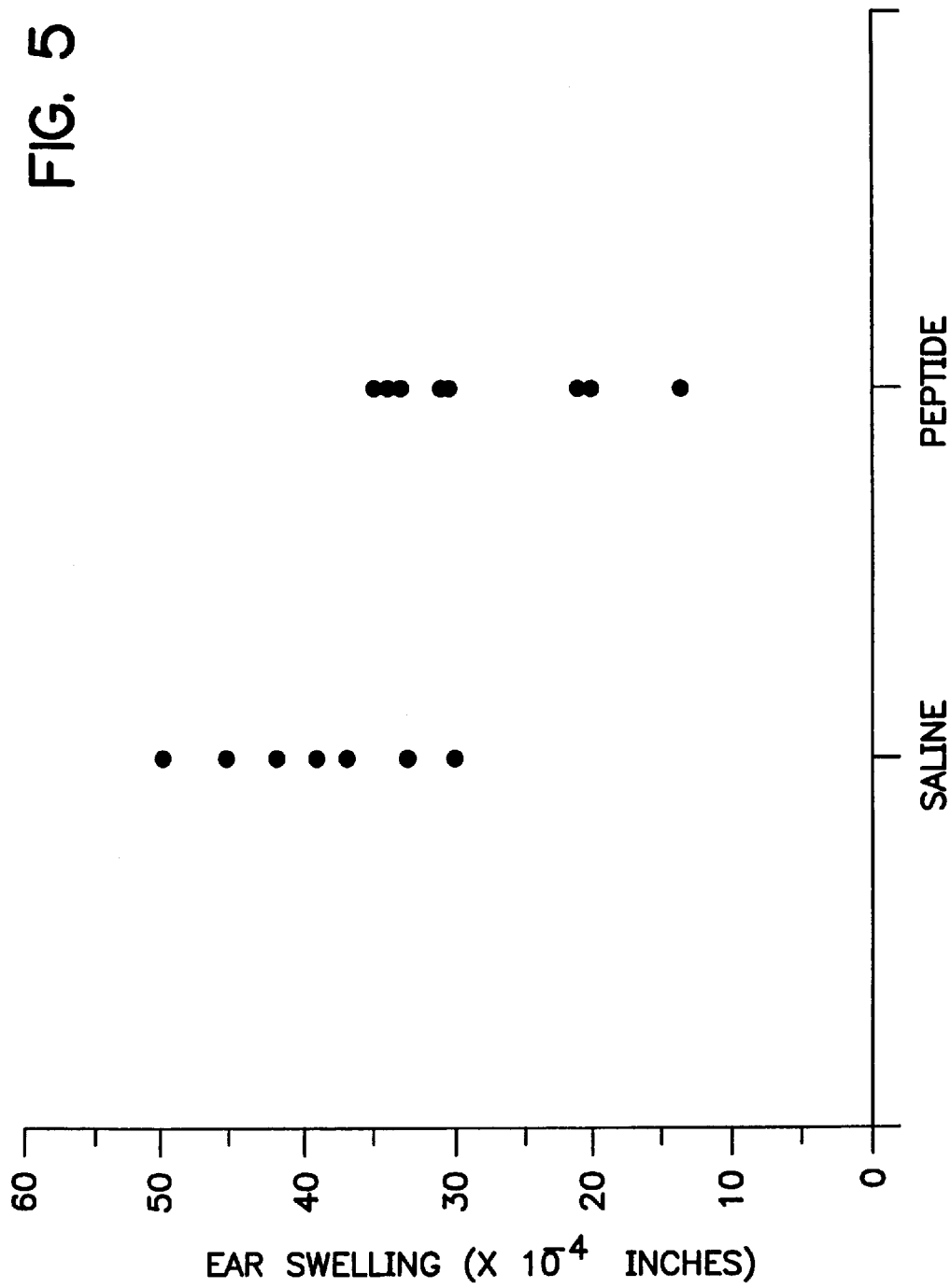

CS-1 PEPTIDOMIMETICS, COMPOSITIONS AND METHODS OF USING THE SAME

CROSS-REFERENCE TO RELATED APPLICATION

This is a continuation-in-part of application Ser. No. 08/349,024, filed Dec. 2, 1994, now abandoned which is continuation-in-part of application Ser. No. 08/164,101, filed Dec. 6, 1993, now abandoned whose disclosures are incorporated by reference.

DESCRIPTION

1. Technical Field

The present invention relates to binding of inflammatory cells to endothelial cells that express the CS-1 portion of fibronectin on their surfaces, and more particularly to the inhibition of that binding by peptidomimetic compounds of minimal length.

2. Background Art

The immune response relies on leukocyte trafficking and immune surveillance as one of the underpinnings of host defense. Not only does this immune surveillance allow leukocytes to recirculate through lymphoid tissues normally, but also permits rapid leukocyte recruitment and extravasation to adjacent tissues at sites of inflammation. The $\alpha 4\beta 1$ (CD49d/CD29, VLA-4) cell adhesion receptor is an active participant in these leukocyte trafficking functions [Hemler, *Ann. Rev. Immunol.*, 8:365–400 (1990); Hemler et al., *Immunol. Rev.*, 114:45–65 (1990)].

The VLA-4 integrin heterodimer was discovered independently by three research groups and identified as a surface antigen on lymphocytes [Sanchez-Madrid et al., *Eur. J. Immunol.*, 16:1343–1349 (1986); Clayberger et al., *J. Immunol.*, 138:1510–1514 (1987); Hemler et al., *J. Biol. Chem.*, 262:11478–11485 (1987)]. Within the integrin family, VLA-4 is unique on several counts: (I) in contrast to related members of the $\beta 1$ subfamily, VLA-4 is predominantly expressed on cells of the hematopoietic lineage [Hemler, *Ann. Rev. Immunol.*, 8:365–400 (1990)], and is functionally involved in cell-cell, as well as cell-extracellular matrix (ECM) adhesive interactions [Hemler, *Ann. Rev. Immunol.*, 8:365–400 (1990)]; (ii) despite sequence homology with other integrin $\alpha$ subunits, the $\alpha 4$ subunit stands apart from the two major structural clusters of $\alpha$ subunits because $\alpha 4$ lacks an inserted I-domain, and does not undergo post-translational cleavage near the transmembrane region [Hemler, *Ann. Rev. Immunol.*, 8:365–400 (1990); Hynes, *Cell,* 69:11–25 (1992)]; and (iii) $\alpha 4$ contains a trypsin-like cleavage site that results in cell type-specific surface expression of at least two different structural variants termed $\alpha 4$–150 and $\alpha 4$–80/70 [Pulido et al., *FEBS Lett.*, 294:121–124 (1991); Teixido et al., *J. Biol. Chem.*, 267:1786–1791 (1992); Rubio et al., *Eur. J. Immunol.*, 22:1099–1102 (1992)].

The VLA-4 integrin appears to be one of the earliest adhesion receptors found on CD34-expressing hematopoietic stem cells [Teixido et al., *J. Clin. Invest.*, 90:358–367 (1992)]. However, VLA-4 is expressed only on mature T and B lymphocytes, natural killer (NK) cells, monocytes, basophils and eosinophils, but not on erythrocytes, platelets and neutrophils [Hemler, *Ann. Rev. Immunol.*, 8:365–400 (1990); Gismondi et al., *J. Immunol.*, 146:384–392 (1991); Walsh et al., *J. Immunol.*, 146:3419–3423 (1991); Bochner et al., *J. Exp. Med.*, 173:1553–1556 (1992); Dobrina et al., *J. Clin. Invest.*, 88:20–26 (1991); Weller et al., *Proc. Natl. Acad. Sci. USA*, 88:7430–7433 (1991)].

To date, most adhesion functions mediated by VLA-4 can be explained by a direct molecular interaction between the VLA-4 integrin and either of two separate counter receptor structures, namely, the cytokine-inducible vascular cell adhesion molecule-1 (VCAM-1) [Elices et al., *Cell,* 60:577–584 (1990); Rice et al., *J. Exp. Med.*, 171:1369–1374 (1990); Schwartz et al., *J. Clin, Invest.*, 85:2019–2022 (1990); Carlos et al., *Blood,* 76:965–970 (1990)], and a subset of the ubiquitous ECM protein fibronectin [Wayner et al., *J. Cell Biol.*, 109:1321–1330 (1989); Guan et al., *Cell,* 60:53–61 (1990); Ferreira et al.,*J. Exp. Med.*, 171:351–356 (1990); Elices et al., *Cell,* 60:577–584 (1990)].

VCAM-1 is a member of the immunoglobulin (Ig) gene superfamily [Osborn et al., *Cell,* 59:1203–1211 (1989); Rice et al., *Science,* 246:1303–1306 (1989)] that is expressed predominantly in vascular endothelium in response to pro-inflammatory cytokines such as IL-1, TNF$\alpha$, and IL-4 [Osborn et al., *Cell,* 59:1203–1211 (1989); Rice et al., *Science,* 246:1303–1306 (1989); Thornhill et al., *J. Immunol.*, 145:865–872 (1990); Masinovsky et al., *J. Immunol.*, 145:2886–2895 (1990); Thornhill et al., *J. Immunol., 146:592–598*(199); Schleimer et al.,*J. Immunol.*, 148:1086–1092 (1992); Birdsall et al., *J. Immunol.*, 148:2717–2723 (1992); Swerlick et al., *J. Immunol.*, 149:798–705 (1992); Briscoe et al., *J. Immunol.*, 149:2954–2960 (1992)]. The VLA-4 binding sites on VCAM-1 have been mapped to the outermost N-terminal (first) Ig-like region of the 6-Ig-like domain VCAM-1 isoform [Taichman et al., *Cell Regul.*, 2:347–355 (1991); Vonderheide et al., *J. Exp. Med.*, 175:1433–1442 (1992); Osborn et al.,*J. Exp. Med.*, 176:99–107 (1992)], and the first and fourth N-terminal Ig-like regions of the 7-Ig-like domain VCAM-1 isoform [Vonderheide et al.,*J. Exp. Med.*, 175:1433–1442 (1992); Osborn et al., *J. Exp. Med.*, 176:99–107 (1992)]. Discrete amino acid sequences within the two separate Ig-like domains in VCAM-1 recognized by the VLA-4 integrin remain to be defined.

In contrast, a high affinity peptide recognition sequence for VLA-4 within fibronectin (FN) has been identified [Wayner et al., *J. Cell. Biol.*, 109:1321–1330 (1989); Ferreira et al.,*J. Exp. Med.*, 171:351–356 (1990); Guan et al., *Cell,* 60:53–61 (1990); Mould et al., *J. Biol. Chem.*, 25:4020–4024 (1990); Garcia-Pardo et al., *J. Immunol.*, 144:3361–3366 (1990); Komoriya et al., *J. Biol. Chem.*, 266:15075–15079 (1991)]. That sequence comprises a 25-amino acid residue stretch, termed CS-1 [Humphries et al., *J. Cell Biol.*, 103:2637–2647 (1986); Humphries et al., *J. Biol. Chem.*, 262:6886–6892 (1987)].

The FN gene contains three separate exons termed EIIIA, EIIIB and V or IIICS, which are subject to alternative splicing [Hynes, "Fibronectin", Springer-Verlag, New York (1990)]. The presence of additional acceptor and donor splice signals within the IIICS region permits generation of increased diversity in FN by virtue of multiple IIICS polypeptide variants, for instance, five in human FN [Vibe-Pedersen et al., *FEBS Lett.*, 207:287–291 (1987); Hershberger et al., *Mol. Cell. Biol.*, 10:662–671 (1990)]. Consequently, only a subset of these molecular variants expresses the 25-amino acid CS-1 sequence recognized by VLA-4 [Wayner et al.,*J. Cell. Biol.*, 109:1321–1330 (1989); Guan et al., *Cell,* 60:53–61 (1990)].

A minimal essential sequence for specific VLA-4 recognition of CS-1 has been identified as the tripeptide Leu-Asp-Val (LDV) [Komoriya et al., *J. Biol. Chem.*, 266:15075–15079 (1991); Wayner et al., *J. Cell. Biol.*, 116:489–497 (1992); Wayner WO 91/03252 published Mar.

21, 1991; Wayner WO 93/12809 published Jul. 8, 1993; and Humphries WO 92/13887, published Aug. 20, 1992] albeit VLA-4 binds to LDV with at least two orders of magnitude lower affinity than to the native CS-1 25-mer. Nowlin et al., *J. Biol. Chem.*, 268(1):20352–20359 (1993) recently described a cystine-linked cyclic pentapeptide said to inhibit binding by both the Arg-Gly-Asp and CS-1 regions of fibronectin.

VLA-4 shares with other members of the β1 integrin subfamily the ability to promote binding and penetration of microbial pathogens into mammalian cells. Thus, specific interactions of β1 integrins with the bacterial protein invasin [Isberg et al., *Cell*, 60:861–871 (1990); Ennis et al., *J. Exp. Med.*, 177:207–212 (1993)], as well as the protozoan *Trypanosoma cruzi* [Fernandez et al., *Eur. J. Immunol.*, 23:552–557 (1993)] have been described.

A multitude of in vitro studies suggest interactions of VLA-4 with its two known ligands, VCAM-1 and CS-1 FN, have profound biological significance. For instance, VLA-4 binding to VCAM-1 has been demonstrated in adhesion to cytokine-stimulated vascular endothelium by lymphocytes [Elices et al., *Cell*, 60:577–584 (1990); Rice et al., *J. Exp. Med.*, 171:1369–1374 (1990); Schwartz et al., *J. Clin, Invest.*, 85:2019–2022 (1990); Carlos et al., *Blood*, 76:965–970 (1990); Shimizu et al., *J. Cell Biol.*, 113:1203–1212 (1991)], monocytes [Carlos et al., *Blood*, 77:2266–2271 (1991); Jonjic et al., *J. Immunol.*, 148:2080–2083 (1992)], natural killer (NK) cells [Allavena et al., *J. Exp. Med.*, 173:439–448 (1991)], and eosinophils [Walsh et al., *J. Immunol.*, 146:3419–3423 (1991); Bochner et al., *J. Exp. Med.*, 173:1553–1556 (1992); Dobrina et al., *J. Clin. Invest.*, 88:20–26 (1991); Weller et al., *Proc. Natl. Acad. Sci. USA*, 88:7430–7433 (1991)]. Because of its involvement in mediating leukocyte-endothelial attachment, VLA-4/VCAM-1 interactions are considered key in inflammation.

The VLA-4/CS-1 interaction, in turn, has been widely documented in hematopoiesis where adhesive interactions between hematopoietic progenitors expressing VLA-4 [Hemler et al., *Immunol. Rev.*, 114:45–65 (1990); Williams et al., *Nature*, 352:438–441 (1991); Roldan et al., *J. Exp. Med.*, 175:1739–1747 (1992); Sawada et al., *J. Immunol.*, 149:3517–3524 (1992); Wadsworth et al., *J. Immunol.*, 150:847–857 (1993)] and their ECM microenvironment play a critical role in precursor maturation and differentiation. Thus, CS-1 peptides have been shown to inhibit (I) attachment of murine hematopoietic stem cells to ECM derived from bone marrow stroma [Williams et al., *Nature*, 352:438–441 (1991)], (ii) immunoglobulin secretion by bone marrow-derived B cell progenitors [Roldan et al., *J. Exp. Med.*, 175:1739–1747 (1992)], (iii) bursal and postbursal development of chicken B cells [Palojoki et al., *Eur. J. Immunol.*, 23:721–726 (1993)], and (iv) thymocyte adhesion and differentiation induced by thymic stromal cell monolayers [Utsumi et al., *Proc. Natl. Acad. Sci. USA*, 88:5685–5689 (1991); Sawada et al., *J. Immunol.*, 149:3517–3524 (1992)]. VLA-4/CS-1 may also be involved in embryonic development, because CS-1 peptides have been shown to interfere with migration of avian neural crest cells [Dufour et al., *EMBO J.*, 7:2661–2671 (1988)].

In addition to VCAM-1, FN and CS-1 have also been implicated in the pathology of rheumatoid arthritis (RA) [Laffon et al., *J. Clin. Invest.*, 88:546–552 (1992)]. A role for the CS-1 splicing variant of FN has been established in mediating migration of inflammatory cells such as eosinophils across endothelial cell monolayers of VLA-4-expressing leukocytes [Kuijpers et al., *J. Exp. Med.*, 178:279–284 (1993)].

The vast body of work suggesting that VLA-4 plays a role in leukocyte trafficking and inflammation has been largely confirmed by in vivo studies using anti-VLA-4 antibodies in various animal models. Essentially, the skin, brain, kidney, lung and gut are targets of a wide variety of VLA-4-dependent inflammatory reactions mostly resulting from recruitment of mononuclear leukocytes and eosinophils.

More specifically, these in vivo studies are as follows: contact hypersensitivity (CH) and delayed type hypersensitivity (DTH) in the mouse and rat [Ferguson et al., *Proc. Natl. Acad. Sci. USA*, 88:8072–8076 (1991); Issekutz, *Cell Immunol.*, 138:300–312 (1991); Issekutz, *J. Immunol.*, 147:4178–4184 (1991); Elices et al., *Clin. Exp. Rheumatol.*, 11:S77–80 (1993); Chisholm, et al., *Eur. J. Immunol.*, 23:682–688 (1993)]; experimental autoimmune encephalomyelitis (EAE) in the mouse and rat [Yednock et al., *Nature*, 356:63–66 (1992); Baron et al., *J. Exp. Med.*, 177:57–68 (1993)]; nephrotoxic nephritis in the rat [Mulligan et al., *J. Clin. Invest.*, 91:577–587 (1993)]; passive cutaneous anaphylaxis in the guinea pig [Weg et al., *J. Exp. Med.*, 177:561–566 (1993)]; immune complex-induced lung injury in the rat [Mulligan et al., *J. Immunol.*, 150:2401–2406 (1993); Mulligan et al., *J. Immunol.*, 150:2407–2417 (1993)], spontaneous colitis in the monkey [Poldolsky et al., *J. Clin. Invest.*, 92:372–380 (1993)] and asthma in sheep [Lobb, WO 92/13798 published Jul. 22, 1993].

Thus, a preliminary conclusion from in vivo results is that VLA-4 contributes to inflammatory responses that emulate chronic conditions in humans. In an in vivo model of murine contact hypersensitivity, the CS-1 peptide partially inhibited recruitment of T lymphocytes to skin inflammatory sites [Ferguson et al., *Proc. Natl. Acad. Sci. USA*, 88:8072–8076 (1991)]. Because the Arg-Gly-Asp peptide from the cell adhesion domain of FN was also inhibitory in this animal model, the authors concluded that emigration of immune T cells to sites of antigenic challenge in the tissue could be facilitated by the interaction of leukocyte integrins with ECM proteins such as FN [Ferguson et al., *Proc. Natl.. Acad, Sci. USA*, 88:8072–8076 (1991)].

In a more recent study, Elices and coworkers [Elices et al., *Clin, Exp. Rheumatol.*, 11:S77–80 (1993)] were unable to reproduce inhibition of contact hypersensitivity with the native CS-1 peptide. Instead, they found that the CS-1 peptide was rapidly cleared from blood circulation by proteolytic degradation.

The role of VLA-4 and the CS-1 peptide in various chronic and acute immunoinflammatory disease states having been established, it would be of importance if compounds could be found that inhibit the VLA-4-lymphocyte interaction and were other than anti-VLA-4 antibodies that can themselves induce an immune response on repeated administration or the CS-1 peptide that is large and costly to make, and also is subject to rapid degradation.

BRIEF SUMMARY OF THE INVENTION

The present invention contemplates CS-1 peptidomimetic inhibitor compounds, their compositions and methods (processes) for using those inhibitor compounds.

A contemplated compound corresponds to the following formula:

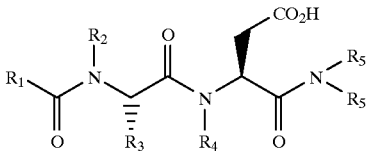

where $R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0; to about 3carbon atoms long. The lower alkyl, lower alkyl alcohol, or lower thioalkyl group can be branched.

$R_4$ is a H or $R_4$ and $R_1$ form the $R_1$ ring structure.

$R_5$ is H or $R_5$ and $R_6$ form a $R_5$ ring structure. The $R_5$ ring structure is a fused 6,6- ring structure and can be aromatic, partially saturated, or saturated.

$R_6$ is a benzyl, or 1,1 diphenylmethine group, the $R_5$ ring structure, a group of the formula

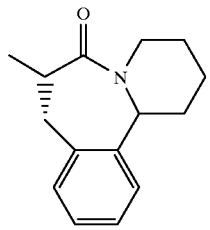

or a group of the formula

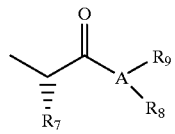

where A is nitrogen or oxygen and, when A is nitrogen, $R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$ the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is the $R_7$ ring structure. The $R_8$ ring structure is a 5-,6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

When A is oxygen, $R_8$ is a lower alkyl that can be branched and $R_9$ is absent.

A contemplated compound corresponds to the following formula:

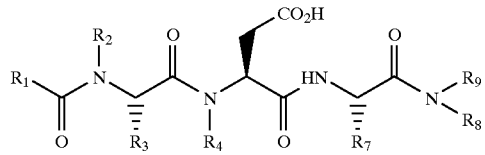

where $R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

A contemplated compound corresponds to the following formula:

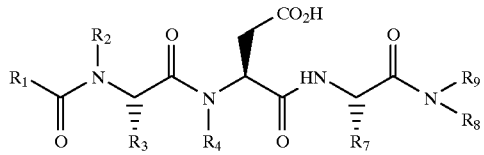

where $R_1$ is a $R_1$ ring structure, lower alkyl, or lower amino alkyl. The $R_1$ ring structure is connected by a spacer 0 to about 5 atoms long forming from one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_9$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

A contemplated compound corresponds to the following formula:

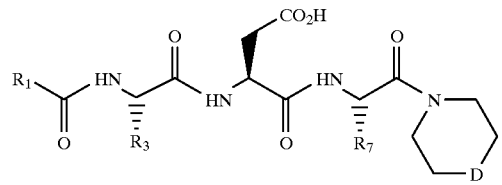

where D is a carbon, nitrogen, oxygen, or sulfur atom optionally substituted by a lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido group.

$R_1$ is a $R_1$ ring structure, lower alkyl, or lower amino alkyl. The $R_1$ ring structure is connected by a spacer 0 to about 5 atoms long forming from one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

A contemplated compound corresponds to the following formula:

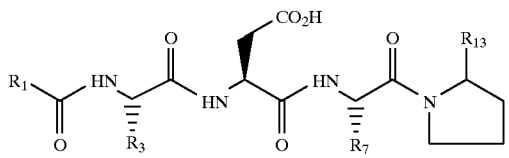

where $R_1$ is a $R_1$ ring structure, lower alkyl, or lower amino alkyl. The $R_1$ ring structure is connected by a spacer 0 to about 5 atoms long forming from one or more N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or-non-aromatic cyclic or heterocyclic ring group wherein the heteroatom is a nitrogen atom. The $R_7$ ring structure can optionally be substituted by an alcohol, nitro or lower alkyl ether group.

$R_{13}$ is a lower alkyl carboxamide, lower alkyl alcohol, carboxylic acid, or H group.

A contemplated compound also corresponds to a prodrug compound corresponding to the following structural formula:

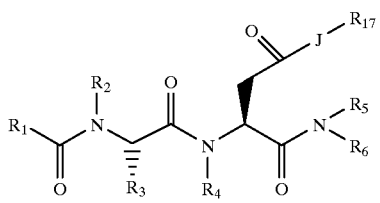

where J is a nitrogen, oxygen, or sulfur atom.

$R_{17}$ forms or is an alkyl ester, alkyl carboxylic ester, alkyl carboxamide carboxylic ester, phenyl alkyl, alkyl carboxamide, alkyl carboxylic acid, alkyl phosphonate, or biotin group.

$R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_5$ is H or $R_5$ and $R_6$ form a $R_5$ ring structure. The $R_5$ ring structure is a fused 6,6- ring structure and can be aromatic, partially saturated, or saturated.

$R_6$ is a benzyl, or 1,1 diphenylmethine group, the $R_5$ ring structure, a group of the formula

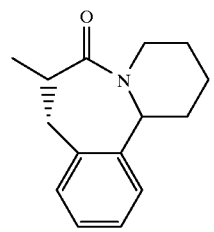

or a group of the formula

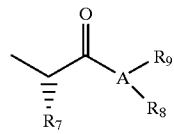

where A is nitrogen or oxygen and, when A is nitrogen, $R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$ the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

When A is oxygen, $R_8$ is a lower alkyl that can be branched and $R_9$ is absent.

A contemplated composition corresponds to an above-described compound and a pharmaceutically acceptable carrier.

A contemplated method corresponds to a method of treating inflammation, asthma and cardiovascular disease by administering an above-described compound.

The present invention has several benefits and advantages.

One salient benefit is that an inhibitor compound contemplated here inhibits the VLA-4 binding interaction with CS-1.

Another benefit of the invention is the compounds have been shown to be effective in reducing various exemplary immunoinflammation disease states in host mammals.

Another advantage of the invention is that a contemplated inhibitor compound is a relatively small molecule that is easily prepared in high yield and purity.

Still further benefits and advantages of the invention will become apparent to the skilled worker from the disclosure that follows.

BRIEF DESCRIPTION OF THE DRAWINGS

In the drawings forming a portion of this disclosure:

FIG. 4 shown in two panels as FIG. 4A

FIG. 4B shows results obtained for the percent change in lung resistance ($L_R$) from the same study, with data being presented as in FIG. 4A. The ordinate is in units of percent change from the original lung resistance value, whereas the abscissa is in hours.

FIG. 5 is a graph showing the results of a study of the effect of the inhibitor compound N-phenyl acetyl-Leu-Asp-Phe-D-Pro-$NH_2$ on delayed type hypersensitivity measured in ears of 14 mice. After immunization, one group of seven mice was treated with only a saline solution provided by an implanted pump over a 24-hour time period and challenged. The other immunized group of seven mice was similarly challenged, but each was treated with an aqueous pharmaceutical composition containing the above inhibitor compound for the same 24-hour time period, also supplied by implanted pumps. The ordinate is in units of inches of swelling diameter at the challenge site.

DETAILED DESCRIPTION OF THE INVENTION

Figure 1:
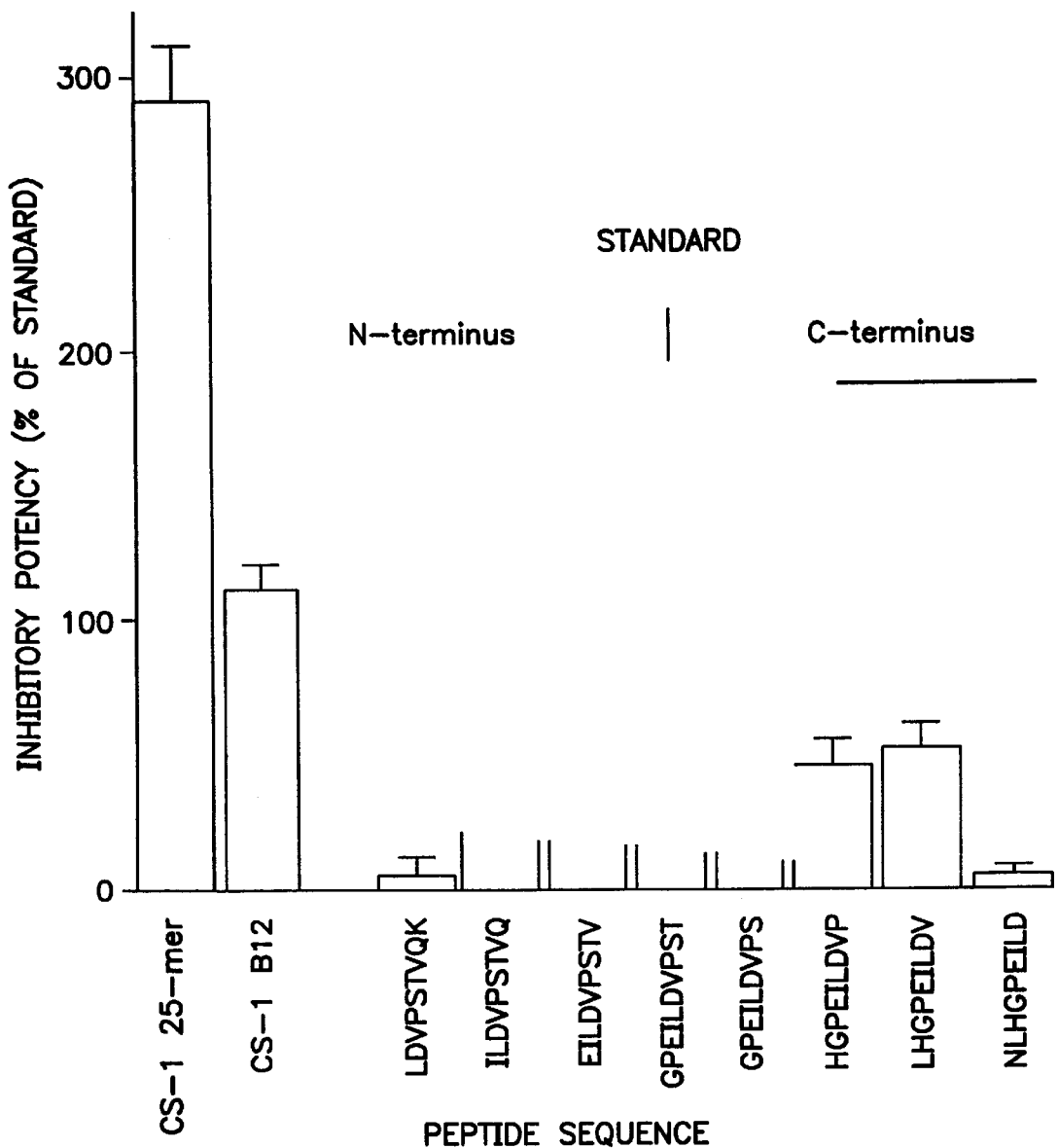
FIG. 1 is a graph illustrating the in vitro binding inhibition of VLA-4-bearing Jurkat cells to the solid phase-bound CS-1 compound (SEQ ID NO:1) by that compound itself and shorter compounds having portions of the CS-1 compound sequence. Data are shown as percentages relative to the indicated "Standard" (SEQ ID NO:3). Data for compounds with deletions at the "N-terminus" of compound B12 (SEQ ID NO:2) are shown to the left of the Standard, and data for compounds with deletions at the "C-terminus" of compound B12 are shown to the right of the standard. Compound sequences are in single letter code.

The present invention contemplates a compound, a prodrug compound, a composition containing such a compound, and a method of using such a compound. A contemplated compound inhibits binding between the CS-1 of fibronectin and the inflammatory cell VLA-4 surface receptor, and is therefore sometimes referred to herein as an inhibitor compound.

A. Compounds

A contemplated compound is a compound that inhibits CS-1 binding to the VLA-4 receptor. Further, a contemplated compound is a prodrug compound that does not necessarily bind the VLA-4 receptor in vitro but is converted in vivo to a compound having such binding activity.

Broadly, a contemplated compound can be defined by the following structural formula:

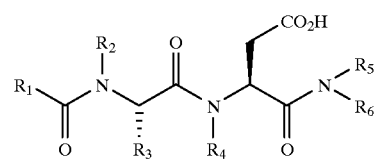

where $R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_5$ is H or $R_5$ and $R_6$ form a $R_5$ ring structure. The $R_5$ ring structure is a fused 6,6- ring structure and can be aromatic, partially saturated, or saturated.

$R_6$ is a benzyl, or 1,1 diphenylmethine group, the $R_5$ ring structure, a group of the formula

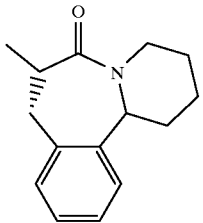

or a group of the formula

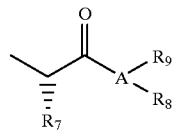

where A is nitrogen or oxygen and, when A is nitrogen, $R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a $R_8$ ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

When A is oxygen, $R_8$ is a lower alkyl that can be branched and $R_9$ is absent.

A contemplated compound can be defined by the following structural formula:

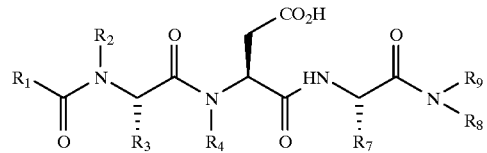

where $R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino)amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

A contemplated compound can be defined by the following structural formula:

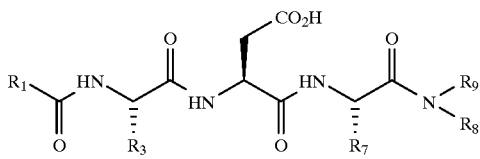

where $R_1$ is a $R_1$ ring structure, lower alkyl, or lower amino alkyl. The $R_1$ ring structure is connected by a spacer 0 to about 5 atoms long forming from one or more alkyl, N-amido, N-sulfonimido, N-urea, N-carboxyl groups optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

A contemplated compound can be defined by the following structural formula:

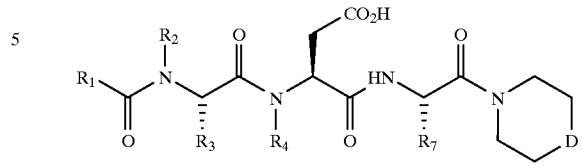

where D is a carbon, nitrogen, oxygen, or sulfur atom optionally substituted by or forming a lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido group.

$R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

A contemplated compound can be defined by the following structural formula:

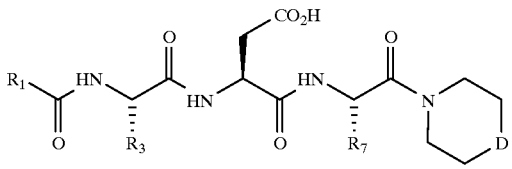

where D is a carbon, nitrogen, oxygen, or sulfur atom optionally substituted by or forming a lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido group.

$R_1$ is a $R_1$ ring structure, lower alkyl, or lower amino alkyl. The $R_1$ ring structure is connected by a spacer 0 to about 5 atoms long forming from one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

The compound of the formula immediately above wherein D is a nitrogen atom optionally substituted by or forming a lower alkyl, amine lower alkyl, carboxamide, alcohol, lower alkyl alcohol, lower hydroxy alkyl ether, carboxylic acid, lower alkyl carboxylic acid or alkyl substituted phenyl sulfonamido group; $R_1$ is a lower alkyl or lower amino alkyl group, or 6-membered aromatic ring structure connected by a lower alkyl group; $R_3$ is a lower alkyl, lower alkyl alcohol, or lower thioalkyl group or cyclohexane connected by an alkyl group 0 to about 3 carbon atoms long; $R_3$ is a lower alkyl, lower alkyl alcohol, or lower thioalkyl group or 6-membered aromatic ring structure connected by an alkyl group 0 to about 3 carbon atoms long; and the lower alkyl, lower alkyl alcohol or lower thioalkyl group can be branched.

The compound of the formula immediately above wherein D is a carbon atom optionally substituted by or forming a lower alkyl, amine lower alkyl, carboxamide, alcohol, lower alkyl alcohol, lower hydroxy alkyl ether, carboxylic acid, lower alkyl carboxylic acid or alkyl substituted phenyl sulfonamido group; $R_1$ is a lower alkyl or lower amino alkyl group, or 6-membered aromatic ring structure connected by a lower alkyl group; $R_3$ is a lower alkyl, lower alkyl alcohol, or lower thioalkyl group or cyclohexane connected by an alkyl group 0 to about 3 carbon atoms long; $R_3$ is a lower alkyl, lower alkyl alcohol, or lower thioalkyl group or 6-membered aromatic ring structure connected by an alkyl group 0 to about 3 carbon atoms long; and the lower alkyl, lower alkyl alcohol or lower thioalkyl group can be branched.

The compound of the formula immediately above wherein D is a oxygen atom; $R_1$ is a lower alkyl or lower amino alkyl group, or 6-membered aromatic ring structure connected by a lower alkyl group; $R_3$ is a lower alkyl, lower alkyl alcohol, or lower thioalkyl group or cyclohexane connected by an alkyl group 0 to about 3 carbon atoms long; $R_3$ is a lower alkyl, lower alkyl alcohol, or lower thioalkyl group or 6-membered aromatic ring structure connected by an alkyl group 0 to about 3 carbon atoms long; and the lower alkyl, lower alkyl alcohol or lower thioalkyl group can be branched.

The compound of the formula immediately above wherein D is a sulfur atom optionally substituted by or forming a lower alkyl, amine lower alkyl, carboxamide, alcohol, lower alkyl alcohol, lower hydroxy alkyl ether, carboxylic acid, lower alkyl carboxylic acid or alkyl substituted phenyl sulfonamido group; $R_1$ is a lower alkyl or lower amino alkyl group, or 6-membered aromatic ring structure connected by a lower alkyl group; $R_3$ is a lower alkyl, lower alkyl alcohol, or lower thioalkyl group or cyclohexane connected by an alkyl group 0 to about 3 carbon atoms long; $R_3$ is a lower alkyl, lower alkyl alcohol, or lower thioalkyl group or 6-membered aromatic ring structure connected by an alkyl group 0 to about 3 carbon atoms long; and the lower alkyl, lower alkyl alcohol or lower thioalkyl group can be branched.

A contemplated compound can be defined by the following structural formula:

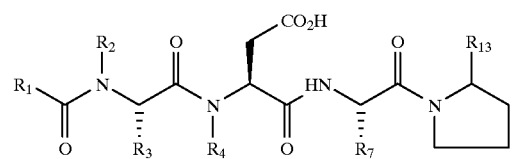

where $R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{13}$ is a formamide, lower alkyl carboxamide, lower alkyl alcohol, carboxylic acid, or H group.

A contemplated compound can be defined by the following structural formula:

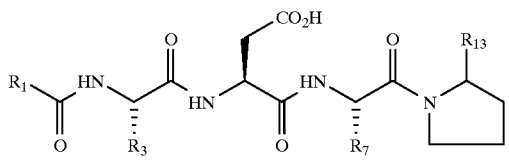

where $R_1$ is a $R_1$ ring structure, lower alkyl, or lower amino alkyl. The $R_1$ ring structure is connected by a spacer 0 to about 5 atoms long forming from one or more N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{13}$ is a lower alkyl carboxamide, lower alkyl alcohol, carboxylic acid, or H group.

A contemplated compound is of the formula immediately above wherein $R_1$ is a lower alkyl or lower amino alkyl group or a 6-membered aromatic ring structure connected by a lower alkyl group; $R_3$ is a lower alkyl, lower alkyl alcohol or lower thioalkyl group or a cyclohexane connected by an alkyl group 0 to about 3 carbon atoms long; $R_7$ is a lower alkyl, lower alkyl alcohol, or lower thioalkyl group or a 6-membered aromatic ring structure connected by a lower alkyl group; and $R_{13}$ is a lower alkyl carboxamide.

A contemplated compound can be defined by the following structural formula:

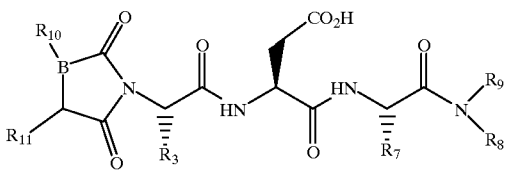

where B is a carbon or nitrogen atom.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is the $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

$R_{10}$ is a H, lower alkyl phenyl group, or $R_{10}$ and $R_{11}$ form a $R_{10}$ ring structure group that is a fused 6- or fused 6,6-membered cyclic or heterocyclic ring wherein the heteroatoms are 1 or 2 nitrogen atoms.

$R_{11}$ is a H, lower alkyl phenyl or the $R_{10}$ ring structure group.

A contemplated compound can be defined by the following structural formula:

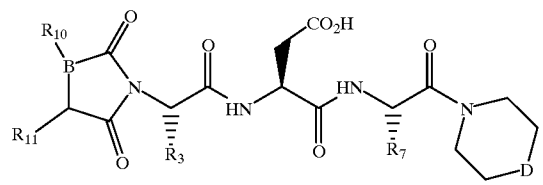

where B is a carbon or nitrogen atom and D is a carbon, nitrogen, oxygen, or sulfur atom optionally substituted by or forming a lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{10}$ is a H, lower alkyl phenyl group, or $R_{10}$ and $R_{11}$ form a $R_{10}$ ring structure group that is a fused 6- or fused 6,6-membered cyclic or heterocyclic ring wherein the heteroatoms are 1 or 2 nitrogen atoms.

$R_{11}$ is a H, lower alkyl phenyl or the $R_{10}$ ring structure group.

A contemplated compound can be defined by the structural formula immediately above wherein B is a carbon atom and the $R_{10}$ ring structure group forms a phthalimido group.

A contemplated compound can be defined by the following structural formula:

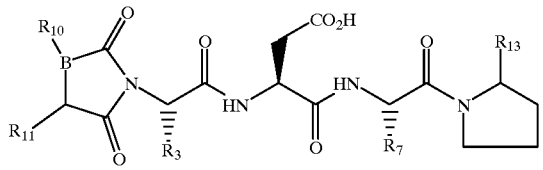

where B is a carbon or nitrogen atom.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{10}$ is a H, lower alkyl phenyl group, or $R_{10}$ and $R_{11}$ form a $R_{10}$ ring structure group that is a fused 6- or fused 6,6-membered cyclic or heterocyclic ring wherein the heteroatoms are 1 or 2 nitrogen atoms.

$R_{11}$ is a H, lower alkyl phenyl or the $R_{10}$ ring structure group.

$R_{13}$ is a formamide, lower alkyl carboxamide, lower alkyl alcohol, carboxylic acid, or H group.

A contemplated compound can be defined by the structural formula immediately above wherein B is a carbon atom and the $R_{10}$ ring structure group forms a phthalimido group.

A contemplated compound can be defined by the following structural formula:

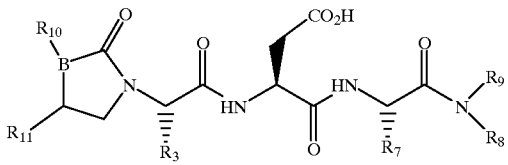

where B is a carbon or nitrogen atom.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7- membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is the $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino)amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

$R_{10}$ is a H, lower alkyl phenyl group, or $R_{10}$ and $R_{11}$ form a $R_{10}$ ring structure group that is a fused 6- or fused 6,6-membered cyclic or heterocyclic ring wherein the heteroatoms are 1 or 2 nitrogen atoms.

$R_{11}$ is a H, lower alkyl phenyl or the $R_{10}$ ring structure group.

A contemplated compound can be defined by the following structural formula:

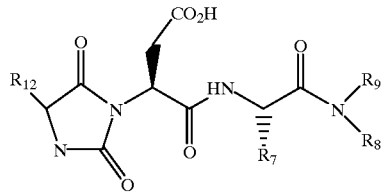

where $R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7-membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is the $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino)

amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower alkyl carboxamide, lower alkyl morpholine amide, cyclohexane or H group.

$R_{12}$ is a $R_{12}$ ring structure or lower alkyl group. The $R_{12}$ ring structure is a 6-membered cyclic or heterocyclic ring wherein the heteroatoms are one or two nitrogen atoms and can be connected by an alkyl group 0 to 3 atoms long. The lower alkyl group can be branched.

A contemplated compound corresponds to the following structural formula:

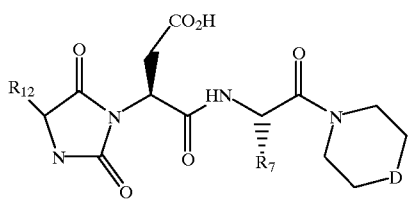

where D is a carbon, nitrogen, oxygen, or sulfur atom optionally substituted by or forming a lower alkyl, amine lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido group.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{12}$ is a $R_{12}$ ring structure or lower alkyl group. The $R_{12}$ ring structure is a 6-membered cyclic or heterocyclic ring wherein the heteroatoms are one or two nitrogen atoms and can be connected by an alkyl group 0 to 3 atoms long. The lower alkyl group can be branched.

A contemplated compound corresponds to the following structural formula:

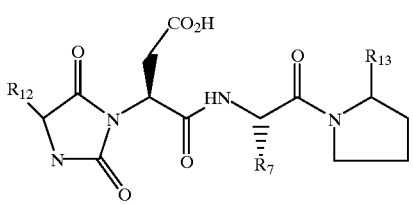

where $R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

$R_{12}$ is a $R_{12}$ ring structure or lower alkyl group. The $R_{12}$ ring structure is a 6-membered cyclic or heterocyclic ring wherein the heteroatoms are one or two nitrogen atoms and can be connected by an alkyl group 0 to 3 atoms long. The lower alkyl group can be branched.

$R_{13}$ is a formamide, lower alkyl carboxamide, lower alkyl alcohol, carboxylic acid, or H group.

A contemplated compound corresponds to the following structural formula:

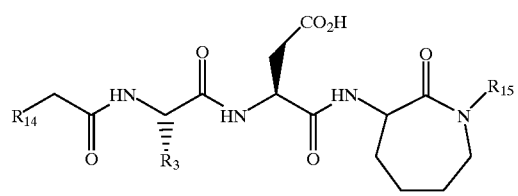

where $R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_{14}$ is a 6-membered aromatic cyclic or heterocyclic ring wherein the heteroatom is a nitrogen atom.

$R_{15}$ is lower alkyl carboxamide or H group.

A contemplated compound corresponds to the following structural formula:

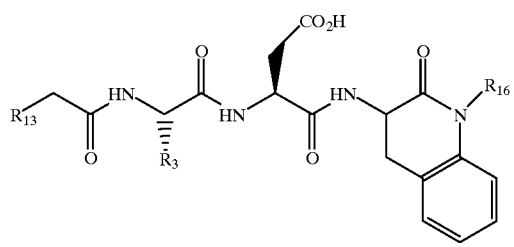

where $R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_{14}$ is a 6-membered aromatic cyclic or heterocyclic ring wherein the heteroatom is a nitrogen atom.

$R_{16}$ is a lower alkyl, lower alkyl morpholine amide, or H group wherein the lower alkyl can be branched.

Table 1 provides the structural formula of exemplary compounds along with their binding inhibition potencies relative to the standard compound of SEQ ID NO:3, assigned a relative potency of 1. The compound ID number of Table 1 cross-references individual compounds herein.

TABLE 1

Compound Structure and Potency

| Structure | Compound ID Number | Relative Potency |
|---|---|---|
| [Phenylacetyl-Leu-Asp-Phe-piperazinyl-CH₂COOH structure] | 1111.06 | 2600 |
| [Phenylacetyl-Leu-Asp-Phe-thiomorpholine-SO₂ structure] | 1111.03 | 1010 |
| [Phenylacetyl-Leu-Asp-Phe-piperazinyl-CH₂CH₂COOH structure] | 1190.03 | 998 |
| [Phenylacetyl-Leu-Asp-Phe-piperidinyl-CONH₂ structure] | 1111.05 | 942 |
| [Phenylacetyl-Leu-Asp-Phe-piperidinyl-COOH structure] | 1111.04 | 836 |

TABLE 1-continued

Compound Structure and Potency

| Structure | Compound ID Number | Relative Potency |
|---|---|---|
| [structure] | 1051.01 | 709 |
| [structure] | 896.61 | 612 |
| [structure] | 1070.02 | 604 |
| [structure] | 1190.02 | 591 |
| [structure] | 1111.07 | 510 |

TABLE 1-continued

Compound Structure and Potency

| Structure | Compound ID Number | Relative Potency |
|---|---|---|
| (structure) | 1051.02 | 507 |
| (structure) | 1111.02 | 450 |
| (structure) | 1036.01 | 405 |
| (structure) | 951.22 | 387 |
| (structure) | 1111.01 | 363 |

TABLE 1-continued
Compound Structure and Potency
| Structure | Compound ID Number | Relative Potency |
|---|---|---|
| 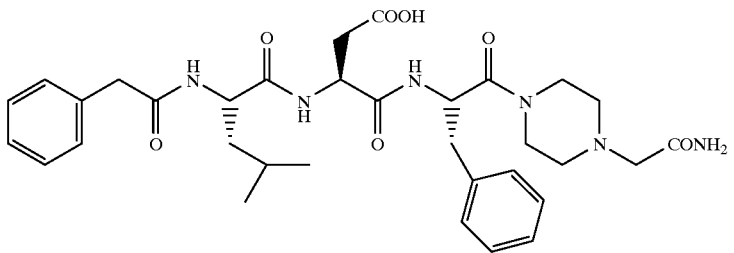 | 1111.09 | 324 |
| 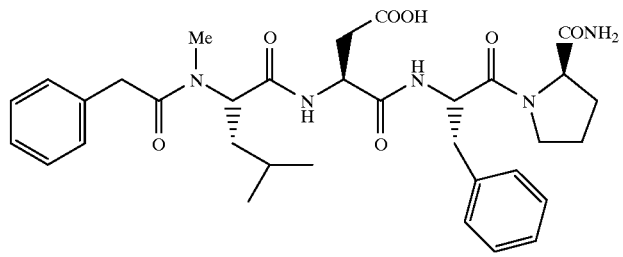 | 1190.07 | 318 |
| 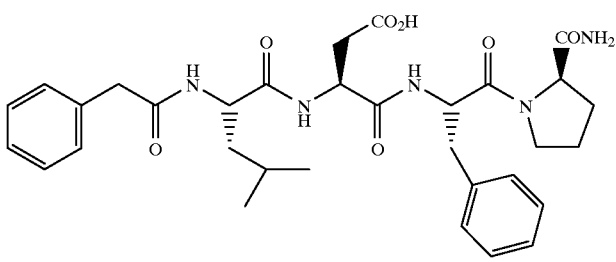 | 896.52 | 313 |
| 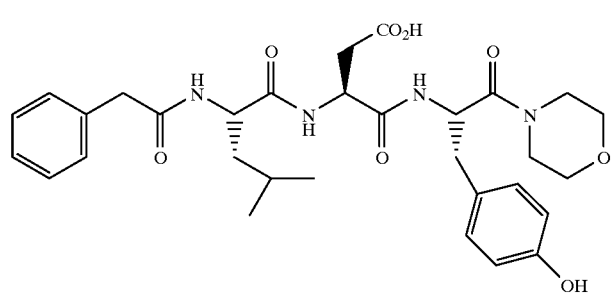 | 1045.02 | 313 |
| 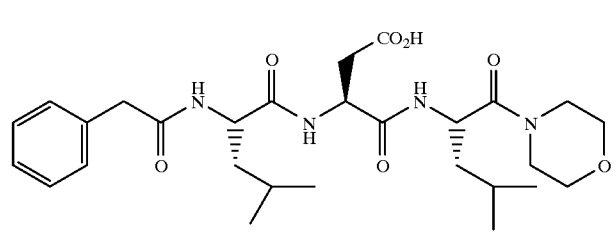 | 997.20 | 291 |

TABLE 1-continued

Compound Structure and Potency

| Structure | Compound ID Number | Relative Potency |
|---|---|---|
| 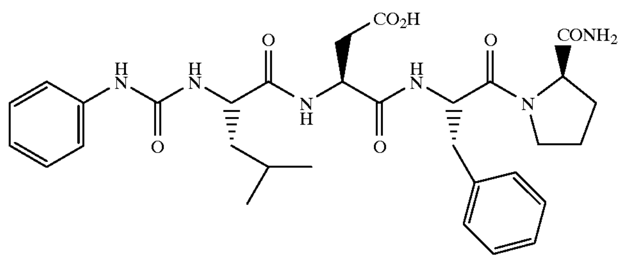 | 896.62 | 257 |
| 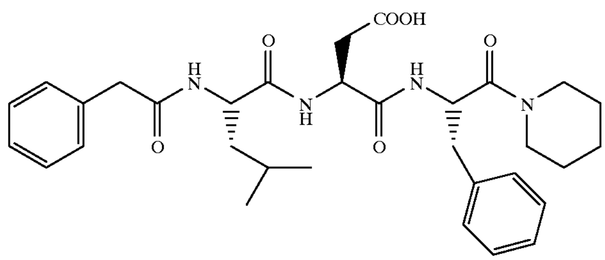 | 951.14 | 239 |
| 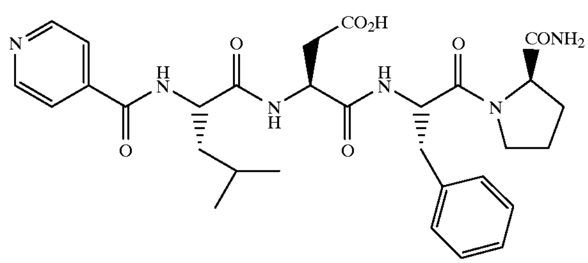 | 951.20 | 228 |
| 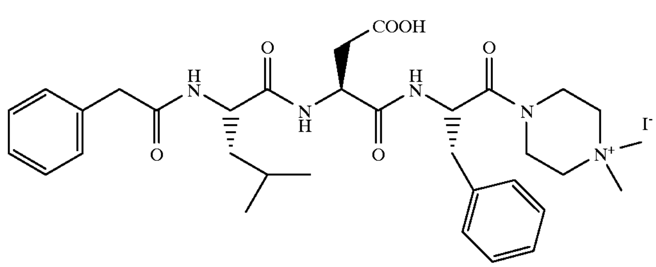 | 1111.08 | 218 |
| 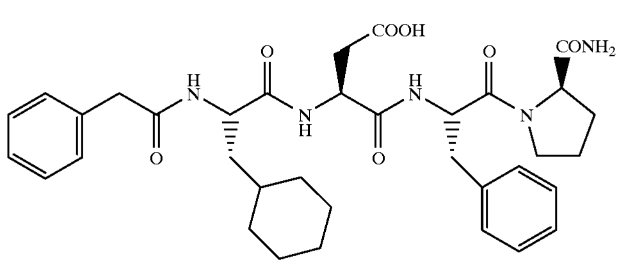 | 1160.01 | 213 |

TABLE 1-continued
Compound Structure and Potency
| Structure | Compound ID Number | Relative Potency |
|---|---|---|
| 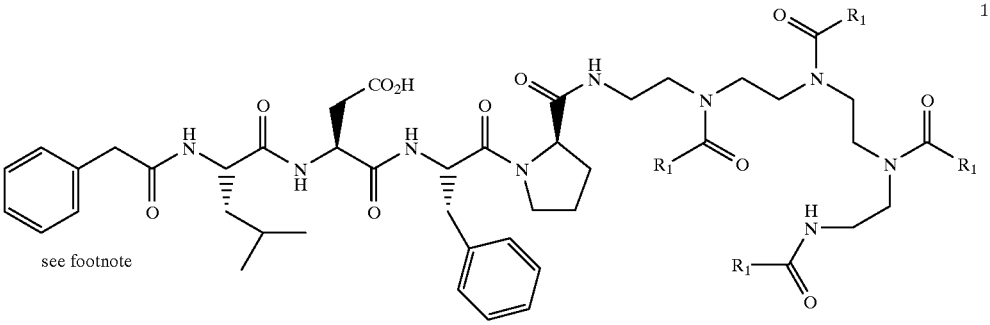 see footnote | 1058.01 | 210 |
| 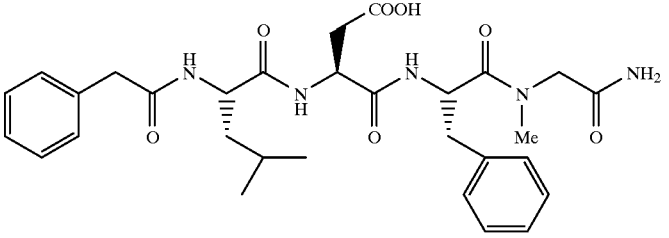 | 1190.04 | 196 |
| 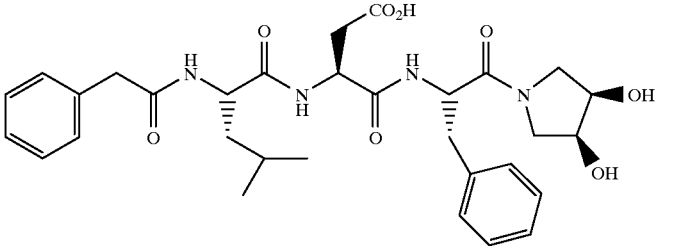 | 1070.01 | 194 |
| 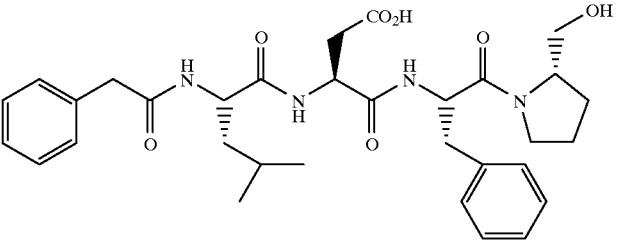 | 951.17 | 163 |
| 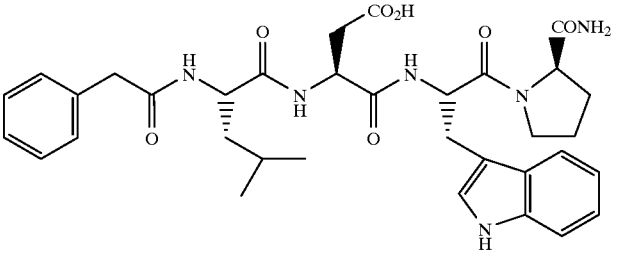 | 896.60 | 131 |

TABLE 1-continued

Compound Structure and Potency

| Structure | Compound ID Number | Relative Potency |
|---|---|---|
| (structure) | 951.15 | 121 |
| (structure) see footnote | 1092.01 | 118 |
| (structure) | 896.51 | 110 |
| (structure) | 896.55 | 105 |
| (structure) | 1111.10 | 98.9 |

TABLE 1-continued
Compound Structure and Potency
| Structure | Compound ID Number | Relative Potency |
|---|---|---|
| 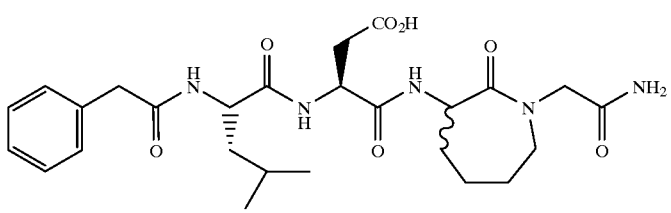 | 1057.06 | 97 |
| 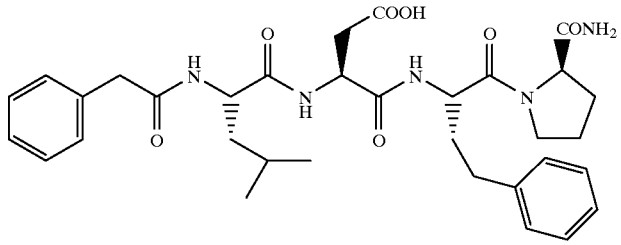 | 1062.03 | 93.9 |
| 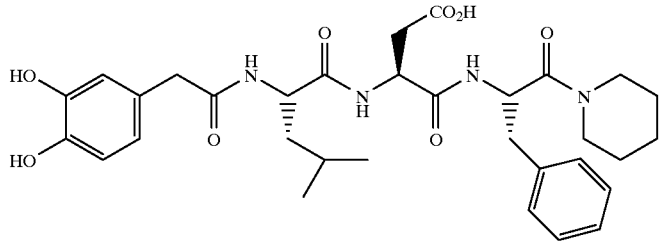 | 1019.01 | 81.4 |
| 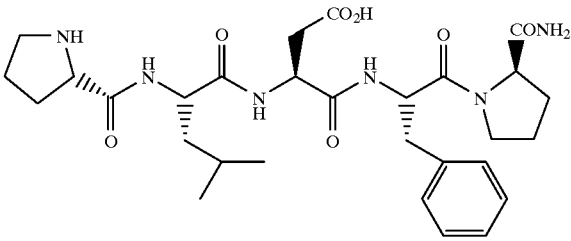 | 951.12 | 61.8 |
| 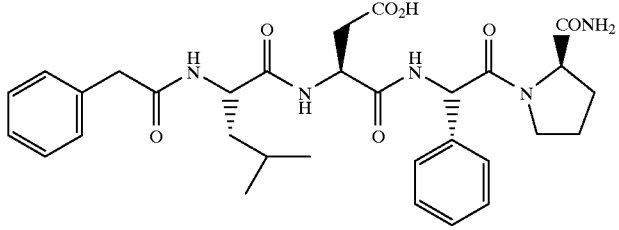 | 896.69 | 61 |

TABLE 1-continued

Compound Structure and Potency

| Structure | Compound ID Number | Relative Potency |
|---|---|---|
| 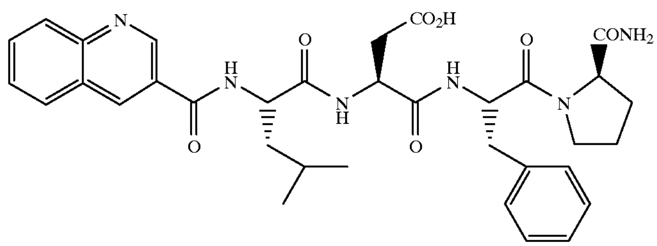 | 951.05 | 56.3 |
| 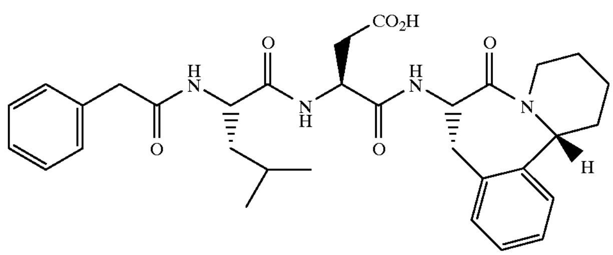 | 1026.05 | 50.1 |
| 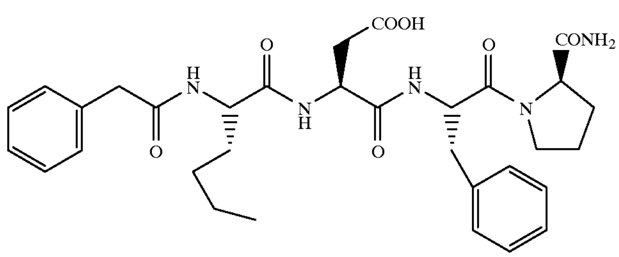 | 1160.02 | 49 |
| 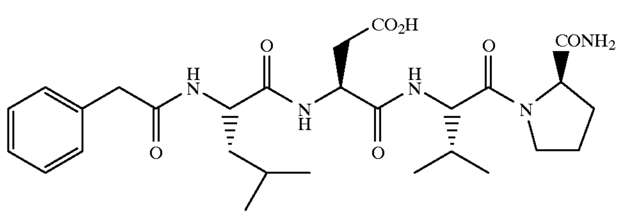 | 896.39 | 47.5 |
| 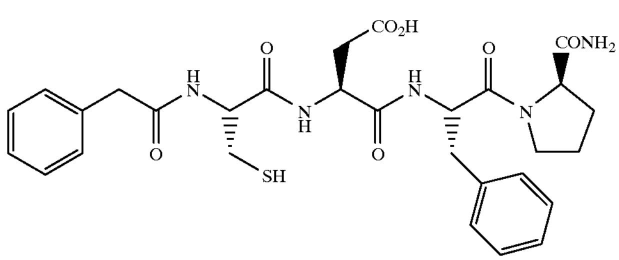 | 1042.22 | 46.9 |

TABLE 1-continued
Compound Structure and Potency
| Structure | Compound ID Number | Relative Potency |
|---|---|---|
| 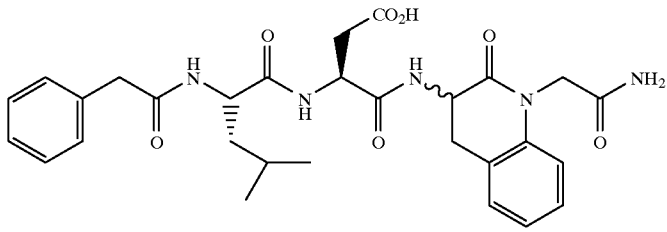 | 997.11 | 44.8 |
| 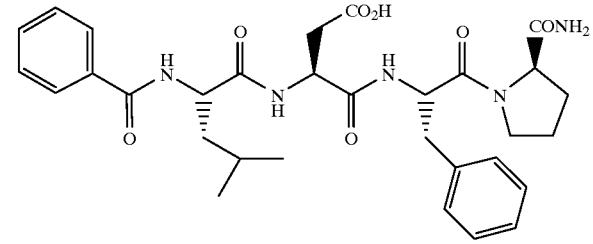 | 896.28 | 44.6 |
| 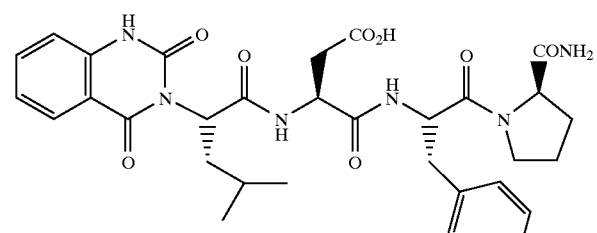 | 896.63 | 43.7 |
| 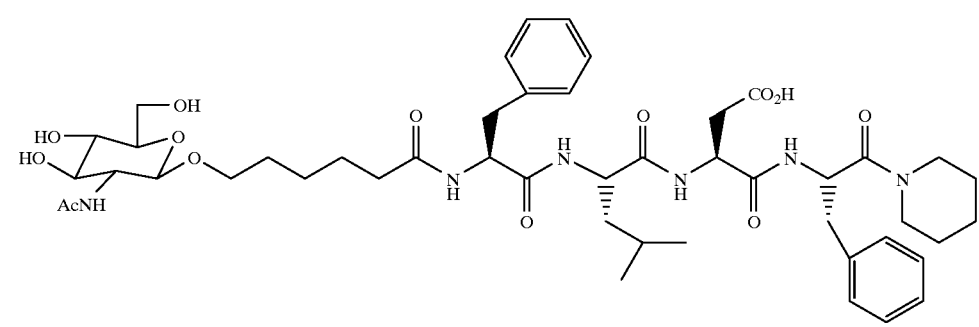 | 1063.01 | 40.7 |
| 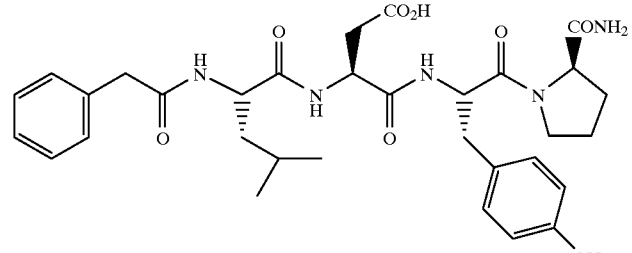 | 896.68 | 39.9 |

TABLE 1-continued
Compound Structure and Potency
| Structure | Compound ID Number | Relative Potency |
|---|---|---|
| 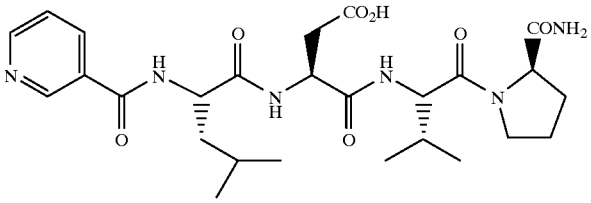 | 896.42 | 38.1 |
| 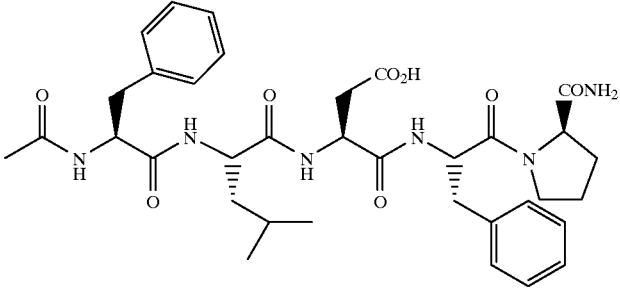 | 951.42 | 35.4 |
| 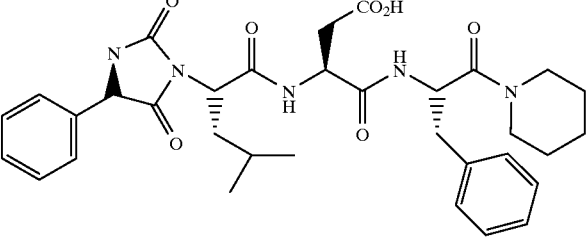 | 1047.01 | 34.4 |
| 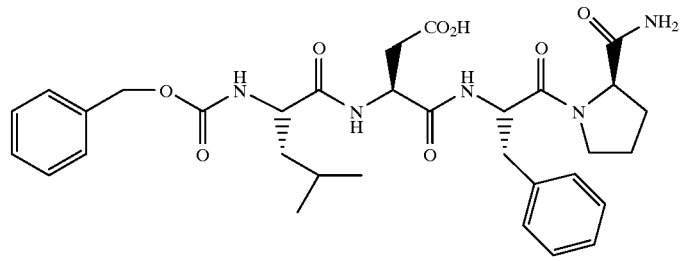 | 1056.01 | 34.4 |
| 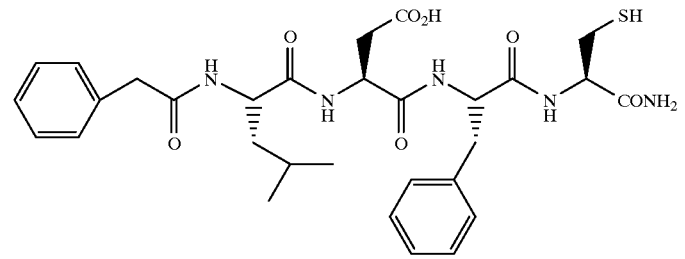 | 1042.23 | 33.2 |

TABLE 1-continued

Compound Structure and Potency

| Structure | Compound ID Number | Relative Potency |
|---|---|---|
| 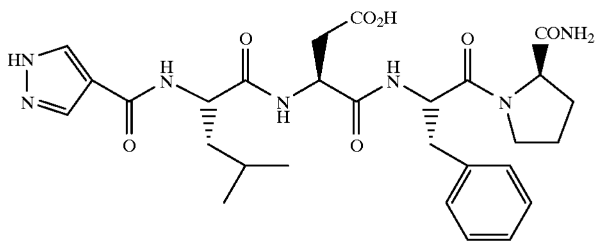 | 951.03 | 28.2 |
| 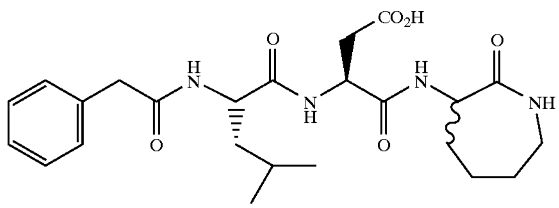 | 1043.02 | 26.8 |
| 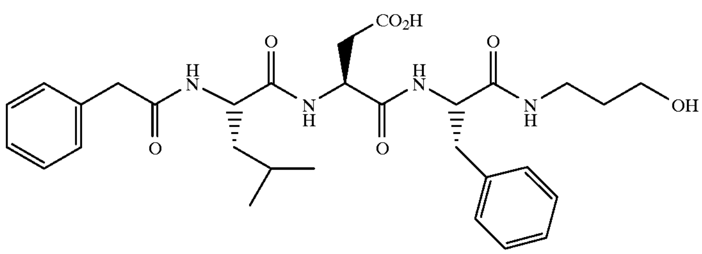 | 1051.05 | 25 |
| 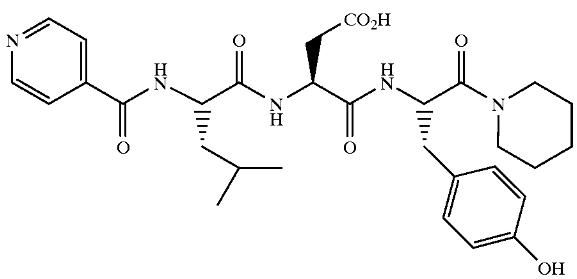 | 1045.01 | 23.8 |
| 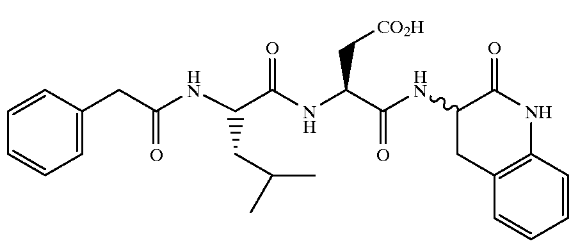 | 997.08 | 23.5 |

TABLE 1-continued

Compound Structure and Potency

| Structure | Compound ID Number | Relative Potency |
|---|---|---|
| 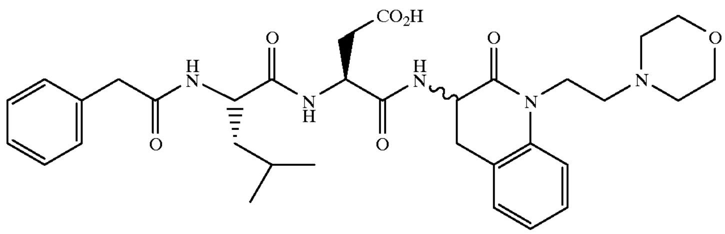 | 997.18 | 20 |
| 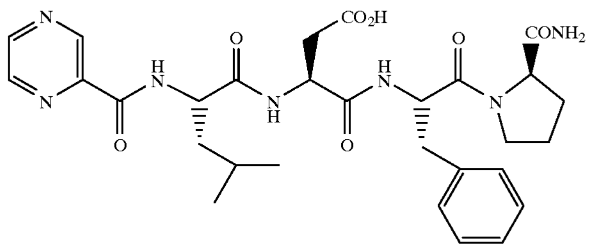 | 951.02 | 19.4 |
| 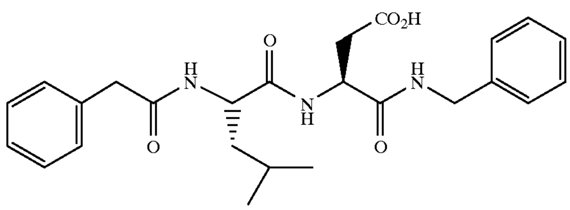 | 997.02 | 18.8 |
| 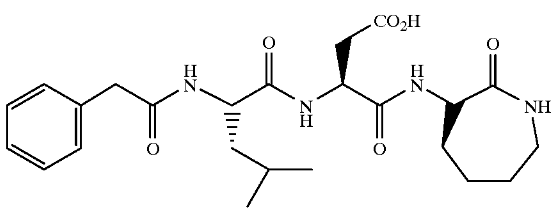 | 1043.01 | 17.2 |
| 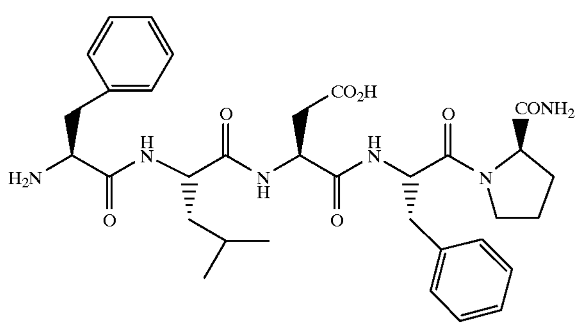 | 896.27 | 16.9 |
| 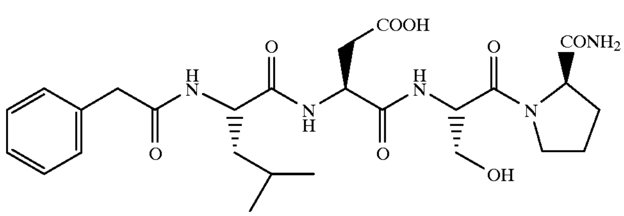 | 896.72 | 16.9 |

TABLE 1-continued
Compound Structure and Potency
| Structure | Compound ID Number | Relative Potency |
|---|---|---|
| 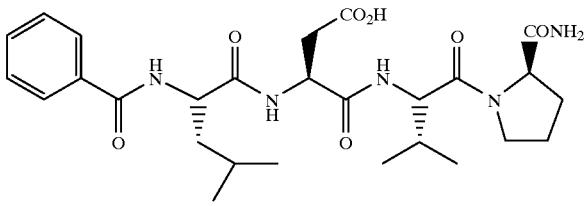 | 896.35 | 16 |
| 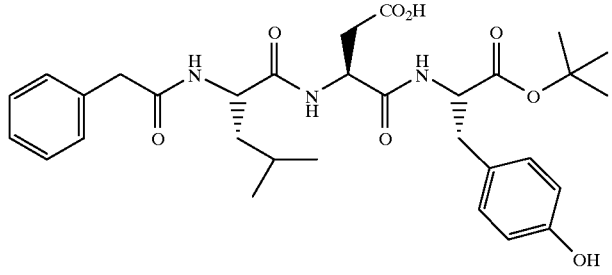 | 1040.02 | 14.7 |
| 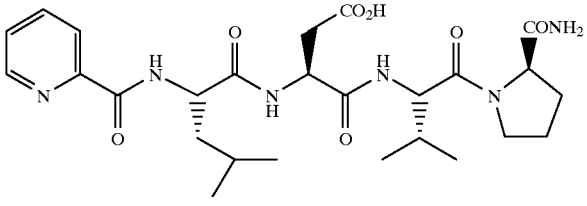 | 896.54 | 13 |
| 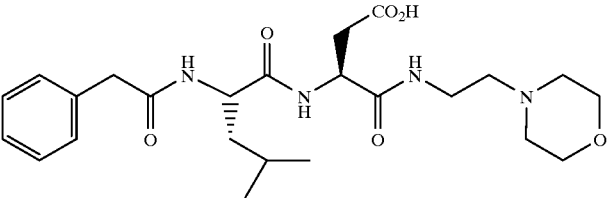 | 997.03 | 12.5 |
| 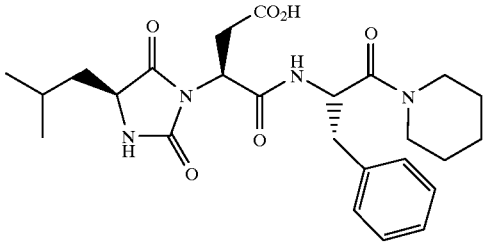 | 1047.05 | 12.5 |

TABLE 1-continued

Compound Structure and Potency

| Structure | Compound ID Number | Relative Potency |
|---|---|---|
| 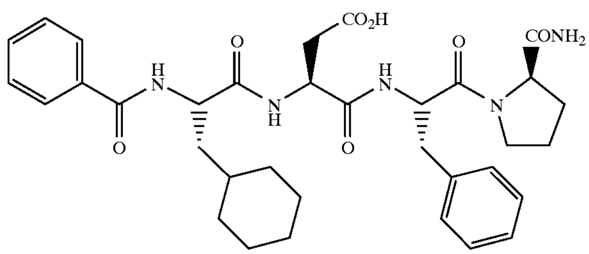 | 896.31 | 11 |
| 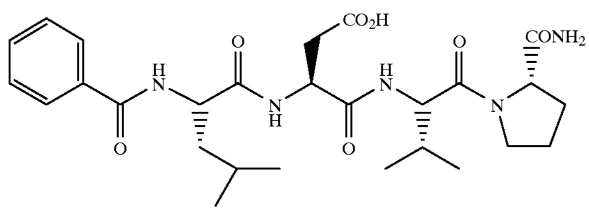 | 926.02 | 9.6 |
| 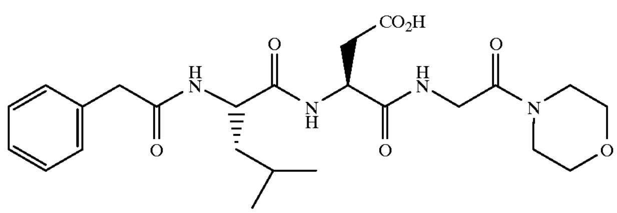 | 997.16 | 9.23 |
| 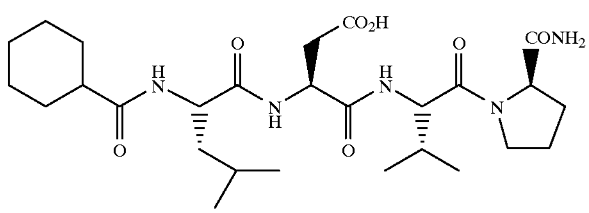 | 896.49 | 9.08 |
| 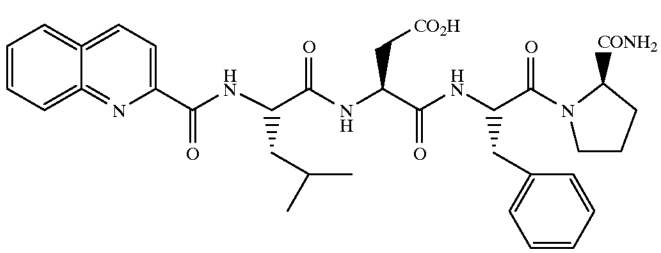 | 951.06 | 8.97 |
| 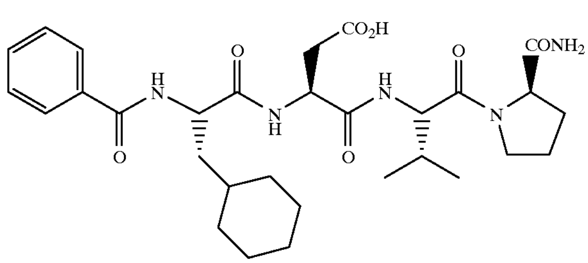 | 896.34 | 6.73 |

TABLE 1-continued
Compound Structure and Potency
| Structure | Compound ID Number | Relative Potency |
|---|---|---|
| 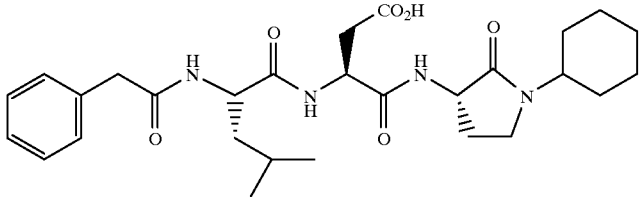 | 1057.02 | 6.57 |
| 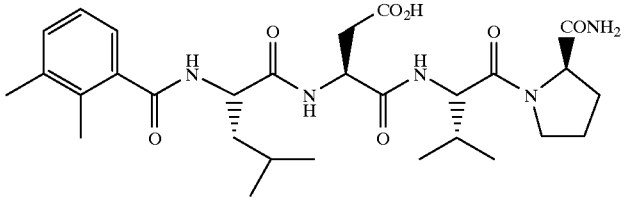 | 896.38 | 6.57 |
| 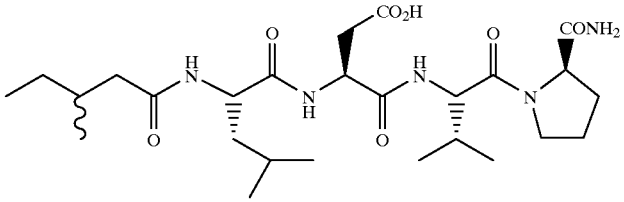 | 896.46 | 6.57 |
| 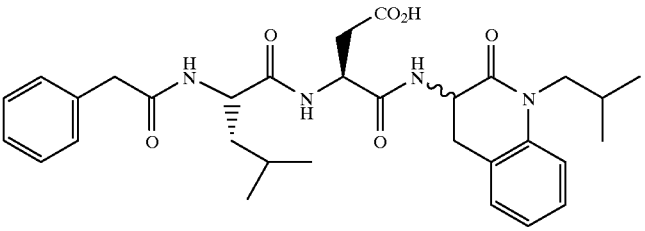 | 997.10 | 6.26 |
| 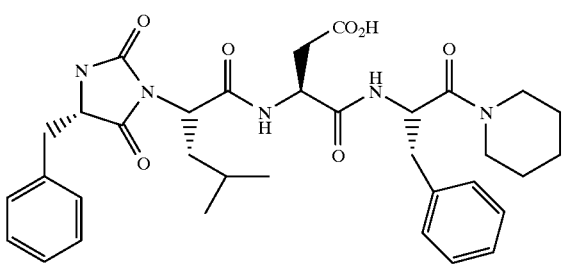 | 1047.06 | 6.26 |
| 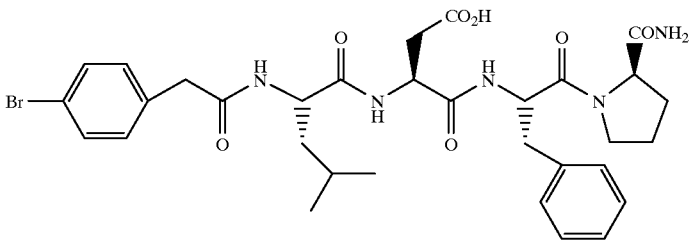 | 951.08 | 6.26 |

TABLE 1-continued
Compound Structure and Potency
| Structure | Compound ID Number | Relative Potency |
|---|---|---|
| 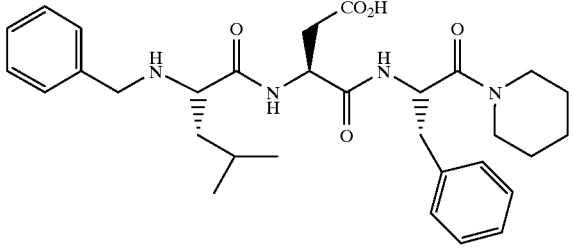 | 1033.01 | 5.84 |
| 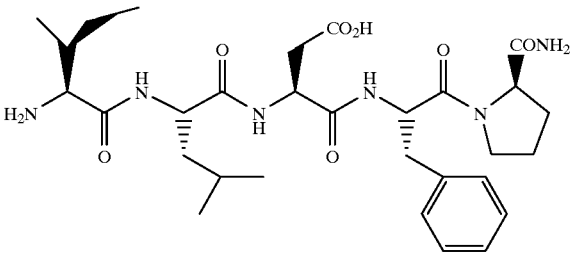 | 896.26 | 5.63 |
| 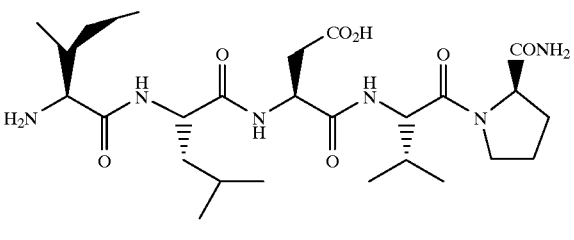 | 886.10 | 5.38 |
| 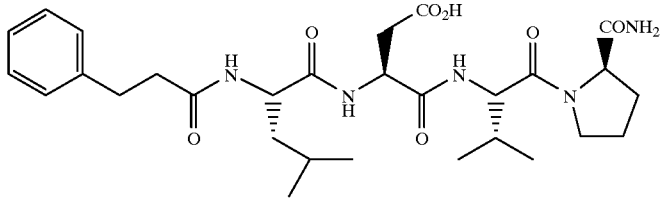 | 896.40 | 5.32 |
| 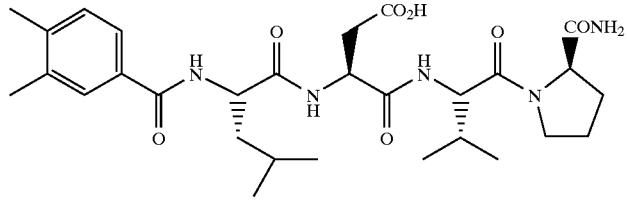 | 896.37 | 5.01 |
| 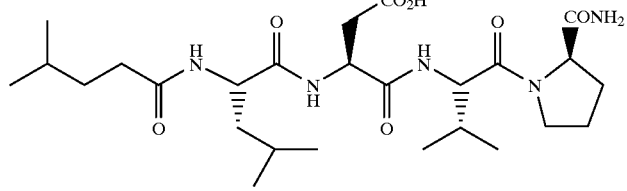 | 896.47 | 5.01 |

TABLE 1-continued
Compound Structure and Potency
| Structure | Compound ID Number | Relative Potency |
|---|---|---|
| 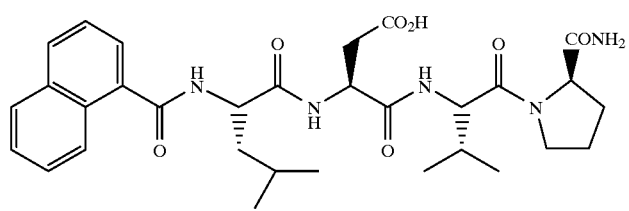 | 896.43 | 4.38 |
| 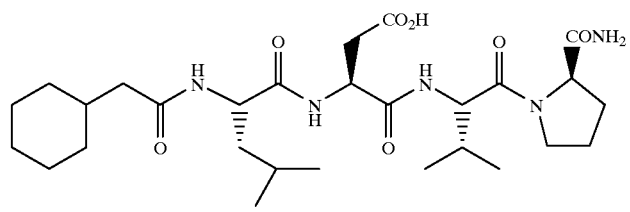 | 896.48 | 3.76 |
| 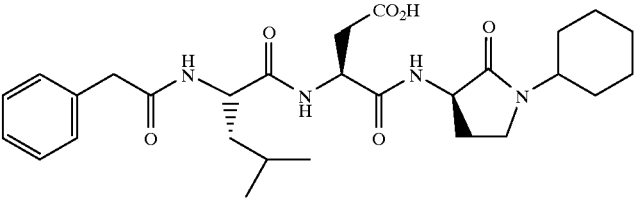 | 1057.03 | 3.44 |
| 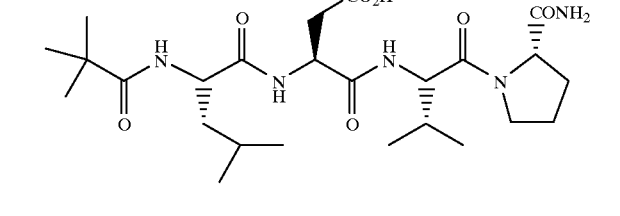 | 926.01 | 3.29 |
| 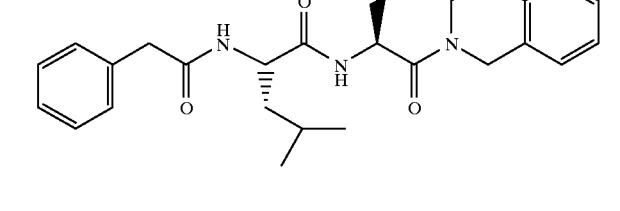 | 997.09 | 3.13 |
| 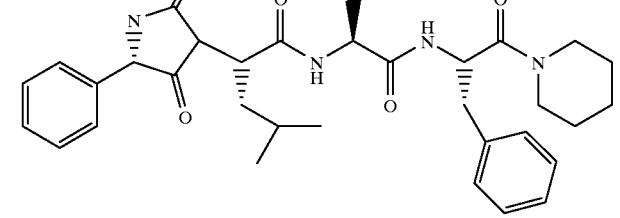 | 1047.02 | 3.13 |

TABLE 1-continued
Compound Structure and Potency
| Structure | Compound ID Number | Relative Potency |
|---|---|---|
| 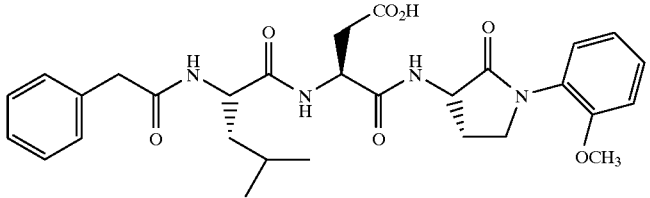 | 1057.04 | 3.13 |
| 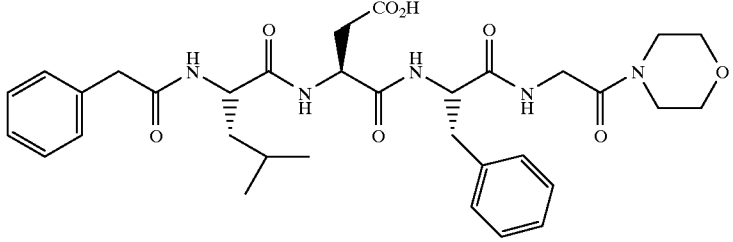 | 1051.04 | 3.13 |
| 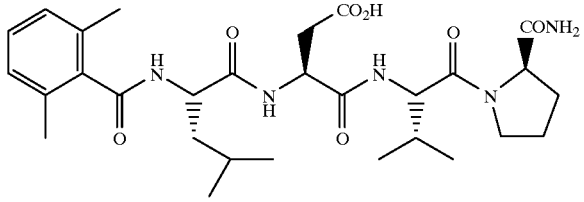 | 896.36 | 3.13 |
| 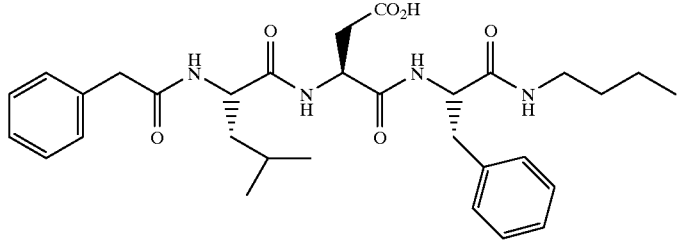 | 1051.03 | 2.82 |
| 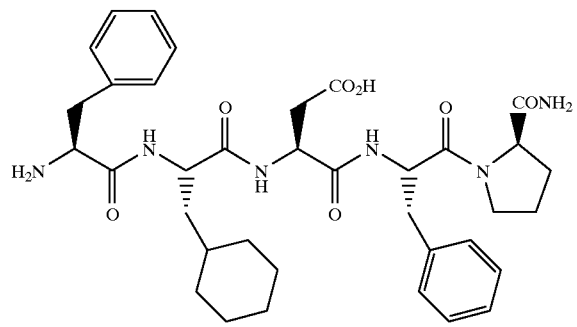 | 896.30 | 2.69 |

TABLE 1-continued

Compound Structure and Potency

| Structure | Compound ID Number | Relative Potency |
|---|---|---|
| 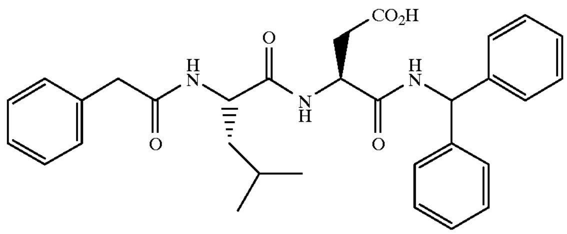 | 997.01 | 2.66 |
| 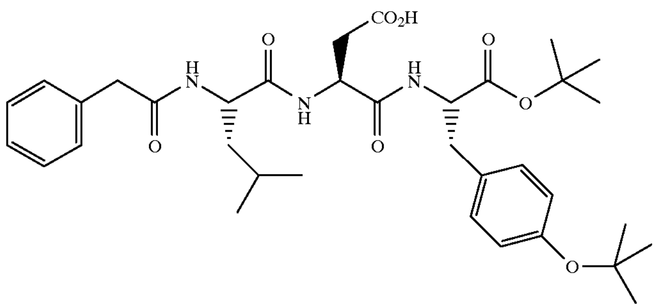 | 1040.01 | 2.66 |
| 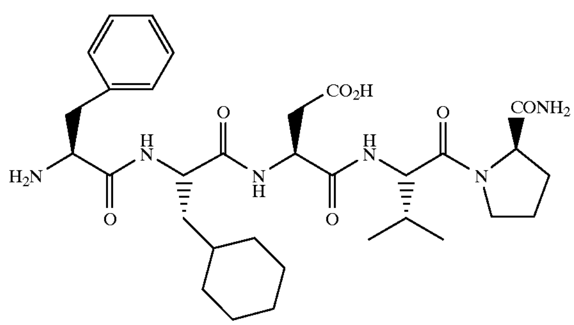 | 896.33 | 2.61 |
| 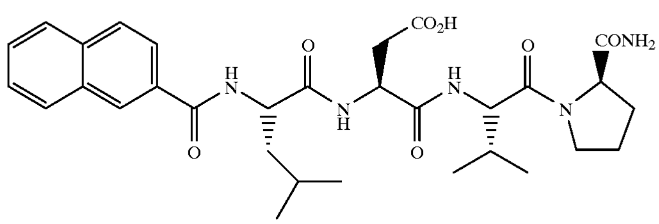 | 896.44 | 2.5 |
| 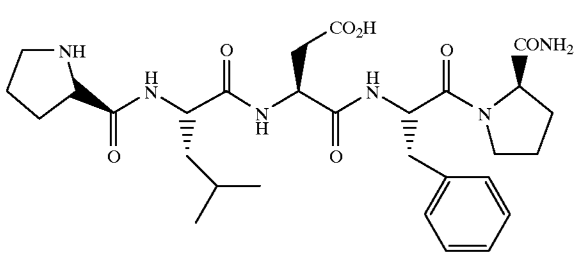 | 951.11 | 2.5 |

TABLE 1-continued
Compound Structure and Potency
| Structure | Compound ID Number | Relative Potency |
|---|---|---|
| 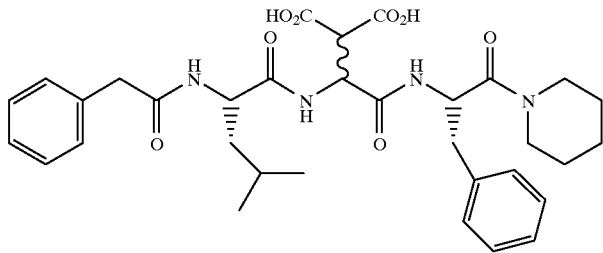 | 1026.04 | 2.32 |
| 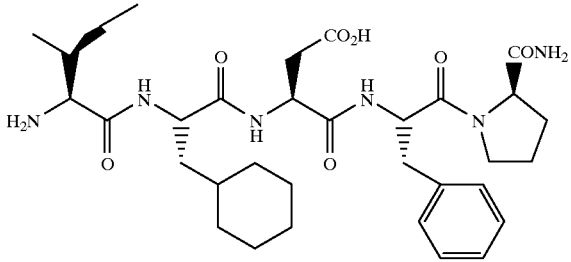 | 896.29 | 2.27 |
| 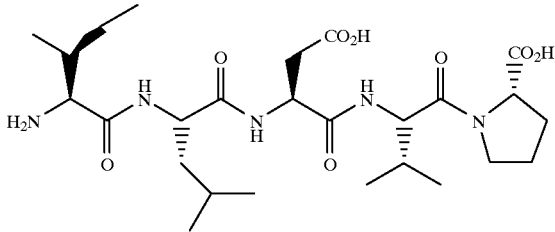 | 886.05 | 2 |
| 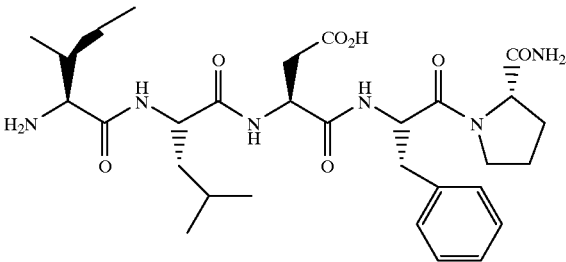 | 926.12 | 1.99 |
| 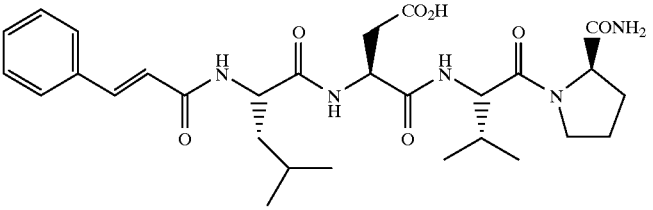 | 896.41 | 1.97 |

TABLE 1-continued

Compound Structure and Potency

| Structure | Compound ID Number | Relative Potency |
|---|---|---|
| [structure] | 1034.01 | 1.96 |
| [structure] | 926.04 | 1.88 |
| [structure] | 926.03 | 1.83 |
| [structure] | 896.45 | 1.75 |
| [structure] | 896.56 | 1.72 |

TABLE 1-continued
Compound Structure and Potency
| Structure | Compound ID Number | Relative Potency |
|---|---|---|
| 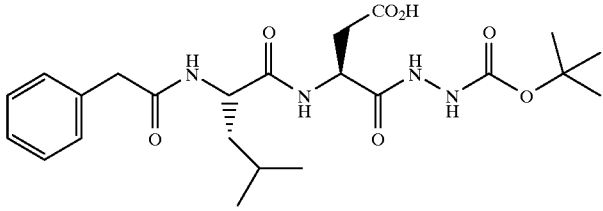 | 997.13 | 1.57 |
| 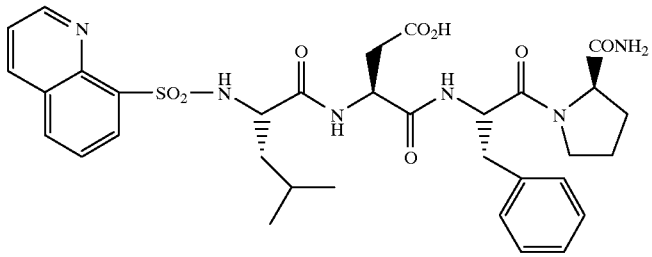 | 951.07 | 1.57 |
| 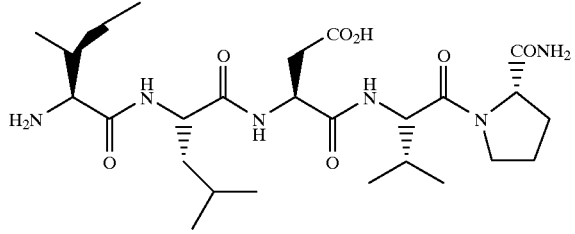 | 886.03 | 1.55 |
| 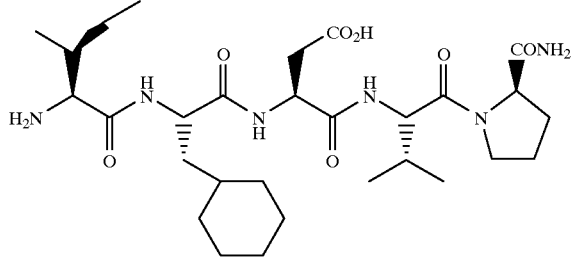 | 896.32 | 1.41 |
| 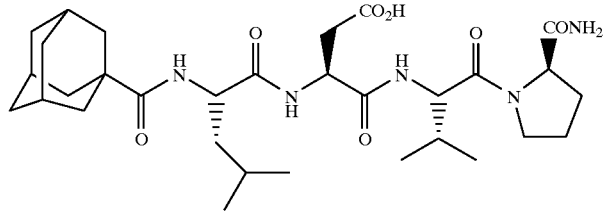 | 896.50 | 1.38 |

TABLE 1-continued

Compound Structure and Potency

| Structure | Compound ID Number | Relative Potency |
|---|---|---|
| 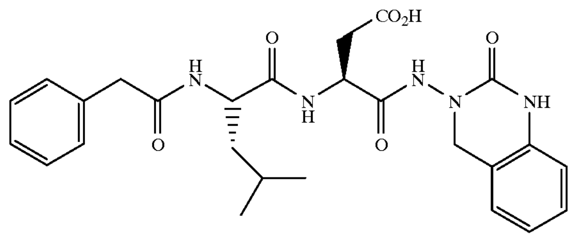 | 997.17 | 1.35 |
| 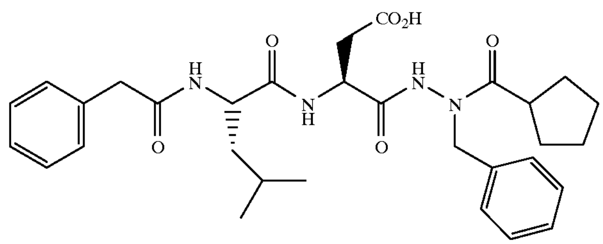 | 997.15 | 1.28 |
| 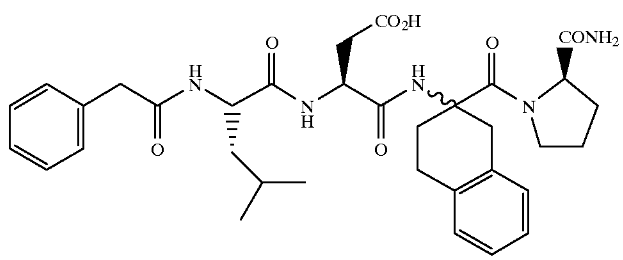 | 896.65 | 1.25 |
| 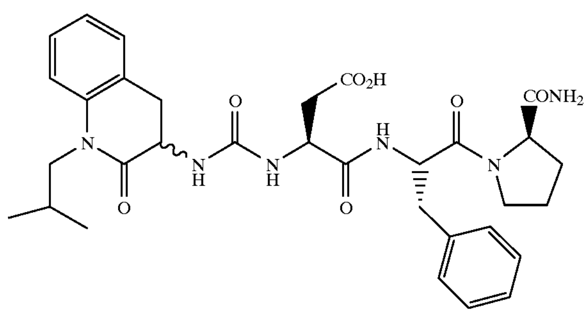 | 1014.01 | 1.22 |
| 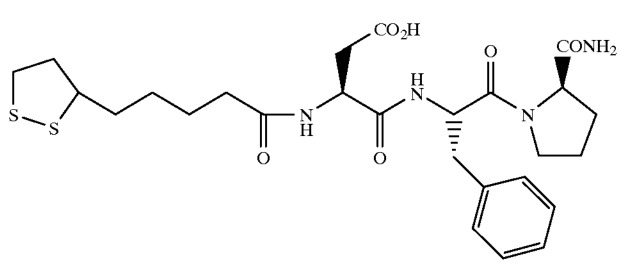 | 1056.09 | 1.1 |

TABLE 1-continued
Compound Structure and Potency
| Structure | Compound ID Number | Relative Potency |
|---|---|---|
| 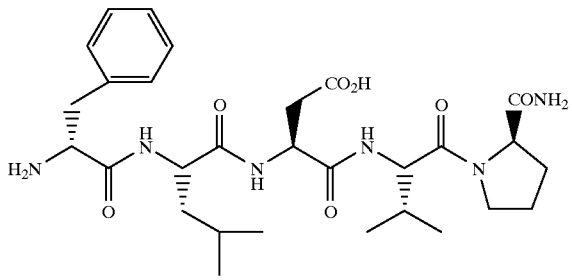 | 926.05 | .94 |
| 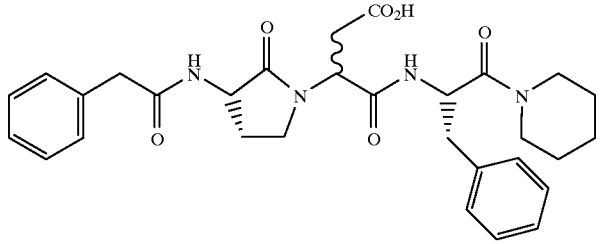 | 1057.01 | .88 |
| 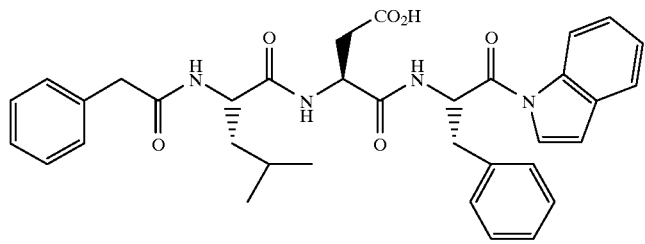 | 951.18 | .78 |
| 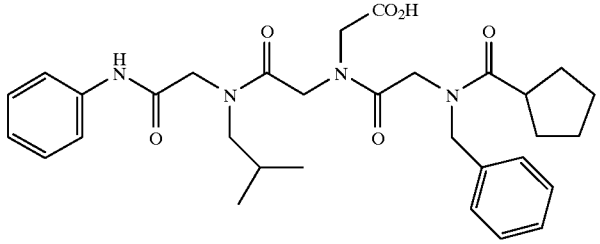 | 1032.02 | .63 |
| 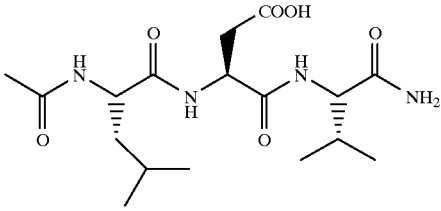 | 926.30 | .63 |

TABLE 1-continued
Compound Structure and Potency
| Structure | Compound ID Number | Relative Potency |
|---|---|---|
| 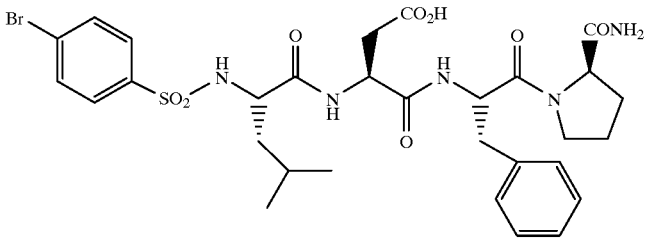 | 951.10 | .63 |
| 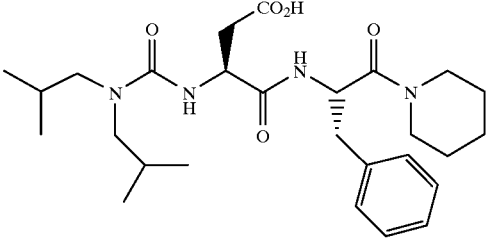 | 1027.01 | .5 |
| 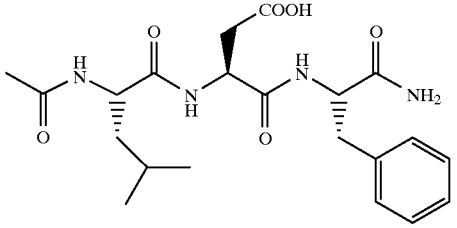 | 926.32 | .47 |
| 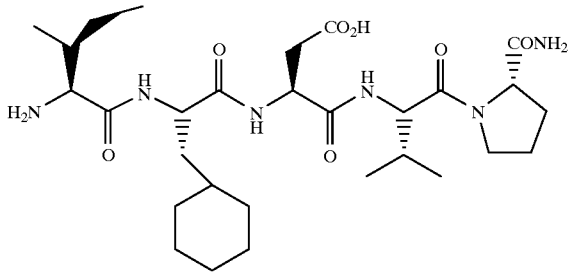 | 926.08 | .47 |
| 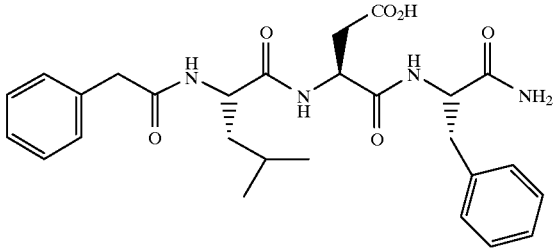 | 997.12 | .48 |

TABLE 1-continued
Compound Structure and Potency
| Structure | Compound ID Number | Relative Potency |
|---|---|---|
| 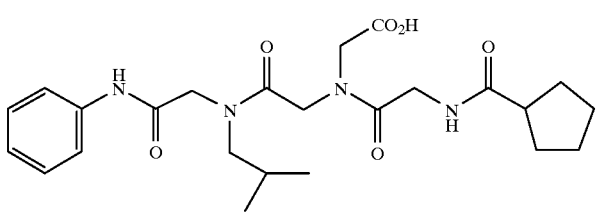 | 1032.01 | .42 |
| 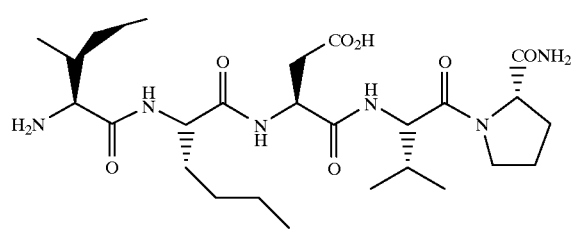 | 926.09 | .41 |
| 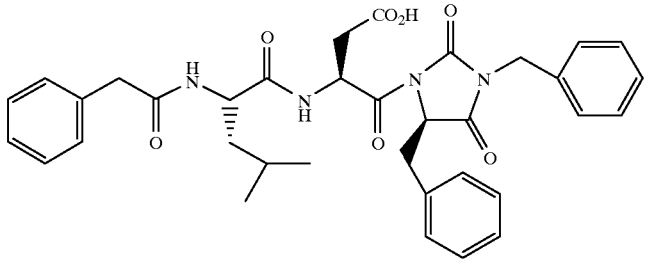 | 1047.07 | .38 |
| 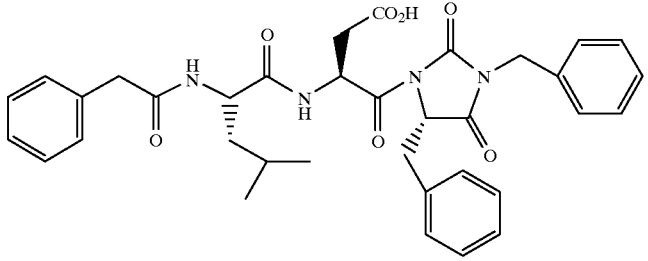 | 1047.08 | .38 |
| 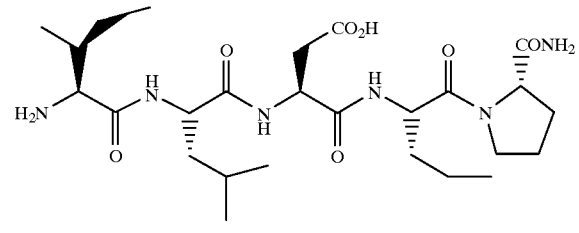 | 926.16 | .34 |

TABLE 1-continued
Compound Structure and Potency
| Structure | Compound ID Number | Relative Potency |
|---|---|---|
| 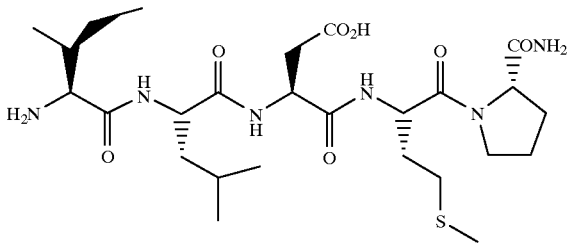 | 926.13 | .3 |
| 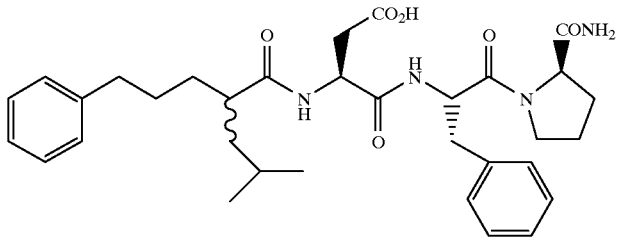 | 1056.14 | .25 |
| 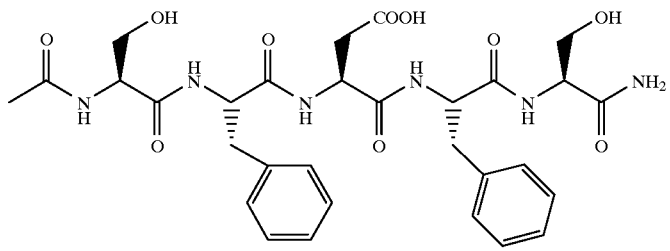 | 951.46 | .22 |
| 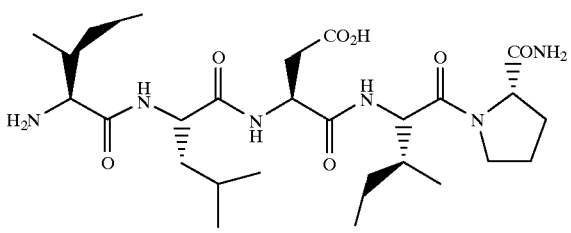 | 926.17 | .21 |
| 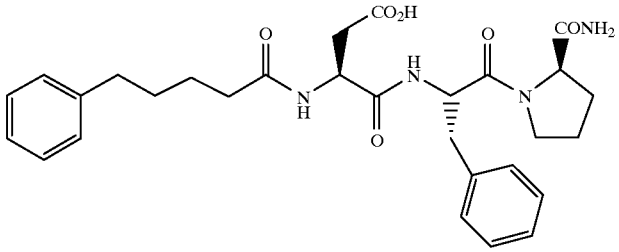 | 1056.04 | .2 |

TABLE 1-continued
Compound Structure and Potency
| Structure | Compound ID Number | Relative Potency |
|---|---|---|
| 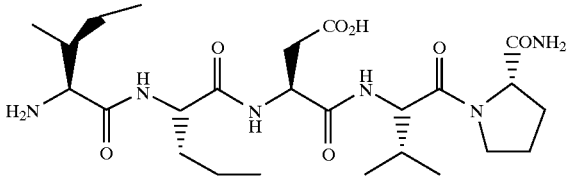 | 926.10 | .13 |
| 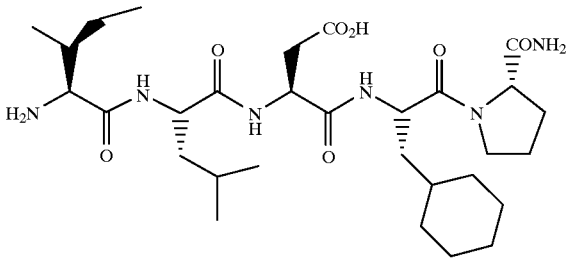 | 926.14 | .13 |
| 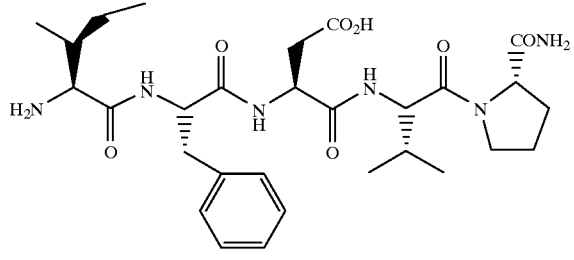 | 926.07 | .08 |
| 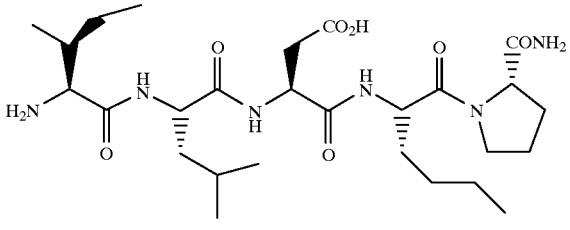 | 926.15 | .08 |
| 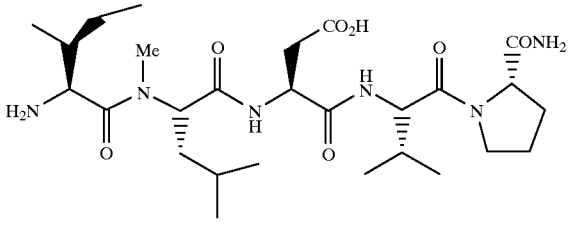 | 926.11 | .06 |

TABLE 1-continued
Compound Structure and Potency
| Structure | Compound ID Number | Relative Potency |
|---|---|---|
| 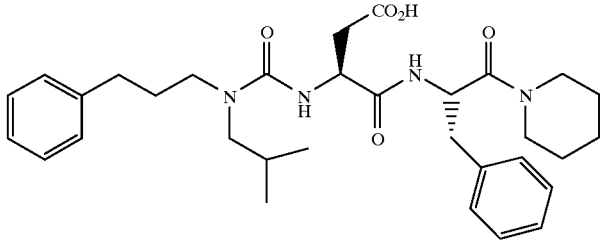 | 1027.02 | 0 |
| 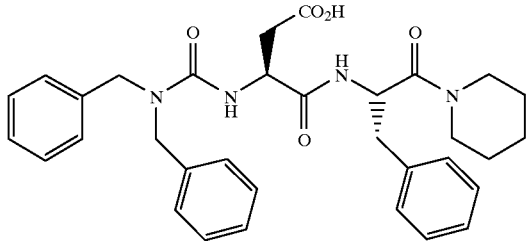 | 1027.03 | 0 |
| 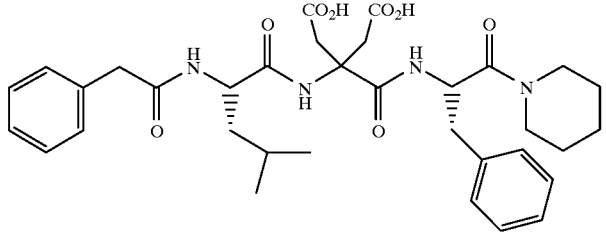 | 1026.01 | 0 |
| 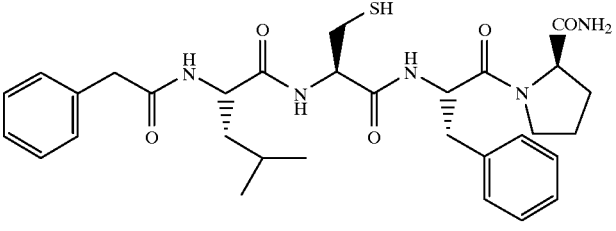 | 896.59 | 0 |
| 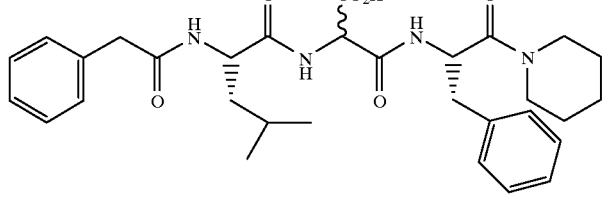 | 1026.02 | 0 |

TABLE 1-continued

Compound Structure and Potency

| Structure | Compound ID Number | Relative Potency |
|---|---|---|
| 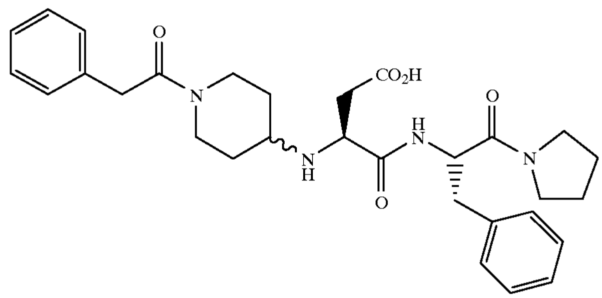 | 992.01 | 0 |
| 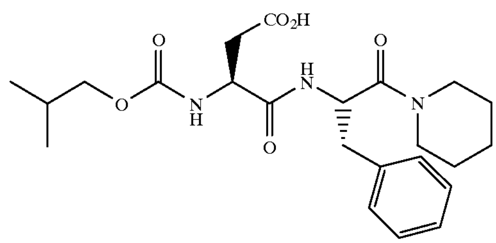 | 1027.04 | 0 |
| 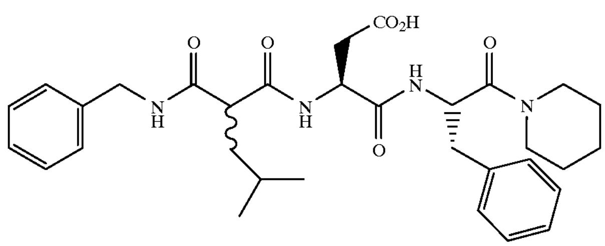 | 1034.02 | 0 |
| 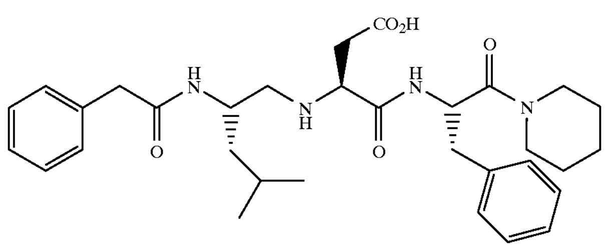 | 1041.01 | 0 |
| 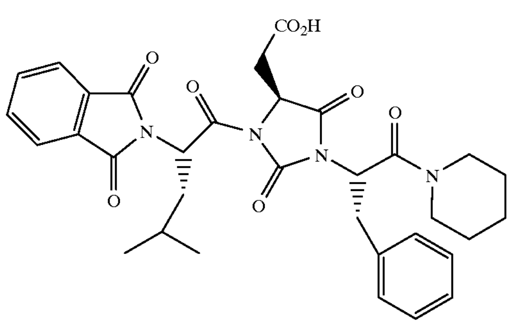 | 1047.03 | 0 |

TABLE 1-continued

Compound Structure and Potency

| Structure | Compound ID Number | Relative Potency |
|---|---|---|
| (structure) | 1047.09 | 0.01 |
| (structure) | 1066.01 | 0 |
| (structure) | 1026.06 | 0 |
| (structure) | 1026.07 | 0 |
| (structure) | 1026.08 | 0 |

TABLE 1-continued

Compound Structure and Potency

| Structure | Compound ID Number | Relative Potency |
|---|---|---|
| 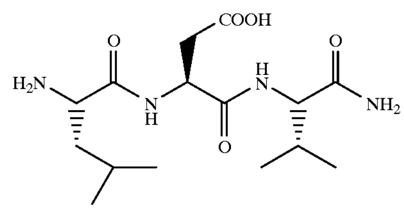 | 926.29 | 0.01 |
| 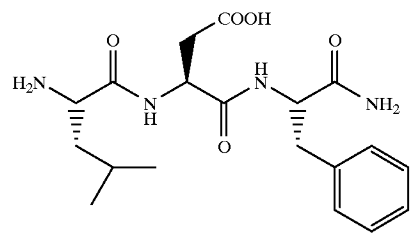 | 926.31 | 0.01 |
| 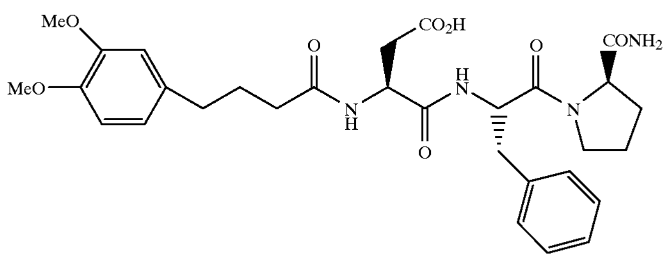 | 1056.02 | 0 |
| 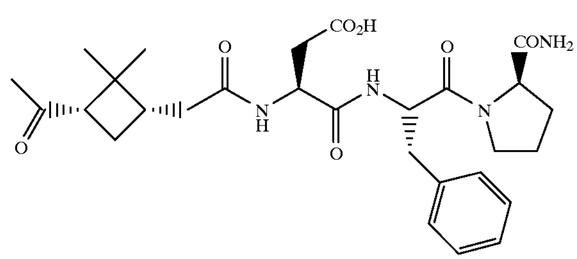 | 1056.03 | 0 |
| 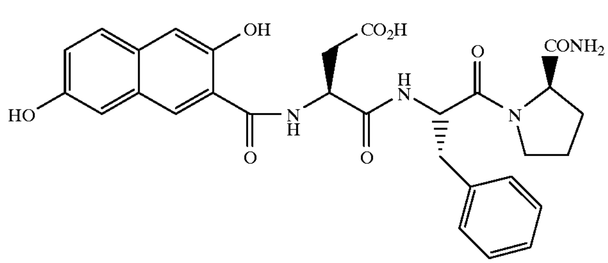 | 1056.06 | 0 |

TABLE 1-continued

Compound Structure and Potency

| Structure | Compound ID Number | Relative Potency |
|---|---|---|
| 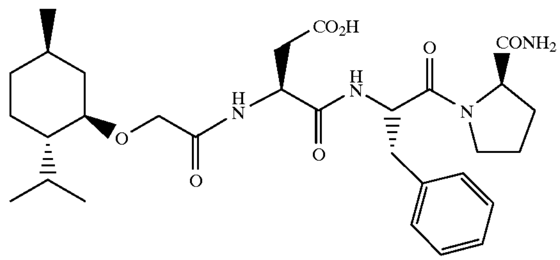 | 1056.06 | 0 |
| 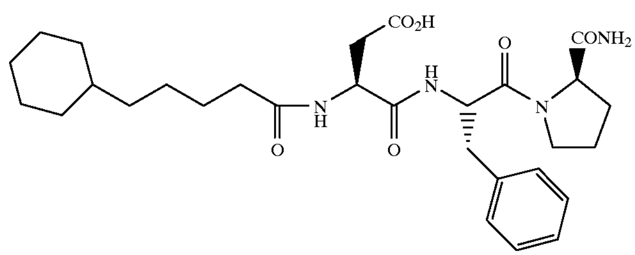 | 1056.07 | 0 |
| 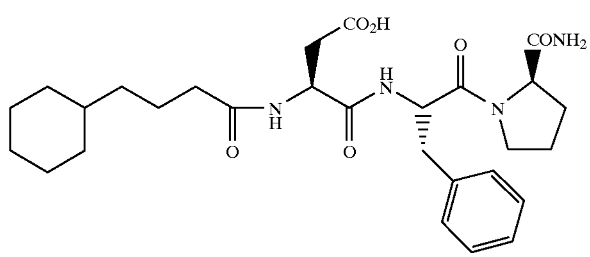 | 1056.08 | 0 |
| 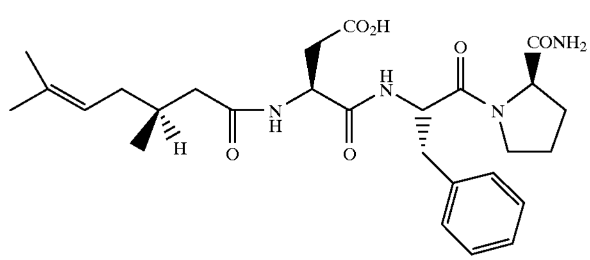 | 1056.10 | 0 |
| 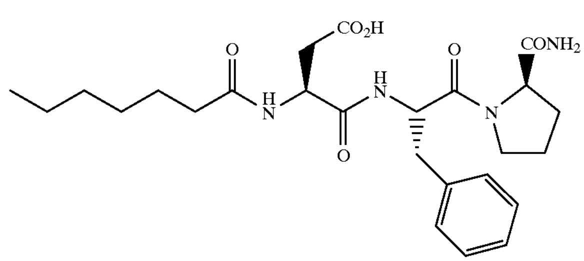 | 1056.12 | 0 |

TABLE 1-continued

Compound Structure and Potency

| Structure | Compound ID Number | Relative Potency |
|---|---|---|
| [structure] | 1056.13 | 0 |
| [structure] | 1056.11 | 0 |
| [structure] | 926.18 | 0 |
| [structure] | 1190.05 | 0 |
| [structure] | 1190.06 | 0 |

Notes:

TABLE 1-continued

Compound Structure and Potency

| Structure | Compound ID Number | Relative Potency |
|---|---|---|

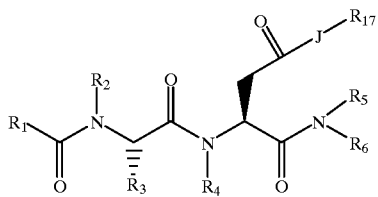

A contemplated compound is also a prodrug compound converted in vivo into an inhibitor compound. A prodrug compound itself does not necessarily bind to the VLA-4 receptor in vitro but is converted in vivo to a compound having such binding activity.

A contemplated prodrug compound corresponds to the following structural formula:

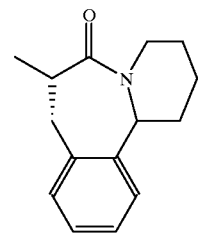

where J is a nitrogen, oxygen, or sulfur atom.

$R_{17}$ forms or is an alkyl ester, alkyl carboxylic ester, alkyl carboxamide carboxylic ester, phenyl alkyl, alkyl carboxamide, alkyl carboxylic acid, alkyl phosphonate, or biotin group.

$R_1$ is a $R_1$ ring structure, lower alkyl, or lower amino alkyl. The $R_1$ ring structure can form at $R_1$, between $R_1$ and $R_2$ or between $R_1$ and $R_4$ with the proviso that, if the $R_1$ ring structure forms at $R_1$, the $R_1$ ring structure is connected by a spacer 0 to about 5 atoms long forming one or more alkyl, N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms, and, if the $R_1$ ring structure is formed between $R_1$ and $R_4$, the heteroatoms are 2 nitrogen atoms. The $R_1$ ring structure can be aromatic, partially saturated, or saturated. The lower alkyl or lower amino alkyl group can be branched.

$R_2$ is a H or $R_2$ and $R_1$ form the $R_1$ ring structure group.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_4$ is a H or $R_4$ and $R_1$ form the $R_1$ ring structure.

$R_5$ is H or $R_5$ and $R_6$ form a $R_5$ ring structure. The $R_5$ ring structure is a fused 6,6- ring structure and can be aromatic, partially saturated, or saturated.

$R_6$ is a benzyl, or 1,1 diphenylmethine group, the $R_5$ ring structure, a group of the formula

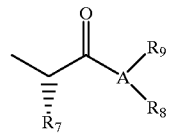

or a group of the formula

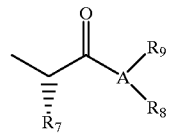

where A is nitrogen or oxygen and, when A is nitrogen, $R_7$ is a $R_7$ ring structure, lower alkyl, lower alkyl alcohol, lower thioalkyl or H group. The $R_7$ ring structure can form at $R_7$ or between $R_7$ and $R_8$ with the proviso that, if the $R_7$ ring structure forms at $R_7$, the $R_7$ ring structure is connected by an alkyl group 0 to about 3 carbon atoms long. If the $R_7$ ring structure is formed at $R_7$, the $R_7$ ring structure is a 6-, or fused 6,5-membered aromatic or non-aromatic cyclic or heterocyclic ring group wherein the heteroatom is a nitrogen atom. If the $R_7$ ring forms between $R_7$ and $R_8$, the $R_7$ ring structure is a 5-, fused 6,6-, fused 6,5-, or 7-membered heterocyclic ring group wherein the heteroatoms are 1 or 2 nitrogen atoms. The $R_7$ ring structure can optionally be substituted by an alcohol, nitro or lower alkyl ether group.

$R_8$ is a ring structure, alkyl, alkyl alcohol, or thioalkyl amide group. The ring structure can form at $R_8$ and is (N-morpholino)amino, between $R_7$ and $R_8$ and is the $R_7$ ring structure, or between $R_8$ and $R_9$ and is an $R_8$ ring structure. The $R_8$ ring structure is a 5-, 6- or fused 6,5-membered heterocyclic ring wherein the heteroatoms are 1 or 2 nitrogen atoms and 0 or 1 oxygen or sulfur atoms. The $R_8$ ring structure optionally can be substituted by one or more lower alkyl, lower dialkyl, lower alkyl carboxamide, alcohol, lower alkyl alcohol, lower hydroxy alkyl ether, carboxylic acid, lower alkyl carboxylic acid, carbonyl, sulfoxide, or alkyl substituted phenyl sulfonamido groups. The (N-morpholino) amino, alkyl, alkyl alcohol, or thioalkyl amide group can optionally contain one or more alcohol, amide, sulfhydryl, or alkyl ester groups.

$R_9$ is the $R_8$ ring structure, a lower alkyl, lower dialkyl, lower alkyl carboxamide, lower alkyl morpholine amide, cyclohexane or H group.

When A is oxygen, $R_8$ is a lower alkyl that can be branched and $R_9$ is absent.

A contemplated prodrug compound corresponds to the following structural formula:

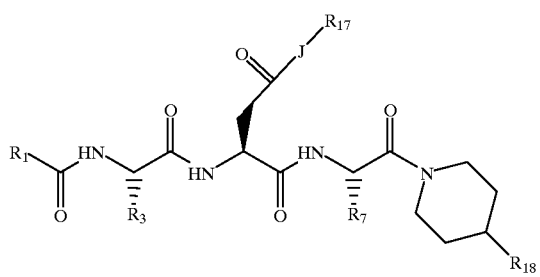

where J is a nitrogen, oxygen, or sulfur atom.

$R_{17}$ forms or is an alkyl ester, alkyl carboxylic ester, alkyl carboxamide carboxylic ester, phenyl alkyl, alkyl carboxamide, alkyl carboxylic acid, alkyl phosphonate, biotin, or H group.

$R_{18}$ is an alkyl ester, biotin or H group with the proviso that $R_{17}$ and $R_{18}$ cannot both be H groups.

$R_1$ is a $R_1$ ring structure, lower alkyl, or lower amino alkyl. The $R_1$ ring structure is connected by a spacer 0 to about 5 atoms long forming from one or more N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

A contemplated prodrug compound corresponds to the following structural formula:

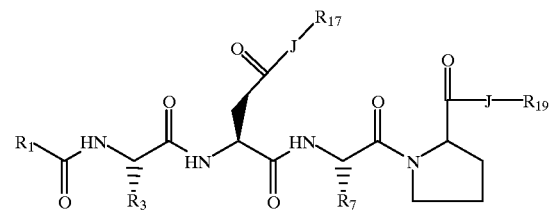

where J is a nitrogen, oxygen, or sulfur atom.

$R_{17}$ forms or is an alkyl ester, alkyl carboxylic ester, alkyl carboxamide carboxylic ester, phenyl alkyl, alkyl carboxamide, alkyl carboxylic acid, alkyl phosphonate, biotin, or H group.

$R_{19}$ is a phenyl alkyl, alkyl carboxamide, alkyl carboxylic acid, alkyl carboxylic ester, alkyl phosphonate, alkyl carboxamide carboxylic ester, biotin or H group with the proviso that $R_{17}$ and $R_{19}$ cannot both be H groups.

$R_1$ is a $R_1$ ring structure, lower alkyl, or lower amino alkyl. The $R_1$ ring structure is connected by a spacer 0 to about 5 atoms long forming from one or more N-amido, N-sulfonimido, N-urea, N-carboxyl groups. The spacer can be optionally substituted by an amino group. The $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups. The $R_1$ ring structure is cyclic or heterocyclic with the proviso that the heteroatoms are 1 or 2 nitrogen atoms. The $R_1$ ring structure can be aromatic, partially saturated, or saturated. The lower alkyl or lower amino alkyl group can be branched.

$R_3$ is a $R_3$ ring structure, lower alkyl, lower alkyl alcohol or lower thioalkyl. The $R_3$ ring structure group is a 6-membered ring that is connected by an alkyl group 0 to about 3 carbon atoms long. The lower alkyl, lower alkyl alcohol, or lower thioalkyl group can be branched.

$R_7$ is a $R_7$ ring structure, lower alkyl, lower alkyl alcohol, lower thioalkyl or H group. The $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom. The $R_7$ ring structure can optionally be substituted by an alcohol, nitro or lower alkyl ether group.

Table 2 provides the structural formula of exemplary prodrug compounds along with their binding inhibition potencies relative to the standard compound of SEQ ID NO:3, assigned a relative potency of 1. The prodrug compound relative potency of Table 2 is the potency before the prodrug compound is enzymatically converted to an active form. The compound ID number of Table 2 cross-references individual compounds herein.

TABLE 2

Prodrug Compound Structure and Potency

| Structure | Compound ID Number | Relative Potency |
|---|---|---|
| 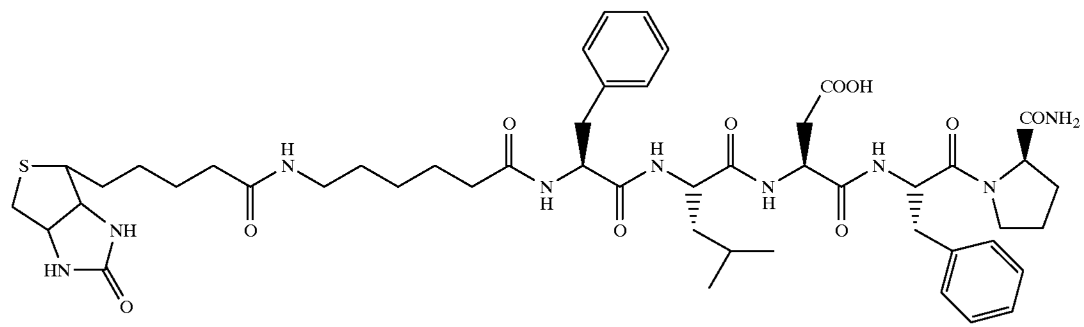 | 951.13 | 74.5 |
| 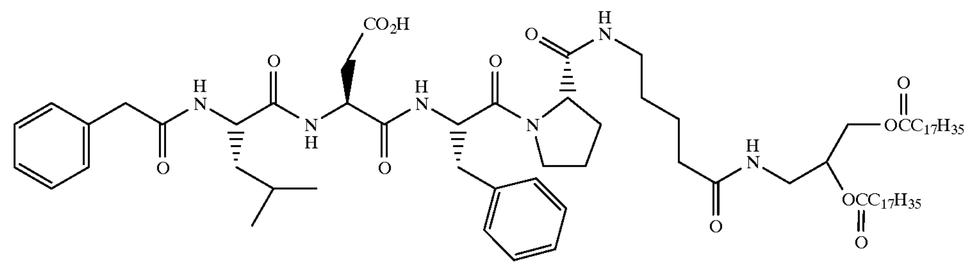 | 1068.03 | 6.26 |
| 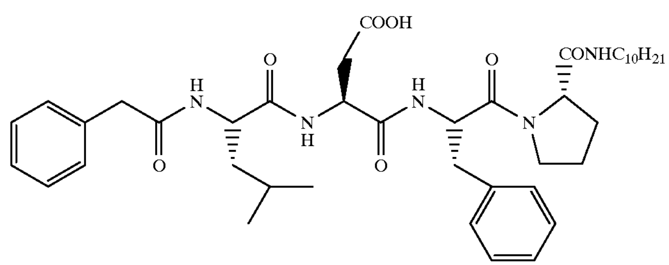 | 1068.04 | 2.13 |

TABLE 2-continued

| Structure | Prodrug Compound Structure and Potency | Compound ID Number | Relative Potency |
|---|---|---|---|
| | | 1068.02 | 1.1 |
| | | 1067.01 | .97 |
| | | 1068.01 | .91 |

TABLE 2-continued

Prodrug Compound Structure and Potency

| Structure | Compound ID Number | Relative Potency |
|---|---|---|
| 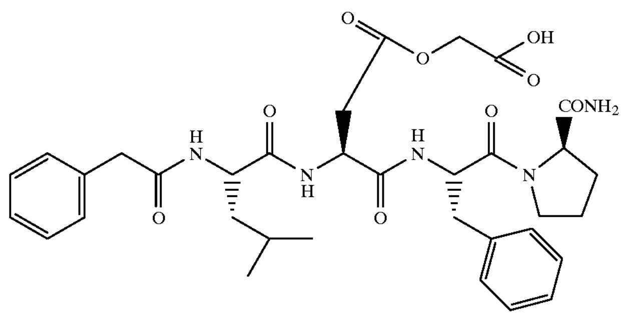 | 1067.02 | .81 |
| 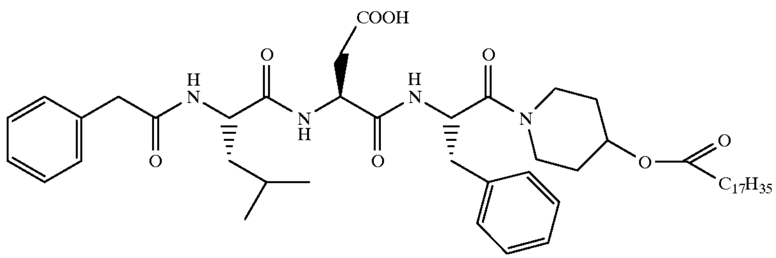 | 1068.05 | .63 |
| 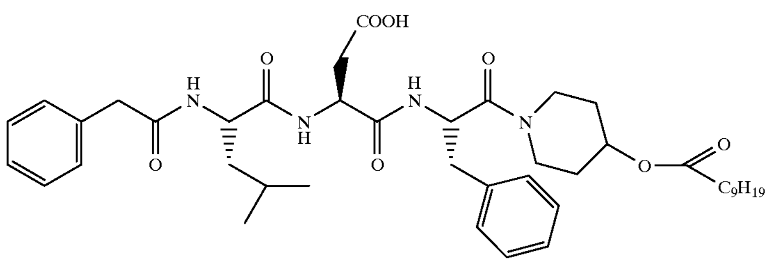 | 1068.06 | .63 |

TABLE 2-continued

Prodrug Compound Structure and Potency

| Structure | Compound ID Number | Relative Potency |
|---|---|---|
| (structure) | 1190.01 | 0 |
| (structure) | 1068.07 | 0 |
| (structure) | 1068.08 | 0 |

TABLE 2-continued

Prodrug Compound Structure and Potency

| Structure | Compound ID Number | Relative Potency |
|---|---|---|
| 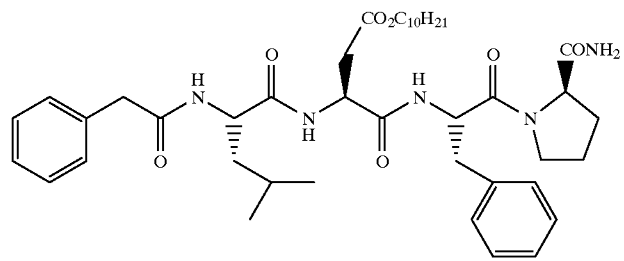 | 1068.09 | 0 |
| 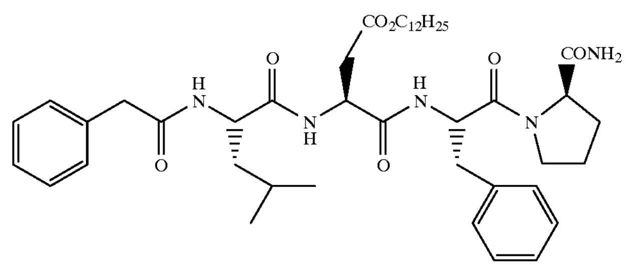 | 1068.10 | 0 |
| 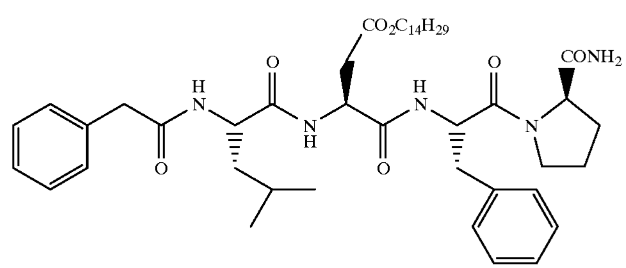 | 1068.11 | 0 |

TABLE 2-continued

Prodrug Compound Structure and Potency

| Structure | Compound ID Number | Relative Potency |
|---|---|---|
| 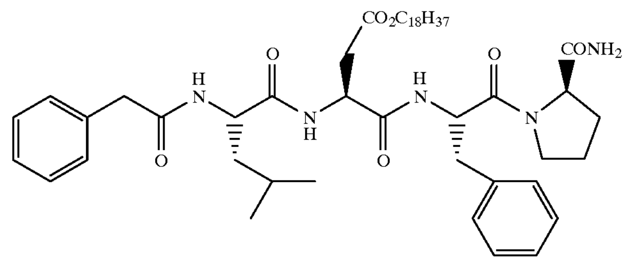 | 1068.12 | 0 |
| 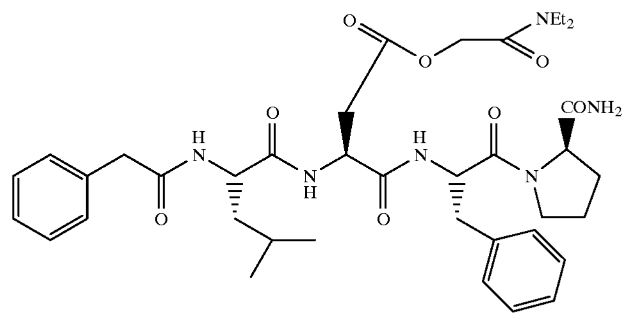 | 1068.13 | 0 |
| 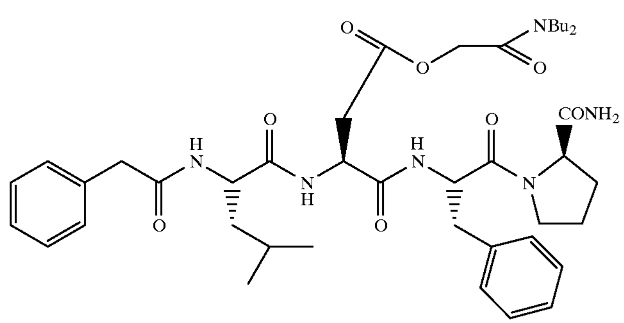 | 1068.14 | 0 |

A contemplated compound also includes a bioisoster of a disclosed compound. As used herein, the term "bioisoster" refers to a compound differing from a disclosed compound by an one or more atoms expected to produce an equivalent biological effect. An example of a bioisosteric substitution is the interchange of nitrogen and carbon in an aromatic ring. See, for example, *Medicinal Chemistry*, ed. by Alfred Burger, Interscience Publishers, New York (1960), which is incorporated herein by reference.

A contemplated compound includes a described compound coupled to a fluorescent group, a group that enhances solubility in an aqueous environment, or binding group, such as, for example, an europium epsilon amidocarproyl, N-acetyl glucosamine or biotin group, respectively. A contemplated compound includes a compound containing two or more of the described compounds attached together to form a multi-valent compound by a linking group such as, for example, a tetraethylenepentatamine group.

As used herein, the term "lower alkyl" refers to an alkyl group 1 to about 5 carbon atoms long. The term "alkyl" refers to an alkyl group 1 to about 15 atoms long.

Compounds of the present invention comprise chemical moieties attached to a peptide backbone. For a chemical moiety defining an amino acid, a contemplated inhibitor compound can also be defined using the single or triple letter abbreviation for an amino acid. In this description, the abbreviations used herein for derivatives and residues of the twenty natural amino acids are reproduced in the following Table of Correspondence:

TABLE 3

TABLE OF CORRESPONDENCE

| Abbreviation | | |
|---|---|---|
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

Compound sequences are written from left to right and in the direction from amino-terminus to carboxyl-terminus. The single letter amino acid abbreviation of Table 3 does not apply to single letter atomic symbol or variable abbreviations used in molecular formulas herein.

A contemplated inhibitor compound defined as an amino acid sequence corresponds to formula A:

X-B-Asp-Z                          A wherein

B is an α-hydrophobic amino acid residue.

X is a group amide-linked to the nitrogen atom of the B α-amine. The X group has a ring structure bonded to the carbonyl carbon of the amide-linkage by a spacer having a length of zero to about two methylene groups. The length of X, including the spacer and carbonyl carbon, is about that of a 3-quinoline carbonyl group or smaller. The ring structure is a 5- and 6-membered ring or a fused 6,6- or 6,5-membered ring. Alternatively, the X substituent, including the spacer, cyclic ring structure, the carbonyl group and the α-amino nitrogen atom of B can also together form an aromatic ring-substituted cyclic imido group.

Z is selected from the group consisting of:

(a) Xaa-NCy$^1$ where Xaa is Val, Ile, Leu or an aromatic amino acid residue; i.e., a residue having a side chain that contains one or two fused aromatic rings, and NCy$^1$ is a cyclic ring-containing group having a ring nitrogen atom that forms an amide bond with the α-carboxyl group of Xaa, and whose cyclic ring contains 5- or 6-atoms including said ring nitrogen atom; and (b) NCy$^2$ where the depicted nitrogen is an amine substituent of a cyclic group whose depicted nitrogen atom forms an amide bond with the α-carboxyl group of the Asp, and which amine substituent is bonded to a 6- or 7-membered ring or to a fused 6,6- or 6,7-membered lactam ring system in which the ring bearing the amine substituent is saturated and contains the amine substituent α to the carbonyl group of the lactam.

A compound of formula A is water-soluble and inhibits the binding of Jurkat cells (ATCC TIB 152) to a solid phase-bound compound of SEQ ID NO:1 in an in vitro assay in an aqueous buffer at a pH value of 7.2–7.4. The binding inhibition exhibited by a compound is measured relative to that of SEQ ID NO:3. Preferably, the binding inhibition of a compound is ten times or more that of SEQ ID NO:3.

The sequence of a compound of formula A appears to require the Asp residue present in the CS-1 (SEQ ID NO:1) and B12 (SEQ ID NO:3) fibronectin compounds. Aside from that Asp, both of whose size and charge appear to be required for binding as Glu and other residues barely inhibit binding, size and relative hydrophobicity appear to be most important in the selection of the B residue. The requirements of the other residues are discussed hereinafter.

Exemplary B residues as amino acids are selected from the group consisting of leucine (Leu), cyclohexylalanine, norleucine (Nle), Methionine (Met), homoserine, threonine (Thr), phenylalanine (Phe), valine (Val), norvaline (Nva), and isoleucine (Ile). B is most preferably Leu.

Preferably, a contemplated inhibitor compound defined as an amino acid sequence corresponds to formula I:

X-Leu-Asp-Z                        I wherein

X is a group amide-linked to the nitrogen atom of Leu, the group having a ring structure bonded to the carbonyl carbon of the amide-linkage by a spacer having a length of zero to about two methylene groups. The length of X, including the spacer and carbonyl carbon, is about that of a 3-quinoline carbonyl group or smaller. The ring structure is a 5- and 6-membered ring or a fused 6,6- or 6,5-membered ring. Alternatively, the X substituent, including the spacer, cyclic ring structure, the carbonyl group and the α-amino nitrogen atom of Leu can also together form an aromatic ring-substituted cyclic imido group.

Z is selected from the group consisting of:

(a) Xaa-NCy$^1$ where Xaa is Val, Ile, Leu or an amino acid residue having a side chain that contains one or two fused aromatic rings and NCy$^1$ is a cyclic ring-containing group having a ring nitrogen atom that forms an amide bond with the α-carboxyl group of Xaa, and whose cyclic ring contains 5- or 6-atoms including said ring nitrogen atom; and (b) NCy$^2$, where the depicted nitrogen is an amine substituent of a cyclic group whose depicted nitrogen atom forms an amide bond with the α-carboxyl group of the Asp residue, and which amine substituent is bonded to a 6- or 7-membered ring or to a fused 6,6- or 6,7-membered lactam ring system in which the ring bearing the amine substituent is saturated and contains the amine substituent α to the carbonyl group of the lactam.

A compound of formula I, as well as formulas II and III below, is water-soluble and inhibits the binding of Jurkat cells to a solid phase-bound compound of SEQ ID NO:1 in an in vitro assay in an aqueous buffer at a pH value of 7.2–7.4. The binding inhibition exhibited by a compound is measured relative to that of SEQ ID NO:3. Preferably, the inhibition of a compound is ten times or more that of SEQ ID NO:3.

Examining formula I, it is seen that at least Leu and Asp of the CS-1 (SEQ ID NO:1) and B12 (SEQ ID NO:2) fibronectin compounds are present. Aside from that two residue sequence, the sequence/structure of a contemplated inhibitor compound and the CS-1 or B12 portions are quite different.

Thus, whereas there is an iso-leucine (Ile;I) compound-(amide-) bonded to the α-amine group of the Leu residue in CS-1 and the native protein, a cyclic ring structure-containing group or moiety, X, is amide-bonded to the nitrogen atom of the B or Leu residue α-amino group (formulas A or I, respectively) via a carboxyl contributed by the cyclic ring structure-containing group. That amide bond can be present as part of a carboxamide- [—C(O)NH—], urethane- [—O—C(O)NH—] or urea- [—NH—C(O)NH—] containing spacer group that links the cyclic ring structure-containing group to the Leu residue.

The cyclic ring structure broadly can be any 5- or 6-membered ring that is saturated or contains ethylenic unsaturation. The ring structure can contain one or more atoms other than carbon such as nitrogen, oxygen or sulfur. The ring structure can also be a fused ring system where two 6-membered rings are fused (6,6-) or where a 6-membered ring is fused to a 5-membered ring (6,5-membered). The ring of the cyclic ring structure is preferably aromatic.

Exemplary ring structures include tetrahydrofuranyl, tetrahydropyranyl, cyclopentyl, cyclohexyl, phenyl, pyridyl, pyrimidinyl, pyrazinyl, pyrazolyl, pyrrolidyl, furanyl, piperidinyl, naphthyl, quinolinyl, decalinyl, quinazolinyl, imidazyl, thiophenyl, and the like. Of the cyclic ring structures, phenyl and pyridyl are particularly preferred.

A cyclic ring structure can be bonded directly to the carbonyl group [—C(O)—] of the amide bond to the B or Leu residue. That ring can also be spaced away from the carbonyl group by up to about the length of two methylene (—CH$_2$—) groups or an ethylene group (—CH$_2$—CH$_2$—).

The Van der Waals radius a methylene group (about 2.0 Å) is slightly longer than that of an oxy group (—O—; about 1.40 Å) or an imino group (—NH—; about 1.50 Å). There is sufficient similarity between the sizes of methylene, oxy and imino so that a spacer group containing a —CH$_2$—O—, —CH$_2$—NH—, —NH—NH—, or —O—NH— are of similar lengths and are within the length of an ethylene group, —CH$_2$—CH$_2$—. A similar result obtains if bond lengths (distances) are used. Contemplated spacers include —HC(CH$_3$)—CH$_2$—, —CH$_2$—CH$_2$—, —NH—O—, —HN—NH—, —CH$_2$—O— and —CH$_2$—NH—, and are preferably free of unsaturation.

Using a phenyl ring as an exemplary aromatic ring structure, it is seen that the contemplated X groups include 3-methyl-3-phenylpropionyl, 3-phenylpropionyl, phenylhydroxaminocarbonyl [Ph—NH—O—C(O)—], phenylhydrazidecarbonyl [Ph—NH—NH—C(O)—], benzyloxycarbonyl [Ph—CH$_2$—O—C(O)—], phenoxyacetyl [Ph—O—CH$_2$—C(O)—], benzylaminocarbonyl [Ph—CH$_2$—NH—C(O)—], and anilinoacetyl [Ph—NH—CH$_2$—C(O)—], where "Ph" is a phenyl group.

Thus, it is contemplated that a before-described ring structure be bonded to the carbonyl carbon of the B- or Leu-linked amide group by a spacer having a length of zero methylene groups (a direct bond), one or two methylene groups. Put differently, the spacer has the length of about an ethylene group or less.

A phenylacetyl, phenoxycarbonyl or anilinocarbonyl group bonded to the nitrogen of the B or Leu α-amino group contains a spacer having the length of about one methylene group. Phenyl (benzoyl), 1- or 2-naphthyl (1- or 2-naphthalenecarbonyl), 2-, 3- or 4-pyridyl (2-, 3- or 4-pyridinecarbonyl), 2- or 3-thiophenyl (2- or 3-thienyl; 2- or 3-thiophencarbonyl) and 2- or 3-furanyl (2- or 3-furancarbonyl) ring structures are bonded directly to the amide carbonyl carbon and therefore define an X group that utilizes a spacer having a length of zero methylene groups. A spacer having a length of about two methylene groups is provided by an X group that is carbobenzyloxy [Ph—CH$_2$—O—C(O)—], carbobenzylamino [Ph—CH$_2$—NH—C(O)—], carbophenoxymethylene [Ph—O—CH$_2$—C(O)—]) and the like groups.

A contemplated 5- or 6-membered ring structure can also be substituted with a C$_1$–C$_2$ alkyl or hydroxyl group. Exemplary substituted ring structures using a phenyl ring as illustrative thus include 2-, 3- or 4-ethylphenyl, 2,6-, 3,4- or 2,3-dimethylphenyl, 2-, 3- or 4-hydroxyphenyl, 2,6-, 2,4-, 3,4- and 3,5-dihydroxyphenyl, and the like.

The ring structure of the X substituent is thought to act in a contemplated inhibitor in some way to fit the inhibitor compound into the binding pocket of the VLA-4 receptor to position the B or Leu and Asp groups into a proper configuration. Because of that presumed role in fitting the compound into its receptor, there are some size constraints upon the ring structure-containing and spacer portions of X, in addition to those noted before as to the spacer group length. Thus, from the carbonyl-containing carbon of the amide bond to B or Leu, through the end of ring structure or its substituent furthest from the carbonyl group, the total length of the spacer plus ring structure-containing portion of X is about the size of a 3-quinolinecarbonyl group or smaller.

Inasmuch as a 3-quinolinecarbonyl group is the longest contemplated ring structure-containing X substituent, a 3-quinolinecarbonyl group is free from the above-discussed substituents that add to its length.

The length of a given X substituent can be readily determined, as discussed before. For example, one can use space-filling models to build exemplary cyclic ring structure-containing X groups and then compare the relative sizes of the prepared models. One can also use published bond lengths bond angles to prepare a two-dimensional depiction of the sizes. Computer graphics programs are also well-known and available that can be used to prepare exemplary model X groups for length comparison to 3-quinolinoyl.

The X substituent, including the spacer, cyclic ring structure, the carbonyl group and the α-amino nitrogen atom of B or Leu can also together form an aromatic ring-substituted cyclic imido group. Exemplary of such cyclic imido groups are phthalimido, which is preferred, each of 2,3- and 3,4-pyridinedicarboximido, homophthalimido and 1,2,3,4-tetrahydroquinazoline-2,4-dione-3-yl groups in which the aromatic ring and cyclic imido group are fused together.

In another exemplary compound, the B or leucine nitrogen atom is an imido nitrogen atom within the ring of a 5-phenylhydantoin-3-yl group so that the aromatic phenyl ring is a substituent of a cyclic spacer and is spaced about one methylene away from the carbonyl group linked to the Leu residue. A similarly structured imido nitrogen-containing X group is present in a 2-phenylsuccinimido group formed on the B or Leu nitrogen atom.

The cyclic imido- and hydantoin-containing portions of the above-discussed X groups can thus be viewed as specialized spacer groups that limit the conformational degrees of freedom of the ring structures. Thus, for example, whereas the carbonyl, methylene and phenyl portions of a phenylacetyl group are each free to assume one or more of several conformations, a phthalimido X group can only spin about the axis of the leucine nitrogen-methine bond.

It is noted that although the X substituent must contain a cyclic ring structure that can be substituted as discussed before, that X substituent can also include a further substituent on other than the ring structure. When a further substituent is present, X preferably is an amino acid residue having a cyclic ring side chain that therefore includes a primary or secondary amine. Here, X is preferably a prolyl, phenylalanyl, tyrosinyl or phenylglycyl residue, the nitrogen atom of whose α-amino group is bonded to the further substituent.

That further substituent can be one amino acid residue through the remainder of the CS-1 compound sequence toward the N-terminus thereof, with the sequence of that compound beginning at the isoleucine of position 19 from the N-terminus of SEQ ID NO:1. A single residue or 18 separate amino acid residue substituent sequences are thereby defined.

Another exemplary further substituent linked via an amine group of X is biotin. In a particular example, biotin amide-bonded to ε-aminocaproic acid was amide-bonded to the α-amine of a phenylalanine (Phe) as an X group. The resulting compound contained the biotin fused ring amide-linked to the Phe X group via a chain of twelve atoms.

It should also be understood that an X group amino acid residue having a cyclic ring side chain can also be free of substituent groups. The nitrogen atom of the α-amine of such a residue can also be acylated as with a $C_1$–$C_6$ acyl group such as formyl, acetyl, iso-butyryl, or hexanoyl group. A $C_1$–$C_6$ acyl group bonded to the nitrogen of an α-amine group forms an amide bond at that nitrogen atom and provides no ionic charge to the compound at a pH value of 7.2–7.4 as compared to the positive charge provided by an unsubstituted free α-amine.

The Z group of a before-discussed formula can be one of two types of groups. The Z group in one embodiment (A) is a hydrophobic amino acid residue Xaa compound-bonded to the Asp carboxyl and linked to a cyclic ring-containing group $NCy^1$ that has a ring nitrogen atom (the N of $NCy^1$) that forms an amide bond with the α-carboxyl group of Xaa. The cyclic ring of $NCy^1$ contains 5- or 6-atoms, including the depicted nitrogen atom (N of $NCy^1$). Contemplated hydrophobic amino acid residues are those having aliphatic side chains such as valine, leucine and isoleucine. Xaa more preferably contains a hydrophobic aromatic amino acid residue; i.e., Xaa is an amino acid residue having an aromatic side chain that contains one or two fused aromatic rings. Exemplary of such aromatic amino acids are phenylalanine, tyrosine and tryptophan that are naturally occurring (genetically encoded) as well as phenylglycine, homophenylalanine, P-nitrophenylalanine, thiophenylglycine (thienylglycine), and the like.

Exemplary $NCy^1$ groups include morpholinyl, thiomorpholinyl, thiomorpholinylsulfone [4-(thiadioxo)piperidinyl], piperidinyl, piperazinyl, pyrrolidinyl, pyrazolyl, pyrazolinyl, oxazolidinyl and the like as their respective amides. A $NCy^1$ cyclic ring can also be substituted with one or two substituent groups selected from the group consisting of carboxyl, carboxamide, $C_1$–$C_4$ alkylenecarboxyl $C_1$–$C_4$ alkylenecarboxamide, hydroxyl, hydroxymethyl, $(CH_2CH_2O)_nH$ where n is one, two or three and $C_1$–$C_4$ alkyl. Carboxyl substitution at the 2-position of a pyrrolidine provides the amino acid proline, whose D- and L-forms are both contemplated herein. D-Prolyl (sometimes shown in bold face lower case single letter amino acid code as "P" or as D-Pro) is particularly preferred as its amido derivative (D-Pro-$NH_2$) as are morpholinyl, piperidyl, piperazinyl and 4-hydroxypiperidyl.

Exemplary $C_1$–$C_4$ alkyl groups include methyl, ethyl, iso-propyl, n-butyl and t-butyl. A $C_1$–$C_4$ alkyl group can also form a quaternary ammonium group with a second nitrogen atom of $NCy^1$ such as piperazine. Where the $C_1$–$C_4$ alkyl group is a methyl group, and iodide is the anion, and exemplary $NCy^1$ group is a 4,4-N,N-dimethylpiperaziniumyl iodide.

Exemplary $C_1$–$C_4$ alkylenecarboxyl and $C_1$–$C_4$ alkylenecarboxamide groups include methylenecarboxyl (—$CH_2CO_2H$; carboxymethyl) and methylenecarboxamido (—$CH_2CONH_2$; carboxamidomethyl), ethylenecarboxyl (—$CH_2CH_2CO_2H$; carboxyethyl) and ethylenecarboxamido (—$CH_2CH_2CONH_2$; carboxamidoethyl) as well as butylenecarboxyl (—$C_4H_8CO_2H$; carboxybutyl) and butylenecarboxamido (—$C_4H_8CONH_2$; carboxyamidobutyl). Exemplary groups $(CH_2CH_2O)_nH$ where n is one, two or three include 2-hydroxyethyl (n=1), 5-hydroxyethylenoxyethylene (ethyleneoxyethanol; 5-hydroxy-3-oxapentyl; n=2) and 8-hydroxy-3,5-dioxaoctyl (n=3).

When $NCy^1$ includes a piperazinyl group, the second (4-position) nitrogen atom cannot only be quaternized by alkylation, but also amidified. Exemplary acyl portions of the piperazinyl-4-N-amides include $C_1$–$C_6$ acyl groups such as formyl, acetyl, propanol, isobutanoyl, hexanoyl and benzoyl, but also sulfonamides such as phenylsulfonamido, toluenesulfonamide (tosyl), methanesulfonamide (mesyl) and trifluoromethylsulfonamido (trifyl).

Thus, in those embodiments where Z is Xaa-$NCy^1$, Xaa is a specified amino acid residue whose amine group forms an amide (compound) bond with the α-carboxyl of the depicted Asp residue, and whose carboxyl group forms an amide bond with a nitrogen atom present within the 5- or 6-membered ring of $NCy^1$.

In another embodiment (B) Z is $NCy^2$ where the depicted nitrogen atom (N of $NCy^2$) is an amine substituent of a cyclic group ($Cy^2$) whose substituent nitrogen atom forms an amide bond with the α-carboxyl of the depicted Asp residue. That amine substituent is bonded to a cyclic group that is (I) a 6- or 7-membered ring or (ii) a fused 6,6- or 6,7-membered lactam ring system in which the ring bearing the amine substituent is saturated (free of ethylenic unsaturation) and contains the amine substituent α to the carboxyl group of the lactam.

Here, the nitrogen atom that links the ring system to the remainder of the compound is a substituent of a cyclic ring structure rather than being a ring atom as in $NCy^1$. In addition, the rings of which that nitrogen can be a substituent are of two types, 6- or 7-membered rings or 6,6- or 6,7-membered fused ring systems, one of which rings is a lactam. In either situation, there is no Xaa amino acid residue in this embodiment.

Exemplary amine substituent-containing 6- and 7-membered ring $NCy^2$ groups of this type include benzylamine, phenethylamine, 2-(N-morpholinyl)-ethylamine, N-[1-(carboxamidomethyl)-caprolactam-3-yl] amine, N-(caprolactam-3-yl)amine, and N-(valerolactam-3-yl)amine groups that form the corresponding amides with the α-carboxyl of Asp. Exemplary amino-substituted 6,6- and 6,7-fused ring lactam-containing $NCy^2$ groups include N-[1-(2-N-morpholinylethyl)-2-oxo-tetrahydroquinolin-3-yl]amine, N-(2-oxo-tetrahydroquinolin-3-yl)amine and the 6,7-fused ring tricyclic compound shown at footnote 7 of Table 1 groups that form corresponding amides with the α-carboxyl of Asp.

It has generally been found that once (I) the X group of a formula discussed herein is occupied by an aromatic ring-containing moiety spaced adjacent to or within about one methylene group's distance from the carbonyl, (ii) Z is an aromatic amino acid, and (iii) $NCy^1$ is L- or D-proline amide or a 5- or 6-membered nitrogen-containing ring as discussed before, substantially any other substituent can be present linked to either compound terminus without abolishing the inhibitory activity of a contemplated compound, so long as the resulting compound is water-soluble.

Thus, for example, the compound of SEQ ID NO:5 having an N-terminal phenylacetyl group linked to the sequence Leu-Asp-Phe-Pro can further include a substituted tetraethylenediamine group amide-bonded to the Pro residue in which four phenylacetyl-Leu-Asp-Phe-Pro groups were amide-bonded to the tetraethylenediamine nitrogens and still exhibit VLA-4 binding inhibition that was better than the standard 10-mer compound of SEQ ID NO:3.

Similarly, the compound PheLeuAspPhe-D-Pro-$NH_2$ contained a europium-containing chelate at its N-terminus bonded to the nitrogen atom of the N-terminal Phe. That compound exhibited a binding inhibition better than that of the compound of SEQ ID NO:3.

The compound of SEQ ID NO:12, phenylacetyl-Leu-Asp-Phe-Pro-$NH(CH_2)_5C(O)NHC_{18}H_{37}$, would be predicted to be a good inhibitor. However, that compound is not water-soluble and forms a turbid dispersion rather than a solution. That compound exhibits a binding inhibition similar to that exhibited by the standard 10-mer compound of SEQ ID NO:3.

Any compound having binding activity can be used. However, a preferred contemplated inhibitor compound inhibits the binding of inflammatory cells that contain the VLA-4 receptor [Jurkat cells (American Type Culture Collection, Rockville, Md. 20852, ATCC TIB 152)] to the solid phase-bound CS-1 compound (SEQ ID NO:1) in an aqueous buffer at pH 7.2–7.4 to an extent that is about 10-fold to about 1000-fold and more preferably 3000-fold better than that binding exhibited by the art standard 10-mer compound of SEQ ID NO:3 [GPEILDVPST in single letter code). More preferably, that binding is inhibited by about 50- to about 3000-fold, and most preferably by about 100- to about 3000-fold. However, an inhibitor compound having less than about 10-fold binding but having in vivo efficacy is also contemplated.

Binding inhibition is measured here as a concentration of compound that inhibits one-half the binding between a standard number of Jurkat cells and a standard amount of CS-1 compound bound to the surface of a microtiter plate well. Those concentrations are conveniently expressed as $IC_{50}$ values, smaller numbers indicating a lower concentration required to inhibit 50 percent binding and therefore greater potency. Further specifics of this assay are provided hereinafter.

To recapitulate, a compound of formulas A or I inhibits binding between the CS-1 compound region of fibronectin and the VLA-4 receptor. Those inhibitors that are at least ten-times better inhibitors than the compound of SEQ ID NO:3 are preferred.

Still more preferred is a compound of formula II, below,

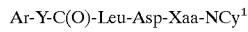 II wherein Ar is a pyrazolyl, phenyl, pyridyl (2-, 3- or 4-), or 3-quinolinyl group;

Y is a spacer that is absent, —$CH_2$—, —CH(NH)—, —O— or —NH—;

or Ar-Y-C(O) together with the nitrogen atom of Leu forms a phthalimido, a 1,2,3,4-tetrahydroquinazoline-2,4-dione-3-yl or 5-phenylhydantoin-3-yl group, Ar-Y-C(O)- has a length of about 3-quinolinecarbonyl or less;

Xaa is an aromatic amino acid residue; i.e., an amino acid residue having an aromatic side chain, such as phenylalanine, tyrosine, tryptophan, homophenylalanine, nitrophenylalanine, thienylglycine and phenylglycine; and $NCy^1$ is an amine-containing 5- or 6-membered cyclic ring group whose depicted nitrogen atom, N of $NCy^1$, is within the ring and forms an amide bond with the α-carboxyl of Xaa, as was discussed before.

Of the above combinations, Ar-Y-C(O), a more preferred X group of formula I, is preferably benzoyl, phenylacetyl, 4-pyridinecarbonyl (isonicotinoyl), 3-pyridinecarbonyl (nicotinoyl), 3-pyridinacetyl, anilinocarbonyl, 3-quinolinoyl, pyrazolecarbonyl, tryptophyl and 3,4-dihydroxybenzoyl, with phenylacetyl (benzylcarbonyl) being most preferred, or Ar-Y-C(O) together with the nitrogen atom form a phthalimido group. Xaa is preferably Phe, Tyr or Trp, with Phe being most preferred. $NCy^1$ is preferably an amide of a morpholinyl, piperidinyl or substituted piperidinyl where the substituent is selected from the group consisting of hydroxyl, carboxyl, carboxamido groups, piperazinyl or 4-substituted piperazinyl in which the 4-substituent is selected from the group consisting of $C_1$–$C_4$ alkyl, $C_1$–$C_4$ alkylenecarboxyl, $C_1$–$C_4$ alkylenecarboxamide, $(CH_2CH_2O)_nH$ where n is 1, 2 or 3, thiomorpholinyl, L- or D-prolinyl amide, pyrrolidinyl, 3,4-dihydroxypyrrolidinyl, 2-(hydroxymethyl)pyrrolidinyl and 4-(thiadioxo)piperidinyl group, with amides of morpholinyl, D-prolinyl amide, piperidinyl, an above-substituted piperidinyl, piperazinyl, an above-substituted piperazinyl and pyrrolidinyl groups being most preferred.

A most preferred compound corresponds in sequence to a compound of formula III, below,

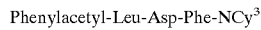 III wherein $NCy^3$ is a group of most preferred $NCy^1$ groups and is selected from the group consisting of morpholinamido, thiomorpholino, 4-(thiadioxo)piperidinamido, D-2-(carboxamido)pyrrolidinamido, piperazinamido, substituted piperazinamido where the substituent is selected from the group consisting of 4-N-carboxymethyl, 4-N-carboxamidomethyl, 4-N-(5-hydroxyethylenoxyethylene) and 4-N-P-toluenesulfonamido, pyrrolidinamido, piperidinamido and substituted piperidinamido where the substituent is selected from the group consisting of 4-hydroxy, 4-carbamyl, 4-carboxyl groups.

Table 4 below lists exemplary compounds defined by the single letter amino acid sequence abbreviation format. The compound ID number cross-references compounds herein.

TABLE 4

COMPOUNDS DESCRIBED BY AMINO ACID SEQUENCE AND SUBSTITUENT GROUPS

| SEQ ID NO: | FORMULA[1] | X | Z[2] | COMPOUND ID NO: |
|---|---|---|---|---|
|  | X L D F Z | phenylacetyl | 4-N(carboxymethyl)piperazinamide[9] | 1111.06 |
|  | X L D F Z | phenylacetyl | 4-(thiadioxo)piperidinamide[10] | 1111.03 |
|  | X L D F Z | phenylacetyl | 4-(carbamyl)piperidinamide[11] | 1111.05 |
|  | X L D F Z | phenylacetyl | morpholinamide | 1051.01 |
|  | X L D F Z | phenylacetyl | 4-(carboxy)piperidinamide | 1111.04 |
|  | X L D F p | pyridine-4-carbonyl | amide | 951.20 |
|  | X L D Y p | phenylacetyl | amide | 896.61 |
|  | X L D F Z | phenylacetyl | 4-hydroxypiperidinamide | 1070.02 |
|  | X L D F Z | phenylacetyl | piperazinamide | 1051.02 |
|  | X L D F Z | phenylacetyl | 4-N-(5-hydroxyethyloxyethylene)-piperazinamide[12] | 1111.07 |
|  | X L D F Z | phenylacetyl | thiomorpholinamide | 1111.02 |
|  | X L D F p | pyridine-3-acetyl | amide | 951.22 |
| 4 | X L D Y P | phenylacetyl | amide | 1036.01 |
|  | X L D F P | phenylacetyl | 4-N-(p-toluenesulfonamido)-piperidinamide | 1111.01 |
|  | X L D F Z | phenylacetyl | 4-N-(carboxamidomethyl)piperazinamide | 1111.09 |
|  | X L D Y Z | phenylacetyl | morpholinamide | 1045.02 |
|  | X L D F Z | phenylacetyl | 4,4-N,N-(dimethyl)-piperaziniumamide iodide | 1111.08 |
|  | X L D F p | phenylacetyl | amide | 896.52 |
|  | X L D L Z | phenylacetyl | morpholinamide | 997.20 |
|  | X L D F Z | phenylacetyl | pyrrolidinamide | 951.15 |
|  | X L D F Z | phenylacetyl | piperidinamide | 951.14 |
|  | X L D F p | anilinocarbonyl | amide | 896.62 |
|  | X J D F p | phenylacetyl | amide   J = cyclohexyL-Ala[5] | 1160.01 |
| 5 | X L D F P Z | phenylacetyl | peptide-substituted tetraethylene-pentaamine[3] | 1058.01 |
|  | X L D F p | pyridine-3-carbonyl | amide | 896.55 |
|  | X L D F Z | phenylacetyl | 3,4-dihydroxypyrrolidinamide | 1070.01 |
|  | X L D F Z | phenylacetyl | 2-(hydroxymethyl)prolinamide | 951.17 |
|  | X L D W p | phenylacetyl | amide | 896.60 |
|  | B Z F L D F p | B = biotinoyl | Z = ε-amidocaproyl   amide | 1019.01 |
|  | X L D V p | phthalimido | amide | 896.51 |
|  | Z X F L D F p | ε-amidocaproyl | Z = Europium label[4]   amide | 1092.01 |
|  | X L D V p | phenylacetyl | amide | 896.39 |
|  | X L D Z | phenylacetyl | N-[1-(carboxamidomethyl)-caprolactam-3-yl]amide | 1057.06 |
|  | X L D J p | phenylacetyl | amide   J = homo-Phe[5] | 1062.03 |
|  | X L D F Z | 3,4-dihydroxyphenylacetyl | piperidinamide | 1019.01 |
|  | X L D F p | benzoyl | amide | 896.28 |
|  | X L D V p | pyridine-3-carbonyl | amide | 896.42 |
|  | X L D J p | phenylacetyl | amide   J = Phenyl-Gly[5] | 896.69 |
|  | X L D F p | 3-quinolinecarbonyl | amide | 951.05 |
|  | X L D F p | 1,2,3,4-tetrahydroquinazoline-2,4-dione-3-yl | amide | 896.63 |
|  | X L D Z | phenylacetyl | 6,7-fused ring Lactam[7] | 1026.05 |
|  | X J D F p | phenylacetyl | amide   J = Nle[5] | 1160.02 |
|  | P L D F p | free amine | amide | 951.12 |
|  | X L D Z | phenylacetyl | N-[(1-carboxaminomethyl)-2-oxo-tetrahydroquinolin-3-yl]amide | 997.11 |
| 6 | X F L D L Z | GlcNAc—O—(CH$_2$)$_5$—C(O) | piperidinamide | 1063.01 |
|  | X L D J p | phenylacetyl | amide   J = p-nitro-Phe[5] | 896.68 |
| 7 | X L D V P | benzoyl | amide | 896.35 |
|  | F L D F p | acetyl | amide | 951.42 |
|  | X L D F p | benzyloxycarbonyl | amide | 1056.01 |
|  | X L D F Z | (5-phenyl)hydantoinyl | piperidinamide | 1047.01 |
|  | X L D F p | pyrazolecarbonyl | amide | 951.03 |
|  | F L D F p | acetyl | amide | 896.27 |
|  | X L D Z | phenylacetyl | N-(2-oxo-tetrahydroquinolin-3-yl)amide | 997.08 |
|  | X L D Z | phenylacetyl | N-(caprolactam-3-yl)-amide | 1043.02 |
|  | X L D F Z | phenylacetyl | propanolamide | 1051.05 |
|  | X L D Y Z | 4-pyridinecarbonyl | piperidinamide | 1045.01 |
|  | X L D Z | phenylacetyl | N-[1-(2-N-morpholinylethyl)-2-oxo-tetrahydroquinoline-3-yl]amide | 997.18 |
| 8 | X L D V P | pivaloyl | amide | 926.01 |
|  | X L D V p | benzoyl | amide | 926.02 |

TABLE 4-continued

COMPOUNDS DESCRIBED BY AMINO ACID SEQUENCE AND SUBSTITUENT GROUPS

| SEQ ID NO: | FORMULA[1] | X | Z[2] | COMPOUND ID NO: |
|---|---|---|---|---|
|  | X L D Z | phenylacetyl | benzylamide | 997.02 |
|  | X J D F p | benzoyl | amide    J = cyclohexyl-Ala[5] | 896.31 |
|  | X L D Z | phenylacetyl | N-D-(caprolactam-3-yl)amide | 1043.01 |
|  | X L D S p | phenylacetyl | amide | 1042.23 |
|  | X L D Y Z | phenylacetyl | t-butylester | 1040.02 |
|  | X L D V p | phenylpropionyl | amide | 896.40 |
|  | X L D Z | phenylacetyl | N-(2-N-morpholinyl)ethylamide | 997.03 |
|  | X J D V p | benzoyl | amide    J = cyclohexyl-Ala[5] | 896.34 |
|  | F L D V p | free amine | amide | 926.04 |
|  | X L D F p | 2-pyrazinecarbonyl | amide | 951.02 |
|  | X L D G Z | phenylacetyl | morpholinamide | 997.16 |
|  | X L D V p | 2,3-dimethylbenzoyl | amide | 896.38 |
|  | X L D V p | 3,4-dimethylbenzoyl | amide | 896.37 |
|  | X L D V p | pyridine-2-carbonyl | amide | 896.54 |
|  | X L D Z | phenylacetyl | Z=N-[(N-cyclohexyl)butyrolactam-3-yl]amide | 1057.02 |
|  | X L D Z | phenylacetyl | N-(1-iso-butyl-2-oxo-tetrahydro-quinolin-3-yl)amide | 997.10 |
|  | X L D F Z | benzyl | piperidinamide | 1033.01 |
|  | f L D V p | free amine | amide | 926.05 |
|  | X L D V p | cyclohexanecarbonyl | amide | 896.49 |
|  | X L D V p | 2,6-dimethylbenzoyl | amide | 896.36 |
|  | X L D F p | 2-quinolinecarbonyl | amide | 951.06 |
|  | X L D V p | 3-methylvaleroyl | amide | 896.46 |
|  | X L D Z | phenylacetyl | N-(tetrahydroisoquinolin-3-yl)amide | 997.09 |
|  | p L D F p | free amine | amide | 951.11 |
|  | X L D F p | 8-quinolinesulfonyl | amide | 951.07 |
|  | X L D F Z | phenylacetyl | n-butylamide | 1051.03 |
|  | X L D V p | 4-methylvaleroyl | amide | 896.47 |
|  | X L D Y | phenylacetyl | t-butyl ester | 1040.01 |
|  | X L D Z | phenylacetyl | benzylhydrylamide |  |
|  | X L D F p | p-bromophenylacetyl | amide | 951.08 |
|  | I L D F p | free amine | amide | 896.26 |
| 9 | X L D F P Z | phenylacetyl | decylamide | 1068.04 |
| 10 | I L D V P I L D V P | free amine | amide | 926.28 |
|  | X J D F p | benzylamide | amide    J = dicarboxy-Leu[5] | 1034.01 |
|  | X L D V p | cyclohexaneacetyl | amide | 896.48 |
|  | X L D Z | phenylacetyl | N'-t-Boc-hydrazine | 997.13 |
| 11 | I L D F P | free amine | amide | 926.12 |
|  | X L D V p | 1-naphthoyl | amide | 896.43 |
|  | X L D V p | cyclohexanepropionyl | amide | 896.45 |
|  | X L D Z | phenylacetyl | N'-benzyl-N'-cyclopenanecarbonylhydrazine | 997.15 |
|  | F J D F p | free amine | amide    cyclohexyl-Ala[5] | 896.30 |
|  | i L D V p | free amine | amide | 926.03 |
|  | I L D V p | free amine | amide | 886.10 |
|  | I J D F p | free amine | amide    cyclohexyl-Ala[5] | 896.29 |
|  | X L D V p | cinnamoyl | amide | 896.41 |
| 3 | G P E I L D V P S T | free amine | free acid | 872.01 |
| 12 | X L D F P Z | phenylacetyl | HN(CH$_2$)$_5$C(O)NHC$_{18}$H$_{37}$ | 1068.01 |
|  | X L D F | phenylacetyl | amide | 997.12 |
|  | X L D F Z | phenylacetyl | N-(4-decoyloxy)piperidinamide | 1068.06 |
|  | X L D F Z | phenylacetyl | N-(4-stearoyloxy)piperidinamide | 1068.05 |
|  | L D V | acetyl | amide | 926.30 |
|  | X L D Z | phenylacetyl | hydrazine |  |
|  | X L D V p | adamantanecarbonyl | amide | 896.50 |
|  | X L D V p | 2-naphthoyl | amide | 896.44 |
| 13 | I L D V P | free amine | amide | 886.03 |
| 14 | I L D V P | free amine | free acid | 886.05 |
|  | L D F | acetyl | amide | 926.32 |
|  | X D L F p | phenylacetyl | amide | 1066.02 |
| 15 | S F D F S | acetyl | amide | 951.46 |
|  | I J D V p | free amine | amide    J = cyclohexyl-Ala[5] | 896.32 |
|  | X L D F p | 4-bromophenylsulfonyl | amide | 951.10 |
|  | L D F Z | free amine | piperidinamide | 1047.09 |
|  | J D F Z | J = iso-butyloxycarbonyl | piperidinamide | 1027.04 |

TABLE 4-continued

COMPOUNDS DESCRIBED BY AMINO ACID SEQUENCE AND SUBSTITUENT GROUPS

| SEQ ID NO: | FORMULA[1] | X | Z[2] | COMPOUND ID NO: |
|---|---|---|---|---|
| | L D F | free amine | amide | 926.31 |
| | L D V | free amine | amide | 926.29 |
| | X L D F p Z | phenylacetyl | linker arm-biotin[8] | 896.61 |

[1]A lower case letter in bold-faced type is used to designate a D-isomer of the L-amino acid residue designated in single letter code by the same capitol letter. Thus, p = D-proline; f = D-phenylalanine; i-D-isoleucine. The N-terminal α-amine is substituted as shown or indicated to be a "free amine".
[2]The state of the C-terminal carboxyl of Z as an "amide" (—$NH_2$) or "free acid" is noted as appropriate.
[3]Z is an amide formed between the C-terminal Pro carboxyl and a tetraethylenepentaamine containing four N-phenylacetyl-LDFP peptides amide-bonded thereto.
[4]Diethylenetriaminepentaacetatoeuropium (II) amide-bonded to Z.
[5]"Homo—Phe" = homophenylalanine; "phenyl—Gly" = phenylglycine; "p-nitro—Phe" = p-nitrophenylalanine; β-carboxy—Asp = β-carboxyaspartic acid; "cyclohexyl—Ala" = cyclohexylalanine; and "dicarboxy—Leu" = dicarboxyleucine, Nle = norleucine
[6]Relative activites of about one-tenth or less than that exhibited by the peptides of SEQ ID NO:3 are assigned a potency activity of zero.

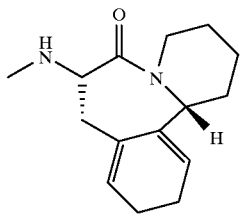

Amide formed from 1,6-hexanediamine amide-bonded to biotin.

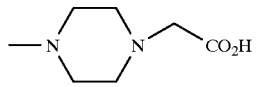

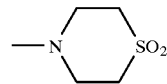

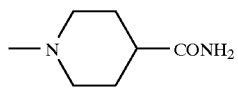

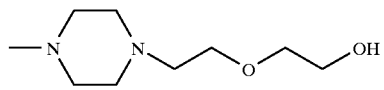

Figure 2:
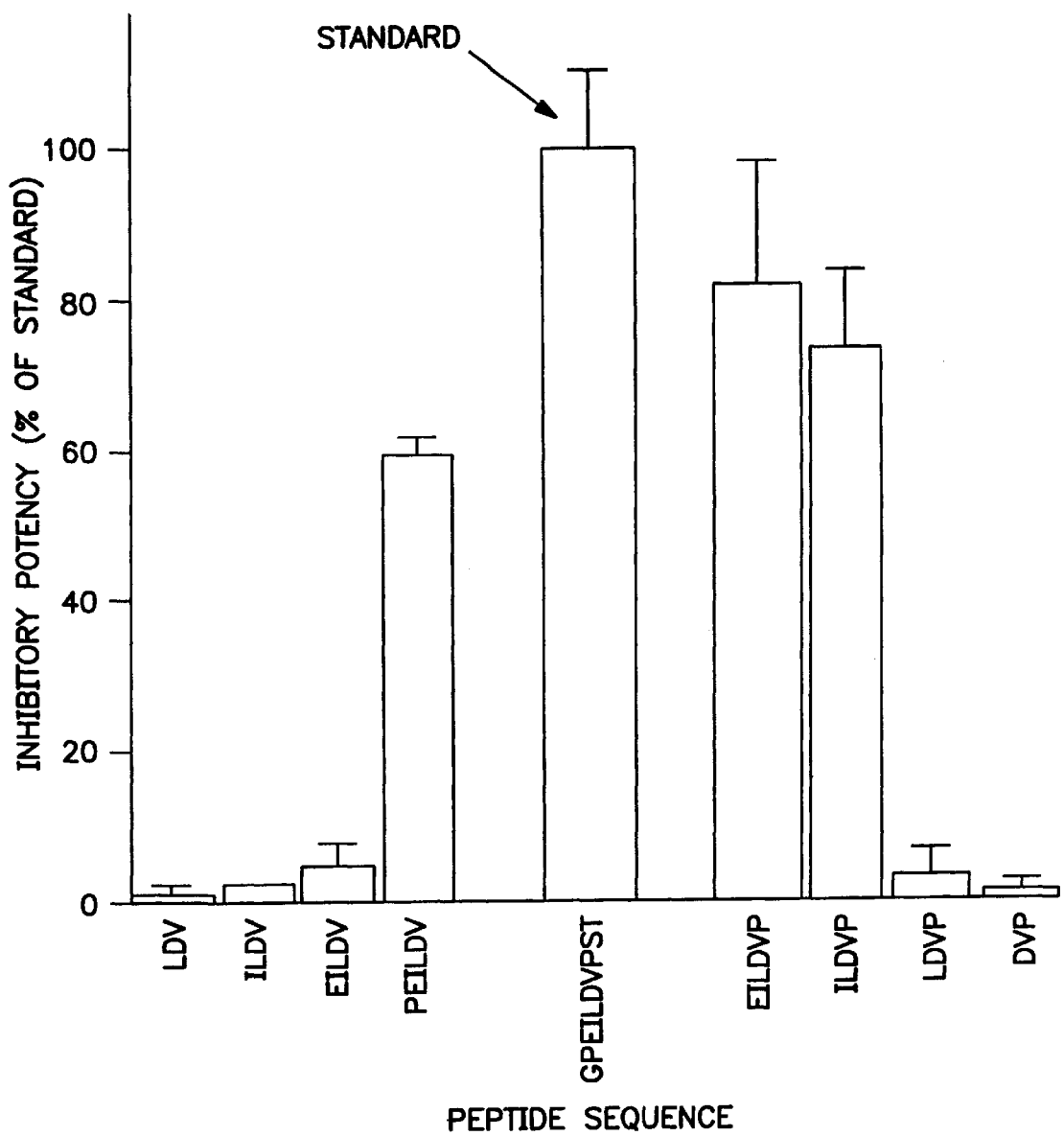
FIG. 2 is a graph with data obtained and expressed similarly to those of FIG. 1. Here, binding inhibition by further, still shorter deletion compounds, is illustrated.
Figure 3:
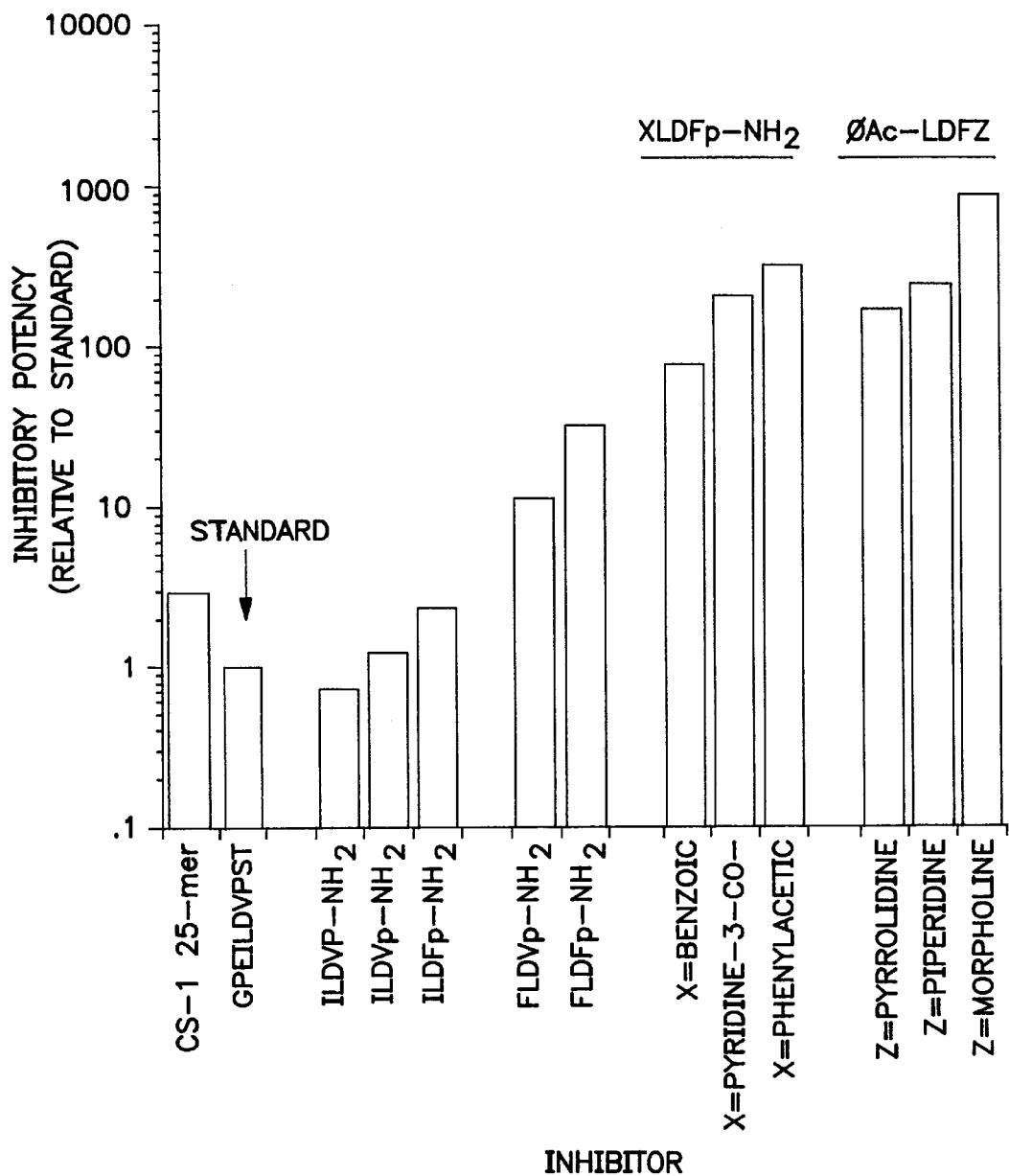
FIG. 3 is another graph of binding data obtained as discussed in FIG. 1. This graph utilizes an ordinate that is on a log scale. These data are arranged into five groups and are again shown relative to the indicated Standard compound (SEQ ID NO:3), with D-proline being shown as "p". The data of the right-hand-most two groups illustrate the effects of three different X groups on a single indicated compound and of three Z groups in which X is phenyl acetyl (φAc) and Z is as shown, respectively.

The data shown in FIGS. 1, 2 and 3 also illustrate the unexpected binding inhibitions exhibited by contemplated compounds relative to other compounds of the art. The compound sequences are shown using single letter code.

For example, FIG. 1 illustrates results of relative in vitro binding inhibition studies carried out using the CS-1 (SEQ ID NO:1) compound, the CS-1 compound B12 portion (CS-1 B12; SEQ ID NO:2), the 10-mer compound used as a standard above, elsewhere herein and in the art (SEQ ID NO:3), and several deletion analogues of the B12 compound, each containing the Leu-Asp sequence. N-Terminal deletion analogues are shown to the left of the standard 10-mer, whereas C-terminal deletions are shown to the right of the 10-mer. As is seen, the CS-1 compound is about three times more potent an inhibitor than is B12, the 10-mer or a 9-mer deletion analogue of the 10-mer. Those latter three compounds were all more potent than the other B12-related compounds.

The similarly obtained data of FIG. 2 illustrate binding inhibition results obtained using deletion analogues of the standard 10-mer compound. Here, deletions made at both N- and C-termini are shown to the left of the standard 10-mer to isolate the Leu-Asp-Val sequence at the C-terminus, whereas those shown to the right of the standard 10-mer isolate the Asp-Val-Pro sequence. These compounds and those of FIG. 1 had free N-terminal amine groups and C-terminal carboxyl groups.

The data of FIG. 3 were similarly obtained, but are shown on a log scale so that all of the data could be accommodated. The data of FIG. 3 are shown in five groups, from left to right.

The first group show data for CS-1 compound and the 10-mer standard. The next three bars shown data for a pentamer C-amide having the sequence including Leu-Asp-Val of the native CS-1 compound, the enhanced effect of using D-proline instead of the native L-proline, and then the enhancement by use of phenylalanine and D-proline in place of valine and D-proline. The next two bars illustrate the further enhancement obtained over the three previous compounds obtained when a cyclic ring-containing X group, here phenylalanine as the free amine, was used to replace the isoleucine of the native sequence. The fourth group of bars illustrates the effects of three X groups of formula I as compared to the phenylalanine group, using the better compound sequence of the two adjacent sequence [XLDFp-NH$_2$]. Phenylacetyl (φAc) was used as an X group in the last three compounds where the D-proline Z group of formula I was varied using three cyclic amines (NCy$^1$). As is seen, use of a morpholinamide group as Z, along with phenylacetyl as X and phenylalanine as Xaa of formula I, provided the greatest potency in these studies.

Thus, the data of FIG. 3 show inhibitory potencies spanning about three orders of magnitude from the standard 10-mer and compounds of the art, through contemplated compounds that exhibit about a 10-fold enhancement in potency over that standard to those contemplated compounds exhibiting about a 50-fold to about 100-fold enhancement in potency and those exhibiting an enhancement in potency of up to about 1000-fold.

In addition to being more potent than the CS-1 or standard 10-mer compounds, a contemplated inhibitor compound, particularly a compound with non-naturally occurring terminal groups such as N-phenylacetyl and C-morpholinamide or D-Pro-NH$_2$, is relatively more stable in serum that is the CS-1 compound. Thus, the inhibitor compounds N-phenylacetyl-Leu-Asp-Phe-morpholinamide and N-phenylacetyl-Leu-Asp-Phe-D-Pro-NH$_2$ exhibited no loss of potency after 24 hours in PBS at 7.2–7.4 that also contained 10 percent mouse or human serum. Contrarily, the CS-1 compound lost its potency in less than one hour under the same conditions.

B. Syntheses

The contemplated inhibitors are compounds or compound derivatives, and as such, can be readily synthesized using well known synthetic methods. See for example, Stewart, J. M. and J. D. Young, *Solid Phase Peptide Synthesis*, Pierce Chemical Company, Rockford, Ill., (1984) and M. Bodansky, *Peptide Chemistry, A Practical Textbook*, 2$^{nd}$ Edition, Springer-Verlag, New York, (1993) which are herein incorporated by reference. Specific synthetic examples are provided hereinafter.

Solid phase synthesis was used for those materials having a C-terminal amino acid amide or free acid residue. Thus, the N-protected, C-terminal residue was linked to a solid support having a benzhydrylamine substituent. Fmoc amine blocking groups were used in these syntheses, although t-Boc, CBZ or other blocking groups can also be used with other solid supports. Upon deblocking the Fmoc group with piperidine, another residue was coupled. That coupling was followed by further deblocking, coupling, deblocking etc. steps until a solid phase-linked compound of desired sequence was prepared. As appropriate to each compound, an N-terminal X group was added after a final N-deblocking step or sometimes pre-coupled to the N-terminal residue. The desired compound and any accompanying functional group protecting groups were removed from the solid support by reaction with trifluoroacetic acid (TFA). This procedure results in a C-amide-terminated compound when a benzhydrylamine solid support is used.

Contemplated compounds can also be prepared using t-Boc N-protecting groups and another solid support, or a benzylamino-substituted solid support to which a P-hydroxymethylphenylcarboxyl (PAM) group is first reacted with the amine of the support to form a carboxamide. The hydroxyl group is then used to form an ester link to the first compound and standard t-Boc synthetic technology is thereafter followed. Reaction of the completed, deprotected solid phase-linked compound with ammonia provides the C-terminal amide compound discussed before, whereas reaction with another amine such as morpholine or piperidine or other NCy$^1$ or NCy$^2$ amine provides a compound whose C-terminal residue is amide-bonded to an NCy$^1$ or NCy$^2$ group. Reaction of a deprotected, PAM-linked compound with hydroxide provides the corresponding C-terminal carboxyl group.

In other embodiments, liquid phase compound syntheses were utilized. For example, morpholine or other NCy$^1$ or NCy$^2$ group was coupled in solution to a contemplated C-terminal, t-Boc-protected residue using a carbodiimide. The t-Boc protecting group was removed with acid, a further t-Boc-protected residue added, followed by deblockings and further additions. The N-terminal X group such as phenylacetic acid was added after the last t-Boc removal step and the synthesis was completed, except for deprotecting the Asp residue. That step was carried out by catalytic hydrogenation where a benzyl ester protecting group was used.

Regardless of the synthetic method used, an inhibitor compound is typically recovered and purified prior to use. Recovery and purification techniques are well known and will not be dealt with here.

C. Mass Spectroscopy

Mass spectroscopy data confirmed the expected molecular weight of exemplary compounds. The data was obtained using fast atom bombardment mass spectrometry (FAB), electrospray mass spectrometry (Electrospray), or matrix assisted laser desorption mass spectroscopy (MALDI-TOF-MS).

Briefly, FAB was done using a VG ZAB-VSE double focusing high resolution mass spectrometer equipped with a cesium ion gun. The mass spectrometer was manually tuned to a resolution of 2000 (10% valley definition) with amplifier and multiplier gains of a million (300V). A 35 kev cesium ion beam was used as the fast ion beam and the accelerating voltage of the desorbed ions was 8 kV. The mass spectra were acquired using CSI for calibration; typically ten spectra were accumulated and averaged. Spectra were recorded with a Digital VAX station 3100 and the peaks were automatically centroided. A flat FAB sample holder was used. Standards having 98% or better purity were used. In a representative experiment, 10.0 micrograms of the sample in methanol was applied to 2.0 microliters of the matrix and the solvent was evaporated. The probe was inserted into the mass spectrometer and spectra accumulated and averaged.

Electrospray mass spectroscopy was conducted on a API III PERKIN ELMER SCIEX triple-quadrupole mass spectrometer. Samples were introduced into the analyzer at a rate of 4.0 μl/minute. The positive ions generated by the ion evaporation process entered the analyzer through an interface plate and a 100 μm orifice, while the declustering potential was maintained between 50–250 V (typically 100V) to control the collision energy of the entering ions.

MALDI-TOF-MS spectroscopy was performed on a Vesdec Inc. Voyager Biospectrometry workstation. Matrix Assisted ionization of a compound consists of mixing a dilute solution of a compound with a large excess of an appropriate matrix material. The sample is placed in the mass spectrometer and irradiated with a laser. The matrix gives off absorbed light energy which causes vaporization of the compound in the mass spectrometer. In a representative experiment, the compound is prepared in a water and TFA solvent and appropriately diluted. The matrix was the Alpha cyano-4-hydroxy-cinnamic acid, gentisic acid or sinapinic acid. The laser was an N2 laser.

The mass spectroscopy data of exemplary compounds is shown in Table 5. The compound ID number cross-references compounds herein.

TABLE 5

Compound ID Number and Mass Spectroscopy Data

| Compound ID Number | Molecular ion |
|---|---|
| 1111.06 | 638 (MH$^+$) |
| 1111.03 | 629 (MH$^+$) |
| 1190.03 | 652 (MH$^+$) |
| 1111.05 | 622 (MH$^+$) |
| 1051.01 | 581 (MH$^+$) |
| 896.61 | 624 (MH$^+$) |
| 1070.02 | 596 (MH$^+$) |
| 1190.02 | 636 (MH$^+$) |
| 1111.07 | 668 (MH$^+$) |
| 1051.02 | 581 (MH$^+$) |
| 1036.01 | 624 (MH$^+$) |
| 951.22 | 610 (MH$^+$) |
| 1111.01 | 734 (MH$^+$) |
| 1111.09 | 637 (MH$^+$) |
| 1190.07 | 644 (MNa$^+$) |
| 896.52 | 608 (MH$^+$) |
| 1045.02 | 597 (MH$^+$) |
| 997.20 | 551 (MH$^+$) |
| 896.62 | 610 (MH$^+$) |
| 951.14 | 579 (MH$^+$) |
| 951.20 | 596 (MH$^+$) |
| 1111.08 | 608 (MH—I)$^+$ |
| 1160.01 | 670 (MNa$^+$) |
| 1190.04 | 582 (MH$^+$) |
| 951.17 | 595 (M + 2H$^+$) |
| 896.60 | 647 (MH$^+$) |
| 951.15 | 565 (M$^+$) |
| 896.55 | 596 (MH$^+$) |
| 1111.10 | 596 (MH$^+$) |
| 1057.06 | 532 (MH$^+$) |
| 1062.03 | 622 (MH$^+$) |
| 1019.01 | 611 (MH$^+$) |
| 951.12 | 587 (MH$^+$) |
| 896.69 | 594 (MH$^+$) |
| 951.05 | 645 (MH$^+$) |
| 1026.05 | 577 (MH$^+$) |
| 1160.02 | 608 (MH$^+$) |
| 896.39 | 561 (MH$^+$) |
| 997.11 | 566 (M$^+$) |
| 896.28 | 616 (MNa$^+$) |
| 896.63 | 636 (MH$^+$) |
| 1063.01 | 948 (MH + Na$^+$) |
| 896.68 | 661 (MH$^+$) |
| 951.42 | 701 (MNa$^+$) |
| 1047.01 | 620 (MH$^+$) |
| 1056.01 | 625 (MH$^+$) |
| 951.03 | 585 (MH$^+$) |
| 1043.02 | 497 (MNa$^+$) |
| 1051.05 | 590 (MNa—H)$^+$ |
| 997.08 | 509 (MH$^+$) |
| 997.18 | 644 (MNa$^+$) |
| 951.02 | 618 (MNa$^+$) |
| 997.02 | 455 (MH$^+$) |
| 1043.01 | 475 (MH$^+$) |
| 896.27 | 638 (MH$^+$) |
| 896.72 | 570 (MNa$^+$) |
| 1040.02 | 607 (MNa$^+$) |
| 896.54 | 548 (MH$^+$) |
| 997.03 | 477 (M$^+$) |
| 1047.05 | 508 (MH$^+$) |
| 896.31 | 635 (MH$^+$) |
| 926.02 | 547 (MH$^+$) |
| 997.16 | 513 (MNa$^+$) |
| 896.49 | 538 (MH$^+$) |
| 951.06 | 646 (MH$^+$) |
| 997.10 | 566(MH$^+$) |
| 1047.06 | 656 (MNa$^+$) |
| 951.08 | 709 (MNa$^+$) |
| 896.37 | 574 (M$^+$) |
| 896.47 | 562 (MNa—H)$^+$ |
| 997.09 | 480 (M$^+$) |

TABLE 5-continued

Compound ID Number and Mass Spectroscopy Data

| Compound ID Number | Molecular ion |
|---|---|
| 1057.04 | 553 (MH$^+$) |
| 1051.04 | 638 (MH$^+$) |
| 1068.04 | 770 (MH + Na$^+$) |
| 926.04 | 590 (MH$^+$) |
| 926.03 | 556 (MH$^+$) |
| 886.03 | 556 (MH$^+$) |
| 997.15 | 566 (MH$^+$) |
| 1067.01 | 778 (MH + Na$^+$) |
| 926.05 | 590 (MH$^+$) |
| 1068.01 | 995 (MNa$^+$) |
| 1067.02 | 688 (MH + Na$^+$) |
| 1068.05 | 864 (MH$^+$) |
| 1068.06 | 774 (MNa$^+$) |
| 997.12 | 512 (MH$^+$) |
| 1190.01 | 636 (MH$^+$) |
| 1068.07 | 720 (MNa$^+$) |
| 1068.08 | 686 (MNa$^+$) |
| 1068.09 | 770 (MNa$^+$) |
| 1068.10 | 799 (MH + Na$^+$) |
| 1068.11 | 805 (M + 2H$^+$) |
| 1068.12 | 883 (MH + Na$^+$) |
| 1068.13 | 743 (MNa$^+$) |
| 1068.14 | 799 (MNa$^+$) |
| 1190.05 | 644 (MNa$^+$) |
| 1190.06 | 644 (MNa$^+$) |

D. Prodrug Compounds

Prodrug compounds are transformed in vivo from compounds that do not necessarily bind the VLA-4 receptor in vitro to compounds having such binding activity in vivo. Chemical modifications of drugs that make prodrugs are known in the art and include, for example, esters of carboxylic acids or carboxyamide phosphonate groups. Moreover, the synthesis of prodrugs is by well known methods and will not be detailed here. See, for example, Bundraard, *Design of Prodrugs*, Elsevier Science Pub. Co., New York (1985), and *Prodrugs as Novel Drug Delivery Systems Symposium*, 168th Annual Meeting, American Chemical Society, Atlantic City, N.J., Eds. T. Higuchi and V. Stella, ACS Symposium Serries 14, 1975, which are herein incorporated by reference.

E. Compositions and Process

As noted elsewhere, immune system leukocyte effector or inflammatory cells such as monocytes, T cells and eosinophils bear the VLA-4 receptor on their cell surfaces. Those cells bind to the CS-1 portion of fibronectin present on the surfaces of vascular endothelial cells at an early step in inflammatory cell emigration (trafficking) from the blood in the tissues. These inflammatory cells immunoreact with monoclonal antibody P4C2 discussed in Wayner et al., *J. Cell. Biol.*, 109:1321–1330 (1989), Wayner WO 98/12809, Hemler et al, *J. Biol. Chem.*, 262(24):11478–11485 (1987) and monoclonal antibody HP1/2 of Lobb WO 93/13798 published Jul. 22, 1993.

Once in the tissues, the inflammatory cells enhance the inflammatory response through one or more of several mechanisms. In one mechanism, cytokines and chemoattractants reactants such as interleukin-1β (IL-1β), IL-2, tumor necrosis factor α (TNFα) and lymphocyte-derived chemotactic factor are released by the inflammatory cells and cause further inflammatory cells to emigrate to the area. In another mechanism, the inflammatory cells mis-recognize cells of the mammal with the inflammatory disease state as being non-self and attack those cells, killing them. These and other mechanisms of immunoinflammatory response enhancement are well known to skilled workers and need not be further elaborated upon here. The fibronectin CS-1 compound thus mediates inflammatory disease states by assisting emigration of inflammation-enhancing effector cells from the blood into the tissues.

A contemplated inhibitor compound blocks binding between CS-1 and VLA-4, and inhibits the resulting emigration of inflammatory cells bearing VLA-4 receptors into the tissues, and the exacerbation of the inflammatory condition that results. That inhibition of emigration of inflammatory cells results in a reduction of the fibronectin CS-1/VLA-4-mediated inflammatory response caused by those inflammatory cells, and thereby reduces the observed inflammation.

Particular inflammatory disease states that are mediated by CS-1 and VLA-4, and in which a contemplated inhibitor compound can diminish inflammation are quite broad. Illustrative of those types of inflammation are asthma, arthritic conditions such as rheumatoid arthritis and osteoarthritis, allograft rejection, various types of skin inflammation, and demyelinating diseases of the central nervous system.

Specific pathological inflammatory conditions in which expression of CS-1 has been found to be implicated and where no such expression is observed in absence of a pathological condition (i.e., in normal tissue) include: rheumatoid arthritis (synovium), osteoarthritis (synovium), skin psoriasis, kidney transplant, asthmatic lung, and lymph node high endothelial venules (HEV) in humans, as well as in the gut of monkeys infected with SIV and those having inflammatory bowel disease, rabbits having asthmatic lungs and heart transplants, mouse brain in experimental autoimmune encephalomyelitis (EAE) and (DTH in delayed type hypersensitivity (DTH), and the joints of rats with induced arthritis.

VLA-4 is expressed on mononuclear leukocytes, T cells, B cells and monocytes, as well as eosinophils. Since a contemplated inhibitor compound acts by binding to VLA-4, any inflammatory disease state which involves the aforementioned cells may be treated using the inhibitor compounds of the present invention. For example, inflammatory diseases states such as allergy, arthritis, asthma, atherosclerosis, colitis, diabetes, inflammatory bowel disease, kidney inflammation, skin inflammatory diseases multiple sclerosis, restenosis, and transplantation are VLA-4 dependent inflammatory diseases and can be treated by inhibitor compounds of the present invention.

Although potency is used to screen inhibitor compounds, the compound efficacy is the relevant parameter for clinical applications. Efficacy connotes the property of a drug to achieve a desired response. A compound having relatively low potency but more selectivity can be the clinically preferred compound. Thus, a compound that binds to the VLA-4 receptor, but does not bind tighter than the CS-1 25-mer compound present in fibronectin, and has efficacy in vivo can be used in a pharmaceutical composition. See, for example, *Remington's Pharmaceutical Sciences,* 17th ed., Mack Publishing Company, Easton, Pa. (1985), which is incorporated herein by reference.

A pharmaceutical composition containing a contemplated inhibitor compound dissolved or dispersed in a pharmaceutically acceptable carrier or diluent that is preferably aqueous is also contemplated for use in treating a CS-1/VLA-4-mediated inflammatory disease state such as those discussed before. Such a composition contains an effective amount of a contemplated compound. In an embodiment, such a composition contains the CS-1/VLA-4 binding-inhibiting (an inflammation-reducing) amount of a before-discussed, contemplated inhibitor compound.

Thus, the present invention also contemplates a pharmaceutical composition that can be used in treating one or more of the aforementioned conditions. A contemplated pharmaceutical composition is comprised of a before-described inhibitor compound that inhibits the binding interaction between VLA-4-containing leukocytes and the fibronectin compound CS-1 portion expressed on endothelial cell surfaces, which compound is dissolved or dispersed in a pharmaceutically acceptable diluent in a binding inhibitory (inflammation-reducing) amount. A contemplated pharmaceutical composition is suitable for use in a variety of drug delivery systems. For a brief review of present methods for drug delivery, see, Langer, *Science,* 249:1527–1533 (1990).

For a contemplated pharmaceutical composition, the dose of the compound varies according to, e.g., the particular compound, the manner of administration, the particular disease being treated and its severity, the overall health and condition of the patient, and the judgment of the prescribing physician or veterinarian. A pharmaceutical composition is intended for parenteral, topical, oral or local administration, such as by aerosol or transdermally, for prophylactic and/or therapeutic treatment. A pharmaceutical composition can be administered in a variety of unit dosage forms depending upon the method of administration. For example, unit dosage forms suitable for oral administration include powder, tablets, pills, capsules and dragees.

A pharmaceutical composition also is administered intravenously. Thus, a composition for intravenous administration is particularly contemplated that comprises a solution of a contemplated inhibitor compound dissolved or dispersed in a pharmaceutically acceptable diluent (carrier), preferably an aqueous carrier. A variety of aqueous carriers can be used, e.g., water, buffered water, 0.9 percent saline, buffered aqueous ethanol solutions and the like. These compositions can be sterilized by conventional, well known sterilization techniques, or can be sterile filtered. The resulting aqueous solutions can be packaged for use as is, or lyophilized, the lyophilized preparation being combined with a sterile aqueous solution prior to administration. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of inhibitor compound utilized is usually at or at least about 0.0001 percent to as much as about 0.1 percent by weight and is selected primarily by fluid volumes, viscosities, etc., in accordance with the particular mode of administration selected.

Thus, a typical pharmaceutical composition for intravenous infusion can be made up to contain 250 ml of sterile Ringer's solution normal saline or PBS, and about 0.25 mg to about 25 mg of the inhibitor compound. Actual methods for preparing parenterally administrable compounds are known or apparent to those skilled in the art and are described in more detail in for example, Remington's, supra.

For solid compositions, conventional nontoxic solid diluents (carriers) may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95 percent of active ingredient, that is, a before-described inhibitor compound preferably about 20 percent (see, Remington's, supra), preferably using an enteric coating to pass a solid dose through the stomach and into the intestine.

For aerosol administration, a contemplated inhibitor compound is preferably supplied in solution such as aqueous ethanol or DMSO solution along with a surfactant and propellant. Typical percentages of an inhibitor compound are about 0.0001 percent to about 0.1 percent by weight, and preferably about 0.0001 percent to about 0.001 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve. A pump-activated spray using air as propellant (atomizer or nebulizer) is also contemplated.

For example, for the treatment of asthma in rabbits, the dose of a contemplated compound is in the range of about 1 to 100 mg/day for a 2–3 kg animal. For a human asthma patient, that dose is in the range of about 1 to about 100 mg/day for a 70 kg patient. Administration for asthma is typically by aerosol from a nebulizer. Ideally, therapeutic administration should begin as soon as possible after the attack begins.

A pharmaceutical composition embodiment is the inhibitor compound of the present invention and a liposome suitable for pharmaceutical use. Examples of suitable liposomes include those disclosed in WO9421281, WO9421235, U.S. Pat. No. 5,225,212, or WO8606959 which are herein incorporated by reference.

A pharmaceutical composition containing an inhibitor compound can be administered for prophylactic and/or therapeutic treatments. In therapeutic applications, a composition is administered to a patient already suffering from a disease, as described above, in an amount sufficient to inhibit binding between VLA-4-expressing leukocytes and endothelial cells that express the CS-1 compound portion; i.e., reduce inflammation and thereby at least partially arrest the symptoms of the disease and its complications. An amount adequate to accomplish this is defined as "therapeutically effective dose", or a "binding-inhibiting amount" or an "inflammation-reducing amount". Amounts effective for this use depend on the severity of the disease and the weight and general state of the patient, but generally range from about 1 mg/kg to about 500 mg/kg of inhibitor compound per day, with dosages of from about 1 mg/kg to about 10 mg/kg of a compound per day being more commonly used.

In prophylactic applications, a composition containing a contemplated compound is administered to a patient susceptible to or otherwise at risk of a particular disease. Such an amount is defined to be a "prophylactically effective dose" and is also an amount sufficient to inhibit binding of VLA-4-expressing leukocytes to CS-1 compound-expressing endothelial cells. In this use, the precise amounts again depend on the patient's state of health and weight, but generally range from about 1 mg/kg/day to about 500 mg/kg/day, more commonly from about 1 mg/kg/day to about 20 mg/kg/day.

Another way to assess a binding-inhibiting amount of a contemplated inhibitor compound is to compare binding inhibition exhibited by the compound to that provided by CS-1 or the 10-mer standard in an in vitro study. One convenient way to make that comparison is by use of $IC_{50}$ values of the two compared materials, and base the amount used on the amount of CS-1 or standard 10-mer compound and an amount of the inhibitor compound that is a multiple of the $IC_{50}$ value for that reference compound.

Preferably, a compound whose $IC_{50}$ value is at least about one-tenth that of the standard 10-mer (ten-times more potent), when used at one-tenth the molar amount of the 10-mer standard is a useful binding-inhibiting amount. More preferably, the amount is about one-fiftieth the amount of the 10-mer. More preferably still, the amount is equal to about one-hundredth that of the 10-mer. Inasmuch as those amounts inhibit binding by about 50 percent, greater concentrations that inhibit binding still further are preferred.

Thus, for in vitro use, a minimal CS-1/VLA4-inhibiting amount is the $IC_{50}$ value. For in vivo use, the CS-1/VLA-4-inhibiting amount usually used begins with the $IC_{50}$ value concentration, and can decrease as required or one can increase to the solubility limit of the compound in the utilized aqueous medium; i.e., the aqueous medium at pH 7.2–7.4 used such as normal saline where parenteral administration is used or intestinal fluid where oral administration is used.

Single or multiple administrations of a composition can be carried out with dose levels and pattern being selected by the treating physician or veterinarian. In any event, a pharmaceutical composition is formulated to provide a quantity of an inhibitor compound sufficient to effectively treat the patient.

A pharmaceutical composition embodiment is the inhibitor compound in a pharmaceutically acceptable salt.

Further, a pharmaceutical composition embodiment is the inhibitor compound of the present invention and an antibody to P selectin. Such a composition can treat various conditions, including, for example, restinosis. Another embodiment is the inhibitor compound and an inhibitor of the polylactosamino glycan, sialyl $Le^x$. Such a composition can treat various conditions, including, for example, inflammation.

A process for treating fibronectin CS-1/VLA-4-mediated inflammation is also contemplated wherein the inhibitor compound is administered to a mammal in need of such a treatment. This administration is preferably via a before-discussed pharmaceutical composition. The compound is administered in an inflammation-reducing (CS-1/VLA-4 binding inhibiting) amount. The mammal such as mouse, rat, rabbit, monkey or human is maintained until the compound is eliminated by a natural bodily process. Multiple administrations in a single day, over a period of days or weeks, or for the life of the host mammal, where the mammal is the recipient of an allograft, are contemplated, as are single administrations.

Methods for determining an amount sufficient to inhibit binding between CS-1 and VLA-4 have already been discussed, particularly for in vitro studies. For in vivo uses, there are many published assays to determine if inflammation has been reduced by a particular treatment. For example, one can assess the number of painful joints in an arthritic patient or the patient's mobility before and after treatment. Reduction of effects of an asthma attack can be assayed by measurement of dynamic compliance or lung resistance in laboratory animals as is also well known. The amount of edema observed in DTH is also readily measurable, as are the effects of allograft rejection or its absence compared to standard controls.

EXPERIMENTAL

EXAMPLE 1

Synthesis of X-Leu-Asp-Phe-Z

Protected amino acids, Boc-Phe-OH, Boc-Asp(OBn)-OH and Boc-Leu-OH were purchased from NOVA Biochem Co., La Jolla, Calif. and were used without further purification. Phenylacetic acid, morpholine, diisopropylethylamine (DIEA) and 1-hydroxybenztriazole (HOBt) were obtained from Aldrich Chemical Co., Milwaukee, Wis. Ethyl-3-(3-dimethylamino)-propylcarbodiimide.HCl (EDC) was obtained from Bachem Co., Torrance, Calif. 4 Normal HCl in dioxane was obtained from Pierce Co., Rockford, Ill. used as received.

The $^1$HNMR spectra were recorded on a GE QE-300, 300 MHZ NMR spectrometer.

A. Preparation of Boc-Phe-Morpholinamide

A 250 ml flask was charged with Boc-Phe-OH (10 g, 38 mmol), morpholine (3.3 g, 38 mmol) and 1-hydroxybenztriazole (5.1 g, 38 mmol) in 100 ml dry dimethylformamide (DMF). To this solution was added diisopropylethylamine (DIEA) at zero degrees C. until the pH value reached 8, followed by addition of EDC (8.8 g, 46 mmol). The solution was slowly warmed to room temperature. The mixture was stirred for eight hours at room temperature (about 22° C.). The DMF was removed by vacuum evaporator, ethyl acetate and water were added, and the layers were separated. The aqueous layer was extracted with ethyl acetate (50 ml×2), combined extracts were washed with 1N HCl, saturated NaHCO$_3$, water and brine, dried with MgSO$_4$, filtered and concentrated to give a colorless liquid (12.8 g, 37.7 mmol; 99 percent yield) that was characterized by $^1$HNMR as Boc-Phe-morpholine.

B. Preparation of HCl-Phe-Morpholinamide Salt

Boc-Phe-morpholinamide (12.8 g, 38 mmol) was placed in a 250 ml flask, then 4N HCl in dioxane (30 ml) was added. The mixture was stirred for six hours at which time TLC (silica gel; CHCl$_3$:MeOH:acetic acid, 90:8:2) indicated that the reaction was completed. Dioxane and excess HCl were removed. A white solid, identified by $^1$HNMR as HCl-Phe-morpholinamide, was obtained in 100 percent yield (10.3 g, 38 mmol).

C. Preparation of N-Phenylacetyl-Leu-Asp(β-O-Benzyl)-Phe-Morpholinamide

Boc-Asp(β-OBn)-OH, Boc-Leu-OH and phenylacetic acid were sequentially added to HCl-Phemorpholinamide using the coupling and deprotection procedures, described above. The white solid, thus obtained, was crystallized from ethyl acetate and hexane, and identified by $^1$HNMR as the desired ester in 95 percent yield.

D. Synthesis of N-Phenylacetyl-Leu-Asp(β-O-Bn)-Phe-Morpholinamide

To a solution of the above benzyl ester (10 g, 15 mmol) in methanol (100 ml) was added 10 percent palladium-charcoal (2.0 g). The flask containing this mixture was evacuated and then filled with hydrogen three times. The mixture was then vigorously stirred under a hydrogen atmosphere about five hours until the hydrogenalysis was complete, as indicated by TLC (CHCL$_3$:MeOH:acetic acid, 90:8:2). The reaction mixture was filtered through celite, and the methanol was removed, affording a white solid that was characterized by $^1$HNMR as XLDFZ (8.4 g, 14.5 mmol) in 97 percent yield.

Compounds having other than carboxamide [C(O)—NH$_2$] C-terminal amide-linked Z groups were similarly prepared.

Compounds having a 2-H-isoindole substituent at the amino terminus were prepared by coupling 2H-isoindole-2-acetic acid, 1,3 dihydro-1-oxo-methyl, to amino terminus of the a synthesized fragment using standard compound coupling procedures. See, for example, New, J. S. and Yevich, J. P., *J. Heterocyclic Chemistry*, 21:1355–1360 (1984), which is herein incorporated by reference.

EXAMPLE 2

Exemplary Solid Phase Compound Syntheses

Fmoc protected amino acids, hydroxybenzotriazole (HOBt) and Rink amide MBHA resin were obtained from Nova Biochem, La Jolla, Calif. Diisopropylcarbodiimide (DIC) was obtained from Chem Impex Inc., Chicago, Ill. Piperidine was obtained from Aldrich Chemical Company, St. Louis, Mo. Dimethylformamide (DMF), isopropanol (IPA), dichloromethane (DCM), and dimethylacetamide (DMA) were obtained from Burdick and Jackson, Muskegon, Mich. All of the above reagents were used as supplied by the manufacturer, with no further purification.

The standard deprotection/coupling cycle iterated during this synthesis is described in terms of the first coupling of Fmoc-Pro to the Rink amide MBHA resin:

The Fmoc-MBHA resin (10.6 g., 5 mmoles) was treated with 20 percent piperidine in DMF (130 ml) for three minutes. The solution was removed by filtration and the resin was again treated with 20 percent piperidine in DMF (130 ml) for 17 minutes. The solution was removed by filtration and the resin was washed five times with DMF (130 ml each), two times with IPA (130 ml) and two times with DMF (130 ml). The HOBt ester of Fmoc-D-proline (formed by reacting a solution of 10 mmoles Fmoc-D-proline and 10 mmoles HOBt in 50 ml DMA with 12 mmoles DIC for 20 minutes at room temperature), in DMA (50 ml), was added to the resin and allowed to react for two hours. The resin was washed five times with DMF (130 ml) and two times with DCM (130 ml). The coupling of amino acid to the resin was checked by standard Kaiser's test.

The above cycle was iterated for each of the subsequent amino acids: Fmoc-Phe, Fmoc-Asp(β-ON), Fmoc-Leu, and phenylacetic acid. The resin was dried in vacuo for 24 hours and then allowed to react with 95 percent TFA/5 percent H$_2$O (60 ml) for two hours at room temperature. The TFA solution of the compound was separated from the resin by filtration and the TFA was vacuum evaporated. The solid residue was crystallized from anhydrous ethanol to yield 1.8 g of product, Compound ID No. 896.52, N-phenylacetyl-Leu-Asp-Phe-D-Pro-NH$_2$. The compound was characterized by amino acid analysis on HP Amino Quant 1090 and NMR, and the purity of the compound was checked by HPLC (WATER HPLC Systems).

EXAMPLE 3

In Vitro Binding Assays

Jurkat cells (ATCC TIB 152), a human T lymphoblastic line, labeled with $^{51}$chromium were used to assay in vitro binding inhibition provided by various compounds discussed herein. Costar™ 96 well flat-bottom microtiter plates (catalog No. 9050, Cambridge, Mass.) were found to provide the best results in these assays.

The plates were prepared as follows: The 25-mer CS-1 compound (SEQ ID NO:1) dissolved at 0.5–1 µg/ml in a buffer of 0.1M NaHCO$_3$ at pH 9.5 that also contained 10 µg/ml of bovine serum albumin (BSA) or a conjugate of the CS-1 compound linked to ovalbumin (CS-1-OVA) dissolved at 1–2.5 µg/ml in the same buffer was used as the substrate. Each well of the microtiter plates was coated with 50 µl of substrate or buffer alone for controls. The wells were permitted to dry out completely and were then rinsed twice with PBS at pH 7.4. Non-specific binding sites of each well were then blocked using 200 µl per well of RPMI/1 percent BSA for two hours at room temperature. Both solid phase-affixed substrates provided similar results.

Jurkat cells (3–5×10$^6$ cells) were placed into a 15 ml Falcon™ round-bottom tube with a cap. The tube was centrifuged, and the extra medium was then removed.

Two hundred microliters of a $^{51}$Cr labeling solution were added to the centrifuged cells and maintained in contact with the cells for 90–120 minutes in a warm room. This procedure typically provides about 50,000–100,000 cpm/well with about 80–100 percent cell viability. Longer contact times provide a greater amount of labeling but lower cell viability.

The labeled cells are washed with (i) complete medium, (ii) 1 mM EDTA/PBS and then (iii) RPM1/1 percent BSA free of serum components. The cells are centrifuged after each washing. The cells are finally resuspended in serum-free RPMI/1 percent BSA at a concentration of 1×10$^6$ viable cells/ml, which provides a concentration that is diluted by one-half in the assay.

Inhibitor compounds are prepared as stock solutions at 20 mg/ml in DMSO in 1.5 ml cryogenic screwcap vials, and were stored at −70° C. Using Flow™ round-bottom or V-bottom microtiter plates, the inhibitor compounds were prepared at twice the assay concentration in RPMI/1 percent BSA at 60 µl/well.

Four initial dilutions were typically used. For less potent compounds such as the standard 10-mer of SEQ ID NO:3, the initial dilutions were 500 µg/ml, 100 µg/ml, 20 µg/ml and 4 µg/ml. For more potent compounds such as N-phenylacetyl-Leu-Asp-Phe-D-Pro-NH$_2$, the typical initial concentrations were 10 µg/ml, 2 µg/ml, 0.4 µg/ml and 0.08 µg/ml.

The $^{51}$Cr-labeled cells (1×10$^6$ cells at 60 µl/well) were then admixed with the diluted compound solutions. The admixtures were maintained at room temperature (about 22° C.) for 30 minutes.

One hundred microliters of each inhibitor compound/cell admixture were transferred to the substrate-coated wells. This was done in triplicate for each dilution. The resulting plates were incubated for 30 minutes at 37° C. and then washed gently three times with RPMI/1 percent BSA at 200 µl/well. Binding was observed microscopically, particularly after the second wash.

The bound cells were then lysed by the addition of a 0.5 percent solution of sodium dodecylsulfate in water at 100 µl/well. The resulting solutions were then processed for counting and calculation of IC$_{50}$ values following usual procedures. Appropriate positive and negative controls were used with each plate so that the results of separate assays could be normalized and compared.

The data of Table 1 are normalized to the binding of SEQ ID NO:3. The absolute IC$_{50}$ value for the compound ID No. 1051.01, N-phenylacetyl-Leu-Asp-Phe-morpholinamide, is approximately 0.18–0.30 µM. Multiple assays for the same compound were averaged.

EXAMPLE 4

Delayed Type Hypersensitivity in Mice

A. Initial Study

Chisholm et al., *Eur. J. Immunol.*, 23:682–688 (1993) reported in vivo results of blocking VLA-4 interactions in a murine contact hypersensitivity model using rat anti-mouse α-4-antibodies. Those workers noted that therapeutics designed to interfere with VLA-4-mediated adhesion should be effective blockers of in vivo inflammatory processes.

An adoptive transfer delayed-type hypersensitivity murine model has been developed using splenic T cells primed to oxazolone. This model is described in Elices et al., *Clin. Exp. Rheum.*, 11(Suppl. 8):577–580 (1993), whose procedures were followed here.

Thus, BALB/c mice were shaved on the belly and painted (50 µl on the belly and 5 µl on each paw) with three percent oxazolone in acetone/olive oil (4:1) at days zero and 1. At day 5, the mice were sacrificed, their spleens removed, and splenic T cells were obtained via nylon wool columns.

Normal saline or saline containing 25×10$^6$/animal of the oxazolone-immune T cells were separately injected into naive mice. The mice were then challenged by painting 10 µl of 2 percent oxazolone onto one ear each. All procedures were carried out under sterile conditions and in endotoxin-free buffers.

Prior to challenge or saline injection, the mice were implanted with pumps that subcutaneously administered normal saline, normal saline containing the compound, Compound ID No. 896.52, N-phenylacetyl-Leu-Asp-Phe-D-Pro-NH$_2$, or normal saline containing a compound with a scrambled sequence continually at 6 mg/kg/day for a 24-hour time period. The swelling diameter at the site of challenge or saline injection was measured with a microcaliper 24 hours thereafter.

The results of this study are shown in the graph of FIG. 5 for the saline and recited inhibitor compound treatments. Although there is a slight overlap in the data possibly due to non-CS-1-mediated inflammation, it is clear that administration of a contemplated inhibitor compound reduced this type of CS-1/VLA-4-mediated immunoinflammation as compared to the untreated controls. Use of the control compound provided no reduction of inflammation.

B. Expanded Study

An expanded study was carried out as described above except that a scrambled compound control was not used as a control for further inhibitor compounds of Table 1 with larger groups of mice. Statistical analyses were carried out versus injection of vehicle alone. As shown below in Table 6, inhibitor compounds resulted in a statistically significant reduction in post-challenge swelling.

TABLE 6

| Compound ID No. Compound n | Percent Inhibition | p Values |
|---|---|---|
| 896.52 φAc—Leu—Asp—Phe—D—Pro—NH$_2$ 30 | 36 | 0.0002 |
| 1070.02 φAc—Leu—Asp—Phe—4-hydroxpiperidinamide 8 | 29 | 0.015 |
| 1111.06 φAc—Leu—Asp—Phe—4-N(carboxy-methyl)piperazinamide 24 | 30 | <0.0001 |

*φAc = N-phenylacetyl.

The transferred T cell is the effector cell in the adoptive immune response examined here. T cells express both VLA-4 and VLA-5 that interact with the CS-1- and RGD-containing portions of fibronectin, respectively, during an inflammatory immune response. Ferguson et al., *Proc. Natl. Acad, Sci., USA*, 88:8072–8076 (1991) showed that about 50 μg/ml of the standard compound used here (SEQ ID NO:3) when admixed with immune T cells could abrogate a transferred immune response such as the response studied here. Those workers also taught that separate administration of the compound and T cells did not lead to that abrogation.

Here, it is seen that separate administration of 6 μg/ml of a contemplated inhibitor compound provided substantial inhibition of the immune response. It is also seen that the inhibitor compound and T cells need not be premixed here as they were required to be in the Ferguson et al. results.

EXAMPLE 5

Treatment of Asthmatic Rabbits

Six New Zealand white rabbits were immunized with house dust mite antigen from birth through four months of age. Upon immunization, three rabbits received a single nebulizer administration of the inhibitor compound, Compound ID No. 1051.01, N-phenylacetyl-Leu-Asp-Phe-morpholinamide in aqueous 50 percent ethanol as diluent in an amount of 100 mg/kg, and the other three received diluent alone. All of the rabbits were challenged with house dust mite antigen about 15–30 minutes after administration of the compound, with those animals not receiving compound serving as controls.

Once immunized and challenged, the inflammatory state subsides to a basal level within about three weeks. The three animals used as controls were thereafter used as subjects for receipt of an inhibitor compound, and the three rabbits that initially received the compound can serve as controls.

Such a crossover study was done here. Thus, the three initial control rabbits were treated with the above inhibitor compound in the above diluent at a time more than three weeks after the above study, and the three previous recipients of the compound were administered the diluent alone. All six were than challenged again.

Initial pulmonary function, measured by dynamic compliance ($C_{dyn}$) and lung resistance ($R_L$), and bronchoalveolar lavage (BAL) to obtain an effector cell count, here eosinophils, were conducted prior to administration of the compound or diluent for both portions of this crossover study. Similar assays were then taken one-half hourly after challenge for six hours (early phase allergic reaction) and at 24 hours after challenge (late stage allergic reaction) for both portions of this study.

These studies were conducted as described by W. J. Metzger in *CRC Handbook of Late Phase Reactions*, W. Dorsch, ed., Chapter 35, CRC Press, Boca Raton, Fla. (1990) pages 347–362.

Figure 4A:
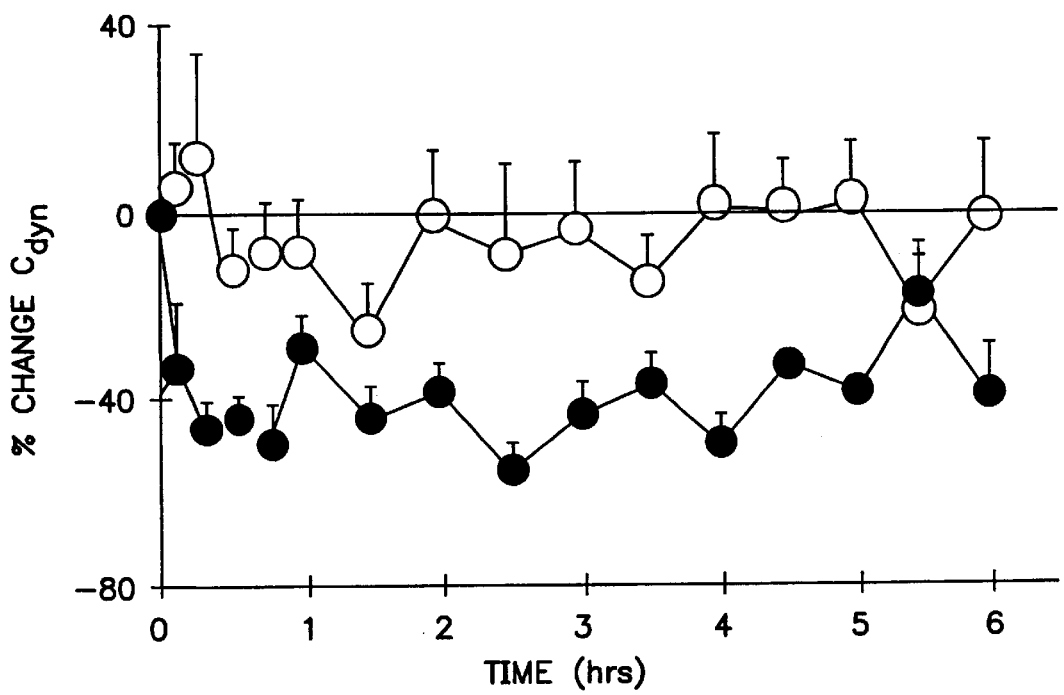
FIG. 4A shows the percent change in dynamic compliance ($C_{dyn}$) over a six-hour time period immediately following the onset of induced asthma attacks. Data for rabbits treated by a nebulized composition containing the inhibitor compound N-phenyl acetyl-Leu-Asp-Phe-morpholinamide are shown as open circles, whereas data for untreated rabbits are shown with darkened circles; both circles including error bars. The ordinate is in units of percent change from the initial dynamic compliance value, whereas the abscissa is in units of hours after challenge.
Figure 4B:
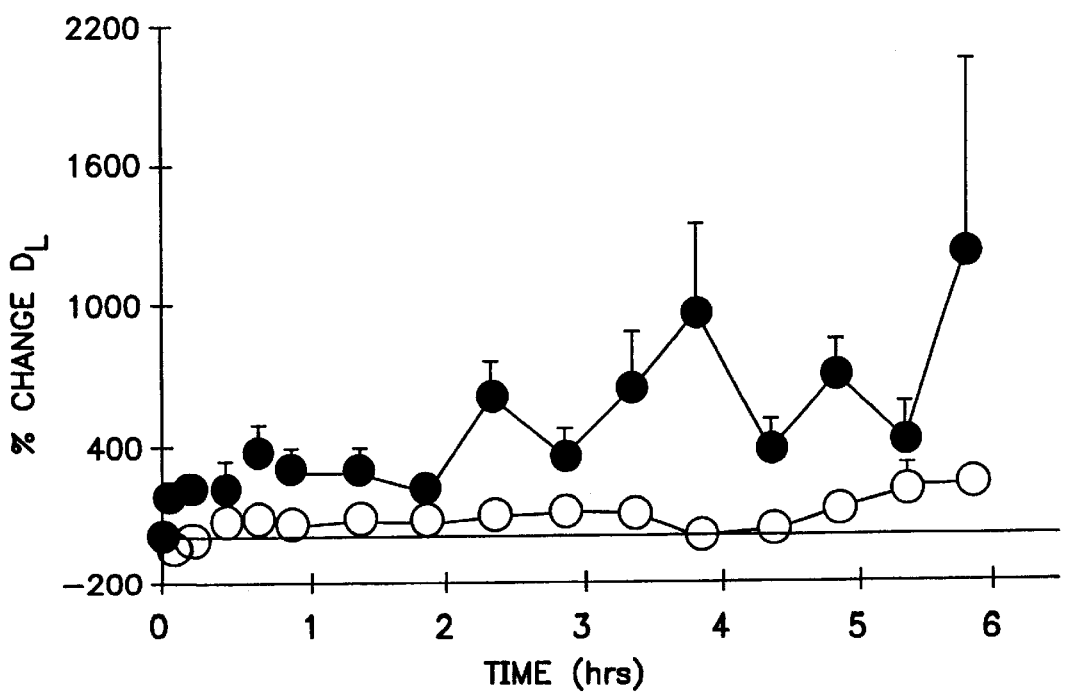
FIG. 4B illustrates the effects of a contemplated compound in treating asthma in the rabbit.

The results of this study for the pulmonary function parameters are shown in FIG. 4A and FIG. 4B, in which data for the challenged, inhibitor compound-treated animals are shown as open circles and data for the challenged, untreated, control animals are shown in blackened circles. These data are averaged values from both portions of the study.

As is seen from FIG. 4A, the $C_{dyn}$ value for the challenged and treated animals stayed at about the initial value for the whole six hours. The $C_{dyn}$ for the challenged, untreated animals quickly fell to about 40 percent of the initial value and then stayed at about that value for the whole six hours.

The data of FIG. 4B show that the $R_L$ values for the challenged, inhibitor compound-treated animals remained between the initial value and about 200 percent of that value for the whole six hours, with a slight rise near the end of that time period. The $R_L$ values for the challenged, but untreated animals rose to about 200–300 percent in the first two hours after challenge and rose to about 400–1200 percent for the last four hours.

A summation of the averaged data for the inhibitor-treated, challenged animals compared to the challenged control animals for early (2–4 hours) and late (24 hours) phases of this inflammatory immune response is provided in Table 7, below.

TABLE 7

IN VIVO Efficacy of Compound ID No. 1051.01
(φAc—Leu—Asp—Phe—Morph*)

| Parameter | Phase | % Reduction |
|---|---|---|
| $C_{dyn}$ | Early | 94.4 |
|  | Late | 86.6 |
| $R_L$ | Early | 80.1 |
|  | Late | 82.6 |

*Phenylacetyl—Leu—Asp—Phe—morpholinamide

The BAL count from these studies indicated an 88.1 percent reduction in eosinophils after 24 hours in the inhibitor compound-treated, challenged animals as compared to the untreated, challenged animals in the crossover study.

As can be seen from the above data and those of FIGS. 4A and 4B, aerosol administration of an inflammation-reducing amount of a contemplated compound greatly reduced the asthmatic response in the treated animals as compared to those receiving no treatments.

EXAMPLE 6

Rabbit Cardiac Allograft Model

New Zealand white rabbit SPF hearts were allografted into the necks of similar rabbits to assay a graft-vs-host immunorejection model and the affect of a contemplated compound on that immunoinflammatory response.
Experimental animal model
New Zealand white female rabbits (Charles River Lab., Saint Laurent, Quebec), between 3.5 and 4 kg underwent heterotopic cardiac transplant following an experimental protocol previously described [Alonso et al., *Am. J. Pathol.*, 87:415–442 (1977); Clausell et al., *Circulation*, 89:2768–2779 (1994)]. The animals were unselected to favor an HLA-mismatch, the host rabbits were Pasteurella-free and the donors, outbred animals. Both host and donor rabbits were fed Purina 5321-0.5 percent cholesterol diet (Research Diets Inc., New Brunswick, N.J.), a strategy that has proven useful in accelerating the process of allograft arteriopathy [Alonso et al., Am. J. Pathol., 87:415–442 (1977)]. The diet was commenced four days prior to the transplant and continued in the recipient of the transplant until the completion of the experimental period.

The technique of heterotopic cardiac transplantation has been previously described [Clausell et al., Circulation, 89:2768–2779 (1994)]. Briefly, a vertical incision was performed in the anterior aspect of the neck of the recipient rabbit and the left common carotid artery and the ipsilateral external jugular vein were isolated. The cardiac allograft was placed in the neck by anastomosing the aorta end-to-side to the recipient's carotid artery and the pulmonary end-to-side to the recipient's external jugular vein, following a total period of ischemia for the donor hearts of approximately 30 minutes. Postoperative care was in compliance with the Principles of Laboratory Animal Care formulated by the Canadian National Society for Medical Research.

The treatment consisted of an inhibitor compound, Compound ID No. 896.52, N-phenylacetyl-Leu-Asp-Phe-D-Pro-$NH_2$ (treated), derived from the leucine-aspartate-valine (LDV) sequence [Komoriya et al., J. Biol. Chem., 266:15075–15079 (1991; Wayner et al. J. Cell Biol., 116:489–497 (1992)], that enhanced inhibition in vitro here, and a scrambled form of the same synthetic compound, N-phenylacetyl-Asp-Leu-Phe-D-Pro-$NH_2$ (control), resulting in no inhibition of VLA-4. Both compounds were synthesized at Cytel Corporation, San Diego, Calif.

Beginning the day of the transplant, the animals were randomized and treated with either scrambled compound (control group) at 1 mg/kg s.c. or the inhibitor compound at 1 mg/kg s.c. The doses of the compounds were empirically extrapolated to the in vivo model based on preliminary in vitro studies, of Table 1. No other immunosuppression therapy was administered. The grafts were monitored daily by palpation and maintained for 7 to 8 days, a previously described endpoint that was associated with myocardial rejection (impaired cardiac contractility) and development of the allograft arteriopathy in this model [Clausell et al., Circulation, 89:2768–2779 (1994)]. A total of fourteen animals were studied in the control (n=7) and treated (n=7) groups.

Preparation of the hearts

The animals were sacrificed using a lethal dose of euthanol (480 mg i.v.) (MTC Pharmaceutical, Cambridge, ON), host and donor hearts were removed, and the coronary arteries were perfused with saline through the aorta, followed by light fixation by perfusion with 2 percent paraformaldehyde (Sigma, St, Louis, Mo.). Because of previous descriptions indicating that cardiac allograft arteriopathy in the rabbit was equally distributed throughout the coronary circulation [Foegh et al., Transplant Proc., 21:3674–3676 (1989)] and those of Dr. Rabinovitch and co-workers [Clausell et al., Circulation, 89:2668–2779 (1994)], the hearts were sectioned transversely from base to apex. Different sections of the hearts were either saved in 10 percent formalin (BDH Inc., Toronto, ON) for light microscopy studies or immediately frozen in O.T.C. Compound Tissue Tek (Miles Inc., Elkart, Ind.) for specific immunohistochemistry studies.

Grading of rejection

Tissue specimens from the donor hearts were stained with hematoxylin:eosin for histological grading of rejection according to a modified Billingham's criteria [Billingham, Hum. Pathol., 10:367–386 (1979)]. The sections were graded by a pathologist without knowledge of whether the donor hearts came from control or inhibitor compound treated animals.

Quantitative assessment of host and donor coronary arteries by light microscopy

Three different paraffin-embedded tissue sections from host and donor hearts from both control and treated rabbits were stained by the Movat pentachrome method for light microscopy. Morphometric analysis was performed using a Zeiss microscope attached to a computer-generated video analysis system (Perceptics Inc., NuVision software), as described in Clausell et al., Circulation, 89:2768–2779 (1994). The number of vessels with intimal lesions were counted in all three heart sections from each animal studied and are expressed as a percentage of the total vessel number.

In the host hearts, 999 vessels in the control group and 1054 vessels in the treated group were analyzed. In the donor hearts, 827 vessels in the control group and 617 vessels in the treated group were analyzed. To determine the severity of intimal thickening, the diameter of each traceable vessel in all three sections was measured and the coronary arteries were categorized as small (diameter <100 $\mu$m), medium (diameter >100<500 $\mu$m) and large (diameter >500 $\mu$m). The degree of intimal thickening was then quantitatively assessed in each vessel size category as previously described in Eich et al., Circulation, 87:261–269 (1993). The areas encompassed by the outer medial layer (ML), the internal elastic lamina (IEL) and lumen were measured in each affected vessel, and the area of intimal thickening (IT) related to the vessel area was calculated by the formula IT=IEL-lumen area/ML-lumen area×100.

Immunohistochemistry studies

In all immunohistochemistry analyses, coronary arteries from host and donor hearts were compared, with and without intimal thickening in the different size ranges from control and treated groups. The relative abundance of each specific antigen studied in the sections examined was graded semi-quantitatively as minimal (±), little (+), moderately abundant (++) to very abundant (+++) two investigators. The final scoring was based on individual gradings that reached 90 percent agreement.

(1) Characterization of inflammatory cells

To characterize the presence of an immune-inflammatory reaction in the allograft coronary arteries in both groups studied, immnunoperoxidase staining was performed using monoclonal antibodies to rabbit MHC Class II antigens and rabbit T cells (from Dr. Peter Libby, Brigham and Woman's Hospital, Boston, Mass.) and also to rabbit macrophages (RAM 11, Dako Corp., Carpinteria, Calif.). The sections were air-dried for two hours, fixed in acetone for 20 minutes, and rinsed with D-PBS (Gibco, Burlington, ON)/0.1 percent BSA (Boehringer-Mannheim, Mannheim, Germany). Endogenous peroxidase activity was blocked by immersing the sections in PBS/0.1 percent BSA+3 percent hydrogen peroxide (BDH) for 30 minutes. After a non-specific blocking step using 10 percent normal goat serum (Sigma), the antibodies were applied to the sections for 1 hour at a 1:10 dilution at room temperature. The sections were then rinsed, incubated with goat anti-mouse peroxidase-conjugated secondary antibody (Bio-Rad, Richmond, Calif.) at a 1:50 dilution at room temperature for 45 minutes and developed with 3,3'-diaminobenzidine (DAB) (Sigma) for 10 minutes. Control sections were treated with normal mouse isotypic IgG (Dako Corp.).

(2) Immune-detection of cellular adhesion molecules

To assess the influence of treatment on the expression of adhesion molecules in allograft coronary arteries, immunoperoxidase staining for ICAM-1 and VCAM-1 was performed on frozen sections of both host and donor hearts from the control and the treated groups. Monoclonal antibodies to ICAM-1 (mAb Rb2/3) and to VCAM-1 (mAb Rb1/9) (from Dr. Myron Cybulsky of Brigham and Women's Hospital, Boston, Mass.) and were used at a concentration of 1:10 for 1 hour at room temperature. The procedure for immunostaining was essentially the same as described above.

(3) Assessment of fibronectin

Fibronectin expression in coronary arteries of host and donor hearts from both control and treated groups was determined by performing immunoperoxidase staining using frozen sections. A monoclonal antibody anti-cellular fibronectin (Chemicon Int. Inc., Temecula, Calif.) was used at a dilution of 1:100 for 1 hour at room temperature and the remaining details of the immunohistochemical procedure are essentially the same as described above. This antibody does not recognize plasma fibronectin.

Statistical Analysis

The data were expressed as mean ±SE. In analyses related to the incidence and severity of lesions from both control and treated groups, the Student's t test was used to test significance. The correlation among categorical variables from the immunohistochemistry studies, considered positive if >+ in the two groups (control and treated), was analyzed using Fisher's exact test. Differences were considered significant if $p<0.05$.

The results of the above studies are summarized in Table 8, below.

TABLE 8

| Expression on Coronary Arteries | Inhibitor Compound | Control Compound |
| --- | --- | --- |
| MHC Class II | ±[c] | ++ |
| T cells | ± | ++ |
| Macrophages | ± | + |
| ICAM-1 | ± | + |
| VCAM-1 | ± | + |
| Total Fibronectin | ± | ++ |
| Vessel Intimal Thickening | | |
| Percent of Vessels[a] | 35[d] | 88 |
| Severity (Percent of Vessel area)[b] | 16[e] | 36 |

[a]Baseline (rabbit own host heart) of incidence was 12 percent and 10 percent, respectively, for inhibitor and control compound groups.
[b]Baseline (rabbit own host heart) of severity was 12 percent and 12 percent, respectively, for inhibitor and control compound groups.
[c]Scoring was: −, negative; ±, minimal; +, little; ++, moderately abundant; +++, very abundant.
[d]$p < 0.001$.
[e]$p < 0.001$.

As is seen from the above results, use of a contemplated inhibitor compound greatly reduced the inflammation-induced damage observed in the allografted hearts. These damage reductions are particularly evident in the vessel intimal thickening results, but are also seen less directly in the results relating to expressed inflammatory markers shown by the MHC Class II antigen, the increased presence of T cells and macrophages, and the total fibronectin.

EXAMPLE 7

In Vitro Porcine Allograft Model

A similar study was carried out in vitro using porcine coronary artery endothelial cells (EC; as are present in the IEL) and smooth muscle cells (SMC; as are present in the medial layer of the artery). The two cell types were cultured using a membrane transwell system, with the SMC on the bottom layer in M-199 medium (Gibco Labs.). The SMC were stimulated with 100 ng/ml of interleukin-1β (IL-1β) for 24 hours prior to the start of the assay. Porcine peripheral blood lymphocytes were separated by Ficoll-Hypaque, radiolabeled and incubated overnight (about 18 hours) on the EC.

Transendothelial lymphocyte migration in the IL-1β-stimulated SMC was observed as compared to unstimulated SMC ($p<0.05$). The inhibitor compound of Example 6, Compound ID No. 896.52, phenylacetyl-Leu-Asp-Phe-D-Pro-NH$_2$, present at 10 μg/ml in the medium reduced lymphocyte migration by about 30 percent ($p<0.05$), whereas the same amount of a control compound whose sequence was scrambled did not reduce migration.

Increased expression of EC and SMC fibronectin and IL-1β are features of an immunoinflammatory response associated with accelerated graft arteriopathy following piglet heterotopic cardiac transplantation. The above results indicate that IL-1β induces fibronectin production in this in vitro model, which in turn contributes to transendothelial lymphocyte migration. The above results also illustrate that a contemplated inhibitor compound can be used to reduce this immunoinflammatory response.

EXAMPLE 8

Experimental Autoimmune Encephalomyetlitis in Mice

Experimental autoimmune encephalomyelitis (EAE) is a demyelinating disease of the central nervous system that can be induced in susceptible strains of mice and rats by immunization with myelin basic protein, proteolipid protein (PLP), or their immunodominant T cell determinants, or by injection of CD4-positive T cell clones specific for those determinants. EAE serves as an animal model of human multiple sclerosis. In both diseases, circulating leukocytes such as T cells and monocytes penetrate the blood/brain barrier and damage myelin, resulting in paralysis.

EAE was induced in female SJL/J mice (8 to 14 weeks old) by immunization on day zero with 50 μg of a compound corresponding to positions 139–151 of PLP emulsified in a 1:1 mixture of PBS and complete Freund's adjuvant (CFA). Each mouse was injected with 0.2 ml of the adjuvant emulsion subcutaneously (s.c.) at two sites in the hind flank. All mice received $10^7$ killed Bordetella pertussis units in 100 μl were injected intravenously 24 to 72 hours later.

Mice were observed daily, beginning at day 8 for clinical signs of EAE, and disease was scored on a scale of 0–5 as: 0=no disease; 1=floppy tail; 2=moderate hind limb weakness; 3=paraparesis; 4=paraplegis with moderate forelimb weakness; 5=qualdriplegis or premoribund state.

The inhibitor compound, Compound ID No. 896.52, N-phenylacetyl-Leu-Asp-Phe-D-Pro-NH$_2$ was administered intraperitoneally at 1 mg/mouse in 0.2 ml of incomplete Freund's adjuvant at days 8 and 9. A compound having a scrambled sequence [N-phenylacetyl-Asp-Leu-Phe-D-Pro-NH$_2$] was similarly administered to serve as a control. The relative potency of this control compound is shown in Table 1 to be 0.

Summed or averaged scores for clinical signs were plotted vs. time. The area under the resulting curves was calculated between day 8 and day 35 to calculate percentage inhibition of EAE by an inhibitor compound. The percent inhibition was calculated as follows:

% Inhibition=100-(Area of inhibitor compound÷control area)×100

Figure 6:
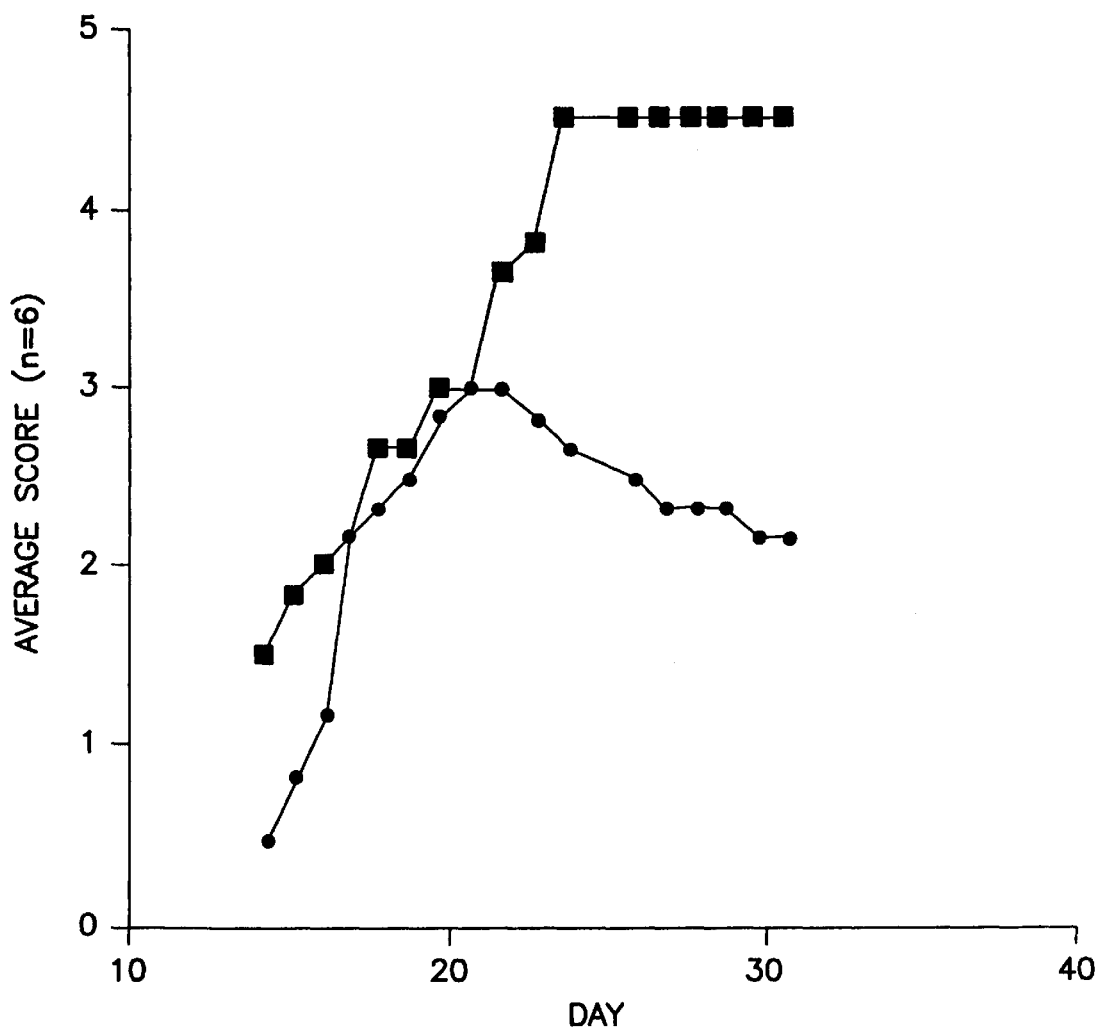
FIG. 6 is a graph showing averaged clinical scores for six mice each in two evaluations of treatments of experimental autoimmune encephalomyelitis (EAE). Darkened circles are for treatments using the inhibitor compound N-phenyl acetyl-Leu-Asp-Phe-D-Pro-$NH_2$, whereas points shown as darkened squares are for treatments using the control sequence compound of Example 6. The ordinant shows the averaged score for the six mice in each study, whereas the abscissa is in days after initiation of EAE.

Two exemplary plots through day 31 are shown in the graph of FIG. 6 in which the darkened circles are averaged scores for six mice treated with the inhibitor compound and darkened squares are averaged scores for six mice that received the scrambled sequence control compound. As can be seen, animals treated with an inhibitor compound contemplated herein exhibited marked improvement in clinical signs as compared to those animals treated with the control compound.

EXAMPLE 9

CS-1 Expression in Human Rheumatoid Arthritis

Surgically-obtained synovial specimens from human rheumatoid arthritis (RA) patients were examined microscopically for the expression of the CS-1 compound portion of fibronectin. Ultrathin sections of tissue were stained by the immunoperoxidase technique using anti-CS-1 antibodies, and were studied using transmission electron microscopy. These studies showed that CS-1 was expressed on the lumenal aspect of blood vessel endothelium, on the lumenal plasma membrane. The plasma membrane of synoviocytes in the synovial intimal lining at the interface with the joint space was also stained. The CS-1 compound portion was not found to be expressed in normal synovium.

Binding studies were carried out using the Jurkat T cell line and frozen RA synovial sections. Jurkat cell adhesion could be inhibited by anti-VLA-4 antibodies or the 10-mer CS-1 compound portion (500 μg/ml) used as standard here (SEQ ID NO:3), but not with antibodies to VLA-5, VCAM-1-A or VCAM-1-B or a compound in which the 10-mer sequence was scrambled. Stimulated MOLT-4 cells behaved similarly. These results are reported in Elices et al., *J. Clin. Invest.*, 93:405–416 (January 1994).

A similar inhibition of binding of Jurkat cells to human RA synovial sections and not to normal synovial sections was observed using the inhibitor compound, Compound ID No. 896.52, N-phenylacetyl-Leu-Asp-Phe-D-Pro-NH$_2$. That compound was used at its IC$_{50}$ value shown in Table 1 to be about 312 times less than the IC$_{50}$ value for the standard 10-mer. The absolute value of that IC$_{50}$ value is about 0.5 μmolar.

These results illustrate the importance of the CS-1 compound portion and VLA-4 in a human chronic immunoinflammatory disease state, rheumatoid arthritis. These results also show that a contemplated inhibitor cell can inhibit the binding of inflammatory cells in this human immunoinflammatory disease state.

EXAMPLE 10

Treatment of Asthmatic Sheep

Six asthmatic sheep were treated in a double blind crossover study. The sheep had been shown to develop both early and late bronchial responses to inhaled *Ascaris suum* antigen. This study was carried out generally as described in Abraham et al., *J. Clin. Invest.*, 93:776–787 (1994).

The inhibitor compound used here was Compound ID No. 896.52, N-phenylacetyl-Leu-Asp-Phe-D-Pro-NH$_2$, with a control compound that comprised the previously described compound having the same residues in a scrambled sequence. The vehicle for the nebulized compounds was phosphate-buffered saline. The compounds were administered at a dose of 1 mg/kg each, twice a day for three days prior to challenge, as well as 0.5 hours prior to and four hours post challenge on day 4. Because this was a crossover study, each animal received one or the other treatment, followed by a rest and then the other treatment. Each animal therefore served as its own control.

Figure 7:
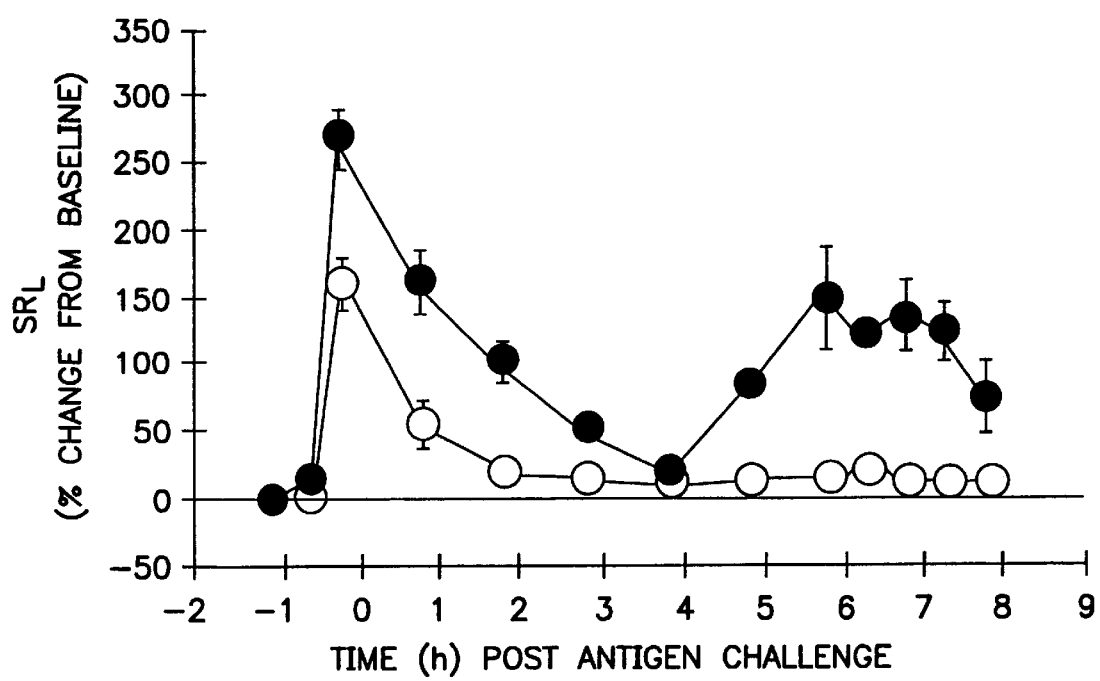
FIG. 7 is a graph showing the percentage of change in lung resistance, $SR_L$, from base line for the asthmatic sheep model depicted as described in FIG. 4B. The nebulized composition here contained N-phenyl acetyl-Leu-Asp-Phe-D-Pro-$NH_2$ in open circles and the control sequence of that compound (Example 6) in darkened circles, including error bars where appropriate.

As can be seen from the graph of FIG. 7, animals treated with the inhibitor compound exhibited less of a change from baseline specific lung resistance (SR$_L$) on challenge and then more rapidly returned to their baseline pulmonary functions than did animals treated with the control compound. In addition, pulmonary function remained at about baseline values from about 3–4 hours after challenge through the end of the study (8 hours post challenge), whereas the control compound-treated animals had an increase in that pulmonary function (SR$_L$).

Post challenge airway responsiveness was also assayed. Here, specific lung resistance, SR$_L$, returned to baseline values 24 hours after challenge, however, the sheep were hyperresponsive to inhaled carbachol at that time. A comparison of PC$_{400}$ values on carbachol inhalation prior to and 24 hours after challenge indicated that a much smaller dosage of carbachol [about 12 breath units (BU)] was required to increase the SR$_L$ value for control compound-treated animals 4-fold over a saline control value, as compared to the amount required for the inhibitor compound-treated group (about 27 BU). The pre-challenge values here were about 20–23 BU, so that the inhibitor compound caused the animals' SR$_L$ to be greater than pre-challenge values, indicating a lessened response to carbacol than the pre-challenge response.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A prodrug compound having the following structural formula:

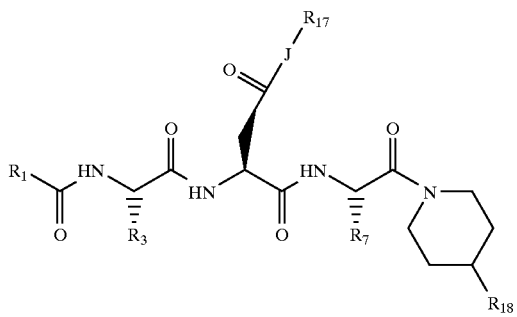

where:
J is a NH group, oxygen atom, or sulfur atom;
R$_{17}$ is an alkyl, phenylalkyl, alkanoic acid, alkyl phosphonate, biotin, or hydrogen;
when J is the NH group, R$_{17}$, taken together with the —(CO)NH— group to which R$_{17}$ is bonded, is a carboxamide, alkyl carboxamide carboxylic ester or an N-alkylcarboxamide;
when J is the oxygen atom, R$_{17}$, taken together with the —(CO)O— group to which R$_{17}$ is bonded, is an alkyl ester, an alkyl carboxylic ester or alkyl phosphonate; and
when J is the sulfur atom, R$_{17}$, taken together with the —(CO)S— group to which R$_{17}$ is bonded, is an alkyl thioester, $R_{18}$ is an alkyl ester, biotin or H group with the proviso that $R_{17}$ and $R_{18}$ cannot both be H groups;

$R_1$ is a $R_1$ ring structure, lower alkyl, or lower amino alkyl; the $R_1$ ring structure is connected by a spacer 0 to about 5 atoms long forming from one or more N-amido, N-sulfonimido, N-urea, N-carboxyl groups; the spacer can be optionally substituted by an amino group; the $R_1$ ring structure is a substituted or unsubstituted 5-, 6-, fused 6,6- or fused 6,5-membered ring wherein the substituent is one or more alkyl, carbonyl, alcohol, halogen, or alkyl phenyl groups; the $R_1$ ring structure is carbocyclic or heterocyclic with the proviso that the heteroatoms are 1 or 2 nitrogen atoms; the $R_1$ ring structure can be aromatic, partially saturated, or saturated; the lower alkyl or lower amino alkyl group can be branched;

$R_3$ is a $R_3$ ring structure, lower alkyl, lower alkyl alcohol or lower thioalkyl; the $R_3$ ring structure group is a 6-membered ring that is connected by an alkyl group 0 to about 3 carbon atoms long; the lower alkyl, lower alkyl alcohol, or lower thioalkyl group can be branched;

$R_7$ is a $R_7$ ring structure, lower alkyl, lower alkyl alcohol, lower thioalkyl or H group; the $R_7$ ring structure forms at $R_7$ and can be connected by an alkyl group 0 to about 3 carbon atoms long and is a 6-, or fused 6,5-membered aromatic or non-aromatic cyclic or heterocyclic ring group wherein the heteroatom is a nitrogen atom; and the $R_7$ ring structure can optionally be substituted by an alcohol, nitro or lower alkyl ether group.

2. A composition comprising the compound of claim 1 and a carrier.

* * * * *